US009128080B2

(12) United States Patent
Robbins et al.

(10) Patent No.: US 9,128,080 B2
(45) Date of Patent: Sep. 8, 2015

(54) MODIFIED T CELL RECEPTORS AND RELATED MATERIALS AND METHODS

(75) Inventors: Paul F. Robbins, Potomac, MD (US); Richard A. Morgan, Columbia, MD (US); Steven A. Rosenberg, Potomac, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 100 days.

(21) Appl. No.: 13/304,841

(22) Filed: Nov. 28, 2011

(65) Prior Publication Data

US 2012/0071420 A1 Mar. 22, 2012

Related U.S. Application Data

(62) Division of application No. 12/443,111, filed as application No. PCT/US2007/079487 on Sep. 26, 2007, now Pat. No. 8,088,379.

(60) Provisional application No. 60/847,447, filed on Sep. 26, 2006.

(51) Int. Cl.

*C07H 21/04* (2006.01)
*G01N 33/50* (2006.01)
*C07K 14/725* (2006.01)
*A61K 38/00* (2006.01)

(52) U.S. Cl.

CPC .......... *G01N 33/505* (2013.01); *C07K 14/7051* (2013.01); *G01N 33/5091* (2013.01); *A61K 38/00* (2013.01)

(58) Field of Classification Search

None

See application file for complete search history.

(56) References Cited

U.S. PATENT DOCUMENTS

| | | | |
|---|---|---|---|
| 4,450,150 A | 5/1984 | Sidman | |
| 5,087,616 A | 2/1992 | Myers et al. | |
| 5,225,539 A | 7/1993 | Winter | |
| 5,449,752 A | 9/1995 | Fujii et al. | |
| 5,545,806 A | 8/1996 | Lonberg et al. | |
| 5,569,825 A | 10/1996 | Lonberg et al. | |
| 5,585,089 A | 12/1996 | Queen et al. | |
| 5,620,886 A | 4/1997 | Brichard et al. | |
| 5,639,641 A | 6/1997 | Pedersen et al. | |
| 5,693,761 A | 12/1997 | Queen et al. | |
| 5,714,352 A | 2/1998 | Jakobovits | |
| 5,837,476 A | 11/1998 | Brichard et al. | |
| 5,854,203 A | 12/1998 | Brichard et al. | |
| 5,856,091 A | 1/1999 | Brichard et al. | |
| 6,001,975 A | 12/1999 | Brichard et al. | |
| 6,201,111 B1 | 3/2001 | Brichard et al. | |
| 6,265,150 B1 | 7/2001 | Tertappen et al. | |
| 2002/0197266 A1 | 12/2002 | Debinski | |
| 2008/0292549 A1* | 11/2008 | Jakobsen et al. | 424/1.69 |
| 2009/0304657 A1 | 12/2009 | Morgan et al. | |
| 2010/0034834 A1 | 2/2010 | Robbins et al. | |

FOREIGN PATENT DOCUMENTS

| | | | |
|---|---|---|---|
| EP | 0 239 400 B1 | 8/1994 | |
| EP | 1 066 380 B1 | 3/2001 | |
| EP | 1 421 115 B1 | 3/2005 | |
| GB | 2 188 638 A | 10/1987 | |
| WO | WO 94/21126 A1 | 9/1994 | |
| WO | WO 96/01557 A1 | 1/1996 | |
| WO | WO 03/020763 A2 | 3/2003 | |
| WO | WO 2004/044004 A2 | 5/2004 | |
| WO | WO 2004/050705 A2 | 6/2004 | |
| WO | WO 2005/113595 A2 | 12/2005 | |
| WO | WO 2005/114215 A3 | 12/2005 | |
| WO | WO 2006000830 A2 * | 1/2006 | |

OTHER PUBLICATIONS

Xue et al. (Clinical and Experimental Immunology, 139: 167-172 (2005)).*
Szymczak et al. (Nature Biotechnology vol. 22 No. 5 May 2004, pp. 589-594).*
Janeway et al., Immunobiology, 5th Ed., Garland Science, pp. 106-108 and 260-263, (2001).*
Garcia et al., Cell, vol. 122, 333-336, Aug. 12, 2005.*
Portolano et al., J Immunol. Feb. 1, 1993;150(3):880-7.*
Baker et al., *Immunity*, 13, 475-484 (2000).
Chen et al., *J. Exp. Med.*, 201 (8), 1243-1255 (2005).
Chen et al., *J. Immunol.*, 165 (2), 948-955 (2000).
Chlewicki et al., *J. Mol. Biol.*, 346, 223-239 (2004).
Choi et al., *Mol. Biotech.*, 31, 193-202 (2005).
Clay et al., *J. Immunol.*, 163, 507-513 (1999).
Dunn et al., *Protein Sci.*, 15 (4), 710-721 (2006).
GenBank Accession No. AF043179 (Nov. 2, 2001).
GenBank Accession No. AF397440 (Aug. 9, 2001).
GenBank Accession No. AY124793 (Sep. 17, 2002).
GenBank Accession No. M13863 (Oct. 23, 2007).
GenBank Accession No. NG_000016 (Jan. 25, 2009).
GenBank Accession No. NG_001332 (Feb. 25, 2009).
GenBank Accession No. NG_001333 (Feb. 16, 2009).
GenBank Accession No. NG_001336 (Sep. 14, 2008).

(Continued)

*Primary Examiner* — Zachary Skelding
(74) *Attorney, Agent, or Firm* — Leydig, Voit & Mayer

(57) ABSTRACT

The invention is directed to a modified T cell receptor (TCR) comprising an amino acid sequence of a wild-type (WT) TCR with no more than three amino acid substitutions, wherein the modified TCR, as compared to the WT TCR, (i) has an enhanced ability to recognize target cells when expressed by $CD4^+$ T cells and (ii) does not exhibit a decrease in antigen specificity when expressed by $CD8^+$ T cells. Polypeptides, proteins, nucleic acids, recombinant expression vectors, host cells, populations of cells, antibodies, and pharmaceutical compositions related to the modified TCR also are part of the invention. Further, the invention is directed to methods of detecting a diseased cell in a host, methods of treating or preventing a disease in a host, and methods of identifying a candidate adoptive immunotherapy TCR.

18 Claims, No Drawings

(56) References Cited

OTHER PUBLICATIONS

GenBank Accession No. NG_001337 (Dec. 22, 2008).
GenBank Accession No. Z81026 (Oct. 21, 1996).
Haskard et al., *J. Immunol. Method*, 74 (2), 361-367 (1984).
Holler et al., *J. Exp. Med.*, 194 (8), 1043-1052 (2001).
Holler et al., *Nat. Immunol.*, 4 (1), 55-62 (2003).
Holler et al., *Proc. Natl. Acad. Sci.*, 97 (10), 5387-5392 (2000).
Huang et al., *J. Immunol.*, 172, 6057-6064 (2004).
Hudecz, *Meth. Mol. Biol.*, 298, 209-223 (2005).
Hughes et al., *Hum. Gene Ther.*, 16, 457-472 (2005).
Huse et al., *Science*, 246, 1275-1281 (1989).
Johnson et al., *J. Immunol.*, 177 (9), 6548-6559 (2006).
Kalergis et al., *J. Immunol.*, 165, 280-285 (2000).
Kalergis et al., *Nat. Immunol.*, 2 (3), 229-234 (2001).
Kirin et al., *Inorg Chem.*, 44 (15), 5405-5415 (2005).
Köhler et al., *Eur. J. Immunol.*, 6, 511-519 (1976).
Lefranc et al., *Nucl. Acids Res.*, 27 (1), 209-212 (1999).
Li et al., *Nat. Biotech.*, 23 (3), 349-354 (2005).
Loftus et al., *J. of Immunology*, 162, 6451-6457 (1999).
Morgan et al., *Sciencexpress*, e-publication (Aug. 31, 2006).
Morris et al., *Blood Reviews*, 20 (2), 61-69 (2006).
Pederson et al., *J. Mol. Biol.*, 235, 959-973 (1994).
Purbhoo et al., *J. Immunol.*, 176 (12), 7308-7316 (2006).
Reiter et al., *Protein Engineering*, 7 (5), 697-704 (1994).
Roder et al., *Methods Enzymol.*, 121, 140-167 (1986).
Skolnick et al., *Trends in Biotechnology*, 18, 34-39 (2000).
Wadhwa et al., *J. Drug Targeting*, 3, 111-127 (1995).
Weber et al., *Proc. Natl. Acad. Sci.*, 102 (52), 19033-19038 (2005).
Zhao et al., *J. Immunol.*, 174 (7), 4415-4423 (2005).
Zhao et al., *J. Immunol.*, 179 (9), 5845-5854 (2007).
Zhao et al., *Mol. Ther.*, 13 (1), 151-159 (2006).
International Search Report of Application No. PCT/US2007/079487.

* cited by examiner

SEQUENCE LISTING

```
<160> NUMBER OF SEQ ID NOS: 121

<210> SEQ ID NO 1
<211> LENGTH: 113
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: AA of variable region of 1G4 mut 1

<400> SEQUENCE: 1

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ser Trp Tyr Arg Gln Asp Pro Gly Met Gly Leu Arg Leu Ile His Tyr
        35                  40                  45

Ser Val Ala Ala Gly Ile Thr Asp Gln Gly Glu Val Pro Asn Gly Tyr
    50                  55                  60

Asn Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Ser Tyr Val
                85                  90                  95

Gly Asn Thr Gly Glu Leu Phe Phe Gly Glu Gly Ser Arg Leu Thr Val
            100                 105                 110

Leu


<210> SEQ ID NO 2
<211> LENGTH: 113
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: AA of variable region of 1G4 mut 2

<400> SEQUENCE: 2

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ser Trp Tyr Arg Gln Asp Pro Gly Met Gly Leu Arg Leu Ile His Tyr
        35                  40                  45
```

Ser Val Gly Ile Gly Ile Thr Asp Gln Gly Glu Val Pro Asn Gly Tyr
    50                  55                  60

Asn Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Ser Tyr Val
                85                  90                  95

Gly Asn Thr Gly Glu Leu Phe Phe Gly Glu Gly Ser Arg Leu Thr Val
            100                 105                 110

Leu

<210> SEQ ID NO 3
<211> LENGTH: 113
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: AA of variable region 1G4 mut 3

<400> SEQUENCE: 3

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ser Trp Tyr Arg Gln Asp Pro Gly Met Gly Leu Arg Leu Ile His Tyr
        35                  40                  45

Ser Val Ala Ile Gly Ile Thr Asp Gln Gly Glu Val Pro Asn Gly Tyr
    50                  55                  60

Asn Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Ser Tyr Val
                85                  90                  95

Gly Asn Thr Gly Glu Leu Phe Phe Gly Glu Gly Ser Arg Leu Thr Val
            100                 105                 110

Leu

<210> SEQ ID NO 4
<211> LENGTH: 112
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: AA of variable region of F5 mut1

<400> SEQUENCE: 4

Ile Ala Gly Ile Thr Gln Ala Pro Thr Ser Gln Ile Leu Ala Ala Gly
1               5                   10                  15

Arg Arg Met Thr Leu Arg Cys Thr Gln Asp Met Arg His Asn Ala Met
            20                  25                  30

Tyr Trp Tyr Arg Gln Asp Leu Gly Leu Gly Leu Arg Leu Ile His Tyr
        35                  40                  45

Ser Asn Thr Ala Gly Ala Thr Gly Lys Gly Glu Val Pro Asp Gly Tyr
    50                  55                  60

Ser Val Ser Arg Ala Asn Thr Asp Asp Phe Pro Leu Thr Leu Ala Ser
65                  70                  75                  80

```
Ala Val Pro Ser Gln Thr Ser Val Tyr Phe Cys Ala Ser Ser Leu Ser
                85                  90                  95

Phe Gly Thr Glu Ala Phe Phe Gly Gln Gly Thr Arg Leu Thr Val Val
            100                 105                 110


<210> SEQ ID NO 5
<211> LENGTH: 113
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: AA of variable region of F4 mut1

<400> SEQUENCE: 5

Asp Ala Gly Ile Thr Gln Ser Pro Arg His Lys Val Thr Glu Thr Gly
1               5                   10                  15

Thr Pro Val Thr Leu Arg Cys His Gln Thr Glu Asn His Arg Tyr Met
            20                  25                  30

Tyr Trp Tyr Arg Gln Asp Pro Gly His Gly Leu Arg Leu Ile His Tyr
        35                  40                  45

Ser Tyr Ala Val Lys Asp Thr Asp Lys Gly Glu Val Ser Asp Gly Tyr
    50                  55                  60

Ser Val Ser Arg Ser Lys Thr Glu Asp Phe Leu Leu Thr Leu Glu Ser
65                  70                  75                  80

Ala Thr Ser Ser Gln Thr Ser Val Tyr Phe Cys Ala Ile Ser Glu Val
                85                  90                  95

Gly Val Gly Gln Pro Gln His Phe Gly Asp Gly Thr Arg Leu Ser Ile
            100                 105                 110

Leu


<210> SEQ ID NO 6
<211> LENGTH: 113
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: AA of variable region of F4 mut2

<400> SEQUENCE: 6

Asp Ala Gly Ile Thr Gln Ser Pro Arg His Lys Val Thr Glu Thr Gly
1               5                   10                  15

Thr Pro Val Thr Leu Arg Cys His Gln Thr Glu Asn His Arg Tyr Met
            20                  25                  30

Tyr Trp Tyr Arg Gln Asp Pro Gly His Gly Leu Arg Leu Ile His Tyr
        35                  40                  45

Ser Tyr Ala Ala Lys Asp Thr Asp Lys Gly Glu Val Ser Asp Gly Tyr
    50                  55                  60

Ser Val Ser Arg Ser Lys Thr Glu Asp Phe Leu Leu Thr Leu Glu Ser
65                  70                  75                  80

Ala Thr Ser Ser Gln Thr Ser Val Tyr Phe Cys Ala Ile Ser Glu Val
                85                  90                  95

Gly Val Gly Gln Pro Gln His Phe Gly Asp Gly Thr Arg Leu Ser Ile
            100                 105                 110

Leu
```

<210> SEQ ID NO 7
<211> LENGTH: 255
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: AA of WT alpha chain of 1G4

<400> SEQUENCE: 7

```
Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Thr Ser
                85                  90                  95

Gly Gly Ser Tyr Ile Pro Thr Phe Gly Arg Gly Thr Ser Leu Ile Val
            100                 105                 110

His Pro Tyr Ile Gln Asn Pro Asp Pro Ala Val Tyr Gln Leu Arg Asp
        115                 120                 125

Ser Lys Ser Ser Asp Lys Ser Val Cys Leu Phe Thr Asp Phe Asp Ser
    130                 135                 140

Gln Thr Asn Val Ser Gln Ser Lys Asp Ser Asp Val Tyr Ile Thr Asp
145                 150                 155                 160

Lys Thr Val Leu Asp Met Arg Ser Met Asp Phe Lys Ser Asn Ser Ala
                165                 170                 175

Val Ala Trp Ser Asn Lys Ser Asp Phe Ala Cys Ala Asn Ala Phe Asn
            180                 185                 190

Asn Ser Ile Ile Pro Glu Asp Thr Phe Phe Pro Ser Pro Glu Ser Ser
        195                 200                 205

Cys Asp Val Lys Leu Val Glu Lys Ser Phe Glu Thr Asp Thr Asn Leu
    210                 215                 220

Asn Phe Gln Asn Leu Ser Val Ile Gly Phe Arg Ile Leu Leu Leu Lys
225                 230                 235                 240

Val Ala Gly Phe Asn Leu Leu Met Thr Leu Arg Leu Trp Ser Ser
                245                 250                 255
```

<210> SEQ ID NO 8
<211> LENGTH: 292
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: AA of WT beta chain of 1G4 (immature)

<400> SEQUENCE: 8

```
Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30
```

```
Ser Trp Tyr Arg Gln Asp Pro Gly Met Gly Leu Arg Leu Ile His Tyr
        35                  40                  45

Ser Val Gly Ala Gly Ile Thr Asp Gln Gly Glu Val Pro Asn Gly Tyr
    50                  55                  60

Asn Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Ser Tyr Val
                85                  90                  95

Gly Asn Thr Gly Glu Leu Phe Phe Gly Glu Gly Ser Arg Leu Thr Val
            100                 105                 110

Leu Glu Asp Leu Lys Asn Val Phe Pro Pro Glu Val Ala Val Phe Glu
        115                 120                 125

Pro Ser Glu Ala Glu Ile Ser His Thr Gln Lys Ala Thr Leu Val Cys
    130                 135                 140

Leu Ala Thr Gly Phe Tyr Pro Asp His Val Glu Leu Ser Trp Trp Val
145                 150                 155                 160

Asn Gly Lys Glu Val His Ser Gly Val Ser Thr Asp Pro Gln Pro Leu
                165                 170                 175

Lys Glu Gln Pro Ala Leu Asn Asp Ser Arg Tyr Ser Leu Ser Ser Arg
            180                 185                 190

Leu Arg Val Ser Ala Thr Phe Trp Gln Asn Pro Arg Asn His Phe Arg
        195                 200                 205

Cys Gln Val Gln Phe Tyr Gly Leu Ser Glu Asn Asp Glu Trp Thr Gln
    210                 215                 220

Asp Arg Ala Lys Pro Val Thr Gln Ile Val Ser Ala Glu Ala Trp Gly
225                 230                 235                 240

Arg Ala Asp Cys Gly Phe Thr Ser Glu Ser Tyr Gln Gln Gly Val Leu
                245                 250                 255

Ser Ala Thr Ile Leu Tyr Glu Ile Leu Leu Gly Lys Ala Thr Leu Tyr
            260                 265                 270

Ala Val Leu Val Ser Ala Leu Val Leu Met Ala Met Val Lys Arg Lys
        275                 280                 285

Asp Ser Arg Gly
    290
```

<210> SEQ ID NO 9
<211> LENGTH: 251
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: AA of WT alpha chain of F5

<400> SEQUENCE: 9

```
Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Phe Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80
```

```
Pro Ser Asp Ser Ala Thr Tyr Leu Cys Ala Val Asn Phe Gly Gly Gly
                85                  90                  95

Lys Leu Ile Phe Gly Gln Gly Thr Glu Leu Ser Val Lys Pro Asn Ile
            100                 105                 110

Gln Asn Pro Asp Pro Ala Val Tyr Gln Leu Arg Asp Ser Lys Ser Ser
        115                 120                 125

Asp Lys Ser Val Cys Leu Phe Thr Asp Phe Asp Ser Gln Thr Asn Val
    130                 135                 140

Ser Gln Ser Lys Asp Ser Asp Val Tyr Ile Thr Asp Lys Thr Val Leu
145                 150                 155                 160

Asp Met Arg Ser Met Asp Phe Lys Ser Asn Ser Ala Val Ala Trp Ser
                165                 170                 175

Asn Lys Ser Asp Phe Ala Cys Ala Asn Ala Phe Asn Asn Ser Ile Ile
            180                 185                 190

Pro Glu Asp Thr Phe Phe Pro Ser Pro Glu Ser Ser Cys Asp Val Lys
        195                 200                 205

Leu Val Glu Lys Ser Phe Glu Thr Asp Thr Asn Leu Asn Phe Gln Asn
    210                 215                 220

Leu Ser Val Ile Gly Phe Arg Ile Leu Leu Leu Lys Val Ala Gly Phe
225                 230                 235                 240

Asn Leu Leu Met Thr Leu Arg Leu Trp Ser Ser
                245                 250


<210> SEQ ID NO 10
<211> LENGTH: 287
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: AA of WT beta chain of F5

<400> SEQUENCE: 10

Ile Ala Gly Ile Thr Gln Ala Pro Thr Ser Gln Ile Leu Ala Ala Gly
1               5                   10                  15

Arg Arg Met Thr Leu Arg Cys Thr Gln Asp Met Arg His Asn Ala Met
            20                  25                  30

Tyr Trp Tyr Arg Gln Asp Leu Gly Leu Gly Leu Arg Leu Ile His Tyr
        35                  40                  45

Ser Asn Thr Ala Gly Thr Thr Gly Lys Gly Glu Val Pro Asp Gly Tyr
    50                  55                  60

Ser Val Ser Arg Ala Asn Thr Asp Asp Phe Pro Leu Thr Leu Ala Ser
65                  70                  75                  80

Ala Val Pro Ser Gln Thr Ser Val Tyr Phe Cys Ala Ser Ser Leu Ser
                85                  90                  95

Phe Gly Thr Glu Ala Phe Phe Gly Gln Gly Thr Arg Leu Thr Val Val
            100                 105                 110

Glu Asp Leu Asn Lys Val Phe Pro Pro Glu Val Ala Val Phe Glu Pro
        115                 120                 125

Ser Glu Ala Glu Ile Ser His Thr Gln Lys Ala Thr Leu Val Cys Leu
    130                 135                 140

Ala Thr Gly Phe Phe Pro Asp His Val Glu Leu Ser Trp Trp Val Asn
145                 150                 155                 160

Gly Lys Glu Val His Ser Gly Val Ser Thr Asp Pro Gln Pro Leu Lys
                165                 170                 175
```

```
Glu Gln Pro Ala Leu Asn Asp Ser Arg Tyr Cys Leu Ser Ser Arg Leu
            180                 185                 190

Arg Val Ser Ala Thr Phe Trp Gln Asn Pro Arg Asn His Phe Arg Cys
        195                 200                 205

Gln Val Gln Phe Tyr Gly Leu Ser Glu Asn Asp Glu Trp Thr Gln Asp
    210                 215                 220

Arg Ala Lys Pro Val Thr Gln Ile Val Ser Ala Glu Ala Trp Gly Arg
225                 230                 235                 240

Ala Cys Gly Phe Thr Ser Ser Tyr Gln Gln Gly Val Leu Ser Ala Thr
                245                 250                 255

Ile Leu Tyr Glu Ile Leu Leu Gly Lys Ala Thr Leu Tyr Ala Val Leu
            260                 265                 270

Val Ser Ala Leu Val Leu Met Ala Met Val Lys Arg Lys Asp Phe
        275                 280                 285


<210> SEQ ID NO 11
<211> LENGTH: 250
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: AA of WT alpha chain of F4

<400> SEQUENCE: 11

Gly Gln Gln Leu Asn Gln Ser Pro Gln Ser Met Phe Ile Gln Glu Gly
1               5                   10                  15

Glu Asp Val Ser Met Asn Cys Thr Ser Ser Ser Ile Phe Asn Thr Trp
            20                  25                  30

Leu Trp Tyr Lys Gln Asp Pro Gly Glu Gly Pro Val Leu Leu Ile Ala
        35                  40                  45

Leu Tyr Lys Ala Gly Glu Leu Thr Ser Asn Gly Arg Leu Thr Ala Gln
    50                  55                  60

Phe Gly Ile Thr Arg Lys Asp Ser Phe Leu Asn Ile Ser Ala Ser Ile
65                  70                  75                  80

Pro Ser Asp Val Gly Ile Tyr Phe Cys Ala Gly Gly Thr Gly Asn Gln
                85                  90                  95

Phe Tyr Phe Gly Thr Gly Thr Ser Leu Thr Val Ile Pro Asn Ile Gln
            100                 105                 110

Asn Pro Asp Pro Ala Val Tyr Gln Leu Arg Asp Ser Lys Ser Ser Asp
        115                 120                 125

Lys Ser Val Cys Leu Phe Thr Asp Phe Asp Ser Gln Thr Asn Val Ser
    130                 135                 140

Gln Ser Lys Asp Ser Asp Val Tyr Ile Thr Asp Lys Thr Val Leu Asp
145                 150                 155                 160

Met Arg Ser Met Asp Phe Lys Ser Asn Ser Ala Val Ala Trp Ser Asn
                165                 170                 175

Lys Ser Asp Phe Ala Cys Ala Asn Ala Phe Asn Asn Ser Ile Ile Pro
            180                 185                 190

Glu Asp Thr Phe Phe Pro Ser Pro Glu Ser Ser Cys Asp Val Lys Leu
        195                 200                 205

Val Glu Lys Ser Phe Glu Thr Asp Thr Asn Leu Asn Phe Gln Asn Leu
    210                 215                 220

Ser Val Ile Gly Phe Arg Ile Leu Leu Leu Lys Val Ala Gly Phe Asn
225                 230                 235                 240
```

```
Leu Leu Met Thr Leu Arg Leu Trp Ser Ser
                245                 250


<210> SEQ ID NO 12
<211> LENGTH: 288
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: AA of WT beta chain of F4

<400> SEQUENCE: 12

Asp Ala Gly Ile Thr Gln Ser Pro Arg His Lys Val Thr Glu Thr Gly
1               5                   10                  15

Thr Pro Val Thr Leu Arg Cys His Gln Thr Glu Asn His Arg Tyr Met
            20                  25                  30

Tyr Trp Tyr Arg Gln Asp Pro Gly His Gly Leu Arg Leu Ile His Tyr
        35                  40                  45

Ser Tyr Gly Val Lys Asp Thr Asp Lys Gly Glu Val Ser Asp Gly Tyr
    50                  55                  60

Ser Val Ser Arg Ser Lys Thr Glu Asp Phe Leu Leu Thr Leu Glu Ser
65                  70                  75                  80

Ala Thr Ser Ser Gln Thr Ser Val Tyr Phe Cys Ala Ile Ser Glu Val
                85                  90                  95

Gly Val Gly Gln Pro Gln His Phe Gly Asp Gly Thr Arg Leu Ser Ile
            100                 105                 110

Leu Glu Asp Leu Asn Lys Val Phe Pro Pro Glu Val Ala Val Phe Glu
        115                 120                 125

Pro Ser Glu Ala Glu Ile Ser His Thr Gln Lys Ala Thr Leu Val Cys
    130                 135                 140

Leu Ala Thr Gly Phe Phe Pro Asp His Val Glu Leu Ser Trp Trp Val
145                 150                 155                 160

Asn Gly Lys Glu Val His Ser Gly Val Ser Thr Asp Pro Gln Pro Leu
                165                 170                 175

Lys Glu Gln Pro Ala Leu Asn Asp Ser Arg Tyr Cys Leu Ser Ser Arg
            180                 185                 190

Leu Arg Val Ser Ala Thr Phe Trp Gln Asn Pro Arg Asn His Phe Arg
        195                 200                 205

Cys Gln Val Gln Phe Tyr Gly Leu Ser Glu Asn Asp Glu Trp Thr Gln
    210                 215                 220

Asp Arg Ala Lys Pro Val Thr Gln Ile Val Ser Ala Glu Ala Trp Gly
225                 230                 235                 240

Arg Ala Cys Gly Phe Thr Ser Ser Tyr Gln Gln Gly Val Leu Ser Ala
                245                 250                 255

Thr Ile Leu Tyr Glu Ile Leu Leu Gly Lys Ala Thr Leu Tyr Ala Val
            260                 265                 270

Leu Val Ser Ala Leu Val Leu Met Ala Met Val Lys Arg Lys Asp Phe
        275                 280                 285


<210> SEQ ID NO 13
<211> LENGTH: 112
<212> TYPE: PRT
<213> ORGANISM: Artificial Sequence
<220> FEATURE:
<223> OTHER INFORMATION: Synthetic
<220> FEATURE:
<221> NAME/KEY: misc_feature
```

<223> OTHER INFORMATION: AA of variable region of beta chain of F5 mut5

<400> SEQUENCE: 13

Ile Ala Gly Ile Thr Gln Ala Pro Thr Ser Gln Ile Leu Ala Ala Gly
1 5 10 15

Arg Arg Met Thr Leu Arg Cys Thr Gln Asp Met Arg His Asn Ala Met
20 25 30

Tyr Trp Tyr Arg Gln Asp Leu Gly Leu Gly Leu Arg Leu Ile His Tyr
35 40 45

Ser Asn Val Met Gly Ala Thr Gly Lys Gly Glu Val Pro Asp Gly Tyr
50 55 60

Ser Val Ser Arg Ala Asn Thr Asp Asp Phe Pro Leu Thr Leu Ala Ser
65 70 75 80

Ala Val Pro Ser Gln Thr Ser Val Tyr Phe Cys Ala Ser Ser Leu Ser
85 90 95

Phe Gly Thr Glu Ala Phe Phe Gly Gln Gly Thr Arg Leu Thr Val Val
100 105 110

<210> SEQ ID NO 14
<211> LENGTH: 292
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: AA of full length beta chain of 1G4 mut 1

<400> SEQUENCE: 14

Asn Ala Gly Val Thr Gln Thr Pro Lys Phe Gln Val Leu Lys Thr Gly
1 5 10 15

Gln Ser Met Thr Leu Gln Cys Ala Gln Asp Met Asn His Glu Tyr Met
20 25 30

Ser Trp Tyr Arg Gln Asp Pro Gly Met Gly Leu Arg Leu Ile His Tyr
35 40 45

Ser Val Ala Ala Gly Ile Thr Asp Gln Gly Glu Val Pro Asn Gly Tyr
50 55 60

Asn Val Ser Arg Ser Thr Thr Glu Asp Phe Pro Leu Arg Leu Leu Ser
65 70 75 80

Ala Ala Pro Ser Gln Thr Ser Val Tyr Phe Cys Ala Ser Ser Tyr Val
85 90 95

Gly Asn Thr Gly Glu Leu Phe Phe Gly Glu Gly Ser Arg Leu Thr Val
100 105 110

Leu Glu Asp Leu Lys Asn Val Phe Pro Pro Glu Val Ala Val Phe Glu
115 120 125

Pro Ser Glu Ala Glu Ile Ser His Thr Gln Lys Ala Thr Leu Val Cys
130 135 140

Leu Ala Thr Gly Phe Tyr Pro Asp His Val Glu Leu Ser Trp Trp Val
145 150 155 160

Asn Gly Lys Glu Val His Ser Gly Val Ser Thr Asp Pro Gln Pro Leu
165 170 175

Lys Glu Gln Pro Ala Leu Asn Asp Ser Arg Tyr Ser Leu Ser Ser Arg
180 185 190

Leu Arg Val Ser Ala Thr Phe Trp Gln Asn Pro Arg Asn His Phe Arg
195 200 205

Cys Gln Val Gln Phe Tyr Gly Leu Ser Glu Asn Asp Glu Trp Thr Gln
210 215 220

```
Asp Arg Ala Lys Pro Val Thr Gln Ile Val Ser Ala Glu Ala Trp Gly
225                 230                 235                 240

Arg Ala Asp Cys Gly Phe Thr Ser Glu Ser Tyr Gln Gln Gly Val Leu
                245                 250                 255

Ser Ala Thr Ile Leu Tyr Glu Ile Leu Leu Gly Lys Ala Thr Leu Tyr
            260                 265                 270

Ala Val Leu Val Ser Ala Leu Val Leu Met Ala Met Val Lys Arg Lys
        275                 280                 285

Asp Ser Arg Gly
    290


<210> SEQ ID NO 15
<211> LENGTH: 292
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: AA of full length beta chain of 1G4 mut 2

<400> SEQUENCE: 15

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ser Trp Tyr Arg Gln Asp Pro Gly Met Gly Leu Arg Leu Ile His Tyr
        35                  40                  45

Ser Val Gly Ile Gly Ile Thr Asp Gln Gly Glu Val Pro Asn Gly Tyr
    50                  55                  60

Asn Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Ser Tyr Val
                85                  90                  95

Gly Asn Thr Gly Glu Leu Phe Phe Gly Glu Gly Ser Arg Leu Thr Val
            100                 105                 110

Leu Glu Asp Leu Lys Asn Val Phe Pro Pro Glu Val Ala Val Phe Glu
        115                 120                 125

Pro Ser Glu Ala Glu Ile Ser His Thr Gln Lys Ala Thr Leu Val Cys
    130                 135                 140

Leu Ala Thr Gly Phe Tyr Pro Asp His Val Glu Leu Ser Trp Trp Val
145                 150                 155                 160

Asn Gly Lys Glu Val His Ser Gly Val Ser Thr Asp Pro Gln Pro Leu
                165                 170                 175

Lys Glu Gln Pro Ala Leu Asn Asp Ser Arg Tyr Ser Leu Ser Ser Arg
            180                 185                 190

Leu Arg Val Ser Ala Thr Phe Trp Gln Asn Pro Arg Asn His Phe Arg
        195                 200                 205

Cys Gln Val Gln Phe Tyr Gly Leu Ser Glu Asn Asp Glu Trp Thr Gln
    210                 215                 220

Asp Arg Ala Lys Pro Val Thr Gln Ile Val Ser Ala Glu Ala Trp Gly
225                 230                 235                 240

Arg Ala Asp Cys Gly Phe Thr Ser Glu Ser Tyr Gln Gln Gly Val Leu
                245                 250                 255

Ser Ala Thr Ile Leu Tyr Glu Ile Leu Leu Gly Lys Ala Thr Leu Tyr
            260                 265                 270
```

```
Ala Val Leu Val Ser Ala Leu Val Leu Met Ala Met Val Lys Arg Lys
        275                 280                 285

Asp Ser Arg Gly
    290


<210> SEQ ID NO 16
<211> LENGTH: 292
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: AA of full length beta chain of 1G4 mut 3

<400> SEQUENCE: 16

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ser Trp Tyr Arg Gln Asp Pro Gly Met Gly Leu Arg Leu Ile His Tyr
        35                  40                  45

Ser Val Ala Ile Gly Ile Thr Asp Gln Gly Glu Val Pro Asn Gly Tyr
    50                  55                  60

Asn Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Ser Tyr Val
                85                  90                  95

Gly Asn Thr Gly Glu Leu Phe Phe Gly Glu Gly Ser Arg Leu Thr Val
            100                 105                 110

Leu Glu Asp Leu Lys Asn Val Phe Pro Pro Glu Val Ala Val Phe Glu
        115                 120                 125

Pro Ser Glu Ala Glu Ile Ser His Thr Gln Lys Ala Thr Leu Val Cys
    130                 135                 140

Leu Ala Thr Gly Phe Tyr Pro Asp His Val Glu Leu Ser Trp Trp Val
145                 150                 155                 160

Asn Gly Lys Glu Val His Ser Gly Val Ser Thr Asp Pro Gln Pro Leu
                165                 170                 175

Lys Glu Gln Pro Ala Leu Asn Asp Ser Arg Tyr Ser Leu Ser Ser Arg
            180                 185                 190

Leu Arg Val Ser Ala Thr Phe Trp Gln Asn Pro Arg Asn His Phe Arg
        195                 200                 205

Cys Gln Val Gln Phe Tyr Gly Leu Ser Glu Asn Asp Glu Trp Thr Gln
    210                 215                 220

Asp Arg Ala Lys Pro Val Thr Gln Ile Val Ser Ala Glu Ala Trp Gly
225                 230                 235                 240

Arg Ala Asp Cys Gly Phe Thr Ser Glu Ser Tyr Gln Gln Gly Val Leu
                245                 250                 255

Ser Ala Thr Ile Leu Tyr Glu Ile Leu Leu Gly Lys Ala Thr Leu Tyr
            260                 265                 270

Ala Val Leu Val Ser Ala Leu Val Leu Met Ala Met Val Lys Arg Lys
        275                 280                 285

Asp Ser Arg Gly
    290


<210> SEQ ID NO 17
```

<211> LENGTH: 287
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: AA of full length beta chain of F5 mut 1

<400> SEQUENCE: 17

```
Ile Ala Gly Ile Thr Gln Ala Pro Thr Ser Gln Ile Leu Ala Ala Gly
1               5                   10                  15

Arg Arg Met Thr Leu Arg Cys Thr Gln Asp Met Arg His Asn Ala Met
            20                  25                  30

Tyr Trp Tyr Arg Gln Asp Leu Gly Leu Gly Leu Arg Leu Ile His Tyr
        35                  40                  45

Ser Asn Thr Ala Gly Ala Thr Gly Lys Gly Glu Val Pro Asp Gly Tyr
    50                  55                  60

Ser Val Ser Arg Ala Asn Thr Asp Asp Phe Pro Leu Thr Leu Ala Ser
65                  70                  75                  80

Ala Val Pro Ser Gln Thr Ser Val Tyr Phe Cys Ala Ser Ser Leu Ser
                85                  90                  95

Phe Gly Thr Glu Ala Phe Phe Gly Gln Gly Thr Arg Leu Thr Val Val
            100                 105                 110

Glu Asp Leu Asn Lys Val Phe Pro Pro Glu Val Ala Val Phe Glu Pro
        115                 120                 125

Ser Glu Ala Glu Ile Ser His Thr Gln Lys Ala Thr Leu Val Cys Leu
    130                 135                 140

Ala Thr Gly Phe Phe Pro Asp His Val Glu Leu Ser Trp Trp Val Asn
145                 150                 155                 160

Gly Lys Glu Val His Ser Gly Val Ser Thr Asp Pro Gln Pro Leu Lys
                165                 170                 175

Glu Gln Pro Ala Leu Asn Asp Ser Arg Tyr Cys Leu Ser Ser Arg Leu
            180                 185                 190

Arg Val Ser Ala Thr Phe Trp Gln Asn Pro Arg Asn His Phe Arg Cys
        195                 200                 205

Gln Val Gln Phe Tyr Gly Leu Ser Glu Asn Asp Glu Trp Thr Gln Asp
    210                 215                 220

Arg Ala Lys Pro Val Thr Gln Ile Val Ser Ala Glu Ala Trp Gly Arg
225                 230                 235                 240

Ala Cys Gly Phe Thr Ser Ser Tyr Gln Gln Gly Val Leu Ser Ala Thr
                245                 250                 255

Ile Leu Tyr Glu Ile Leu Leu Gly Lys Ala Thr Leu Tyr Ala Val Leu
            260                 265                 270

Val Ser Ala Leu Val Leu Met Ala Met Val Lys Arg Lys Asp Phe
        275                 280                 285
```

<210> SEQ ID NO 18
<211> LENGTH: 288
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: AA of full length beta chain of F4 mut 1

<400> SEQUENCE: 18

```
Asp Ala Gly Ile Thr Gln Ser Pro Arg His Lys Val Thr Glu Thr Gly
```

-continued

```
1               5                   10                  15

Thr Pro Val Thr Leu Arg Cys His Gln Thr Glu Asn His Arg Tyr Met
            20                  25                  30

Tyr Trp Tyr Arg Gln Asp Pro Gly His Gly Leu Arg Leu Ile His Tyr
        35                  40                  45

Ser Tyr Ala Val Lys Asp Thr Asp Lys Gly Glu Val Ser Asp Gly Tyr
    50                  55                  60

Ser Val Ser Arg Ser Lys Thr Glu Asp Phe Leu Leu Thr Leu Glu Ser
65                  70                  75                  80

Ala Thr Ser Ser Gln Thr Ser Val Tyr Phe Cys Ala Ile Ser Glu Val
                85                  90                  95

Gly Val Gly Gln Pro Gln His Phe Gly Asp Gly Thr Arg Leu Ser Ile
            100                 105                 110

Leu Glu Asp Leu Asn Lys Val Phe Pro Pro Glu Val Ala Val Phe Glu
        115                 120                 125

Pro Ser Glu Ala Glu Ile Ser His Thr Gln Lys Ala Thr Leu Val Cys
    130                 135                 140

Leu Ala Thr Gly Phe Phe Pro Asp His Val Glu Leu Ser Trp Trp Val
145                 150                 155                 160

Asn Gly Lys Glu Val His Ser Gly Val Ser Thr Asp Pro Gln Pro Leu
                165                 170                 175

Lys Glu Gln Pro Ala Leu Asn Asp Ser Arg Tyr Cys Leu Ser Ser Arg
            180                 185                 190

Leu Arg Val Ser Ala Thr Phe Trp Gln Asn Pro Arg Asn His Phe Arg
        195                 200                 205

Cys Gln Val Gln Phe Tyr Gly Leu Ser Glu Asn Asp Glu Trp Thr Gln
    210                 215                 220

Asp Arg Ala Lys Pro Val Thr Gln Ile Val Ser Ala Glu Ala Trp Gly
225                 230                 235                 240

Arg Ala Cys Gly Phe Thr Ser Ser Tyr Gln Gln Gly Val Leu Ser Ala
                245                 250                 255

Thr Ile Leu Tyr Glu Ile Leu Leu Gly Lys Ala Thr Leu Tyr Ala Val
            260                 265                 270

Leu Val Ser Ala Leu Val Leu Met Ala Met Val Lys Arg Lys Asp Phe
        275                 280                 285


<210> SEQ ID NO 19
<211> LENGTH: 288
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: AA of full length beta chain of F4 mut 2

<400> SEQUENCE: 19

Asp Ala Gly Ile Thr Gln Ser Pro Arg His Lys Val Thr Glu Thr Gly
1               5                   10                  15

Thr Pro Val Thr Leu Arg Cys His Gln Thr Glu Asn His Arg Tyr Met
            20                  25                  30

Tyr Trp Tyr Arg Gln Asp Pro Gly His Gly Leu Arg Leu Ile His Tyr
        35                  40                  45

Ser Tyr Ala Ala Lys Asp Thr Asp Lys Gly Glu Val Ser Asp Gly Tyr
    50                  55                  60

Ser Val Ser Arg Ser Lys Thr Glu Asp Phe Leu Leu Thr Leu Glu Ser
```

-continued

```
65                  70                  75                  80

Ala Thr Ser Ser Gln Thr Ser Val Tyr Phe Cys Ala Ile Ser Glu Val
                85                  90                  95

Gly Val Gly Gln Pro Gln His Phe Gly Asp Gly Thr Arg Leu Ser Ile
            100                 105                 110

Leu Glu Asp Leu Asn Lys Val Phe Pro Pro Glu Val Ala Val Phe Glu
        115                 120                 125

Pro Ser Glu Ala Glu Ile Ser His Thr Gln Lys Ala Thr Leu Val Cys
    130                 135                 140

Leu Ala Thr Gly Phe Phe Pro Asp His Val Glu Leu Ser Trp Trp Val
145                 150                 155                 160

Asn Gly Lys Glu Val His Ser Gly Val Ser Thr Asp Pro Gln Pro Leu
                165                 170                 175

Lys Glu Gln Pro Ala Leu Asn Asp Ser Arg Tyr Cys Leu Ser Ser Arg
            180                 185                 190

Leu Arg Val Ser Ala Thr Phe Trp Gln Asn Pro Arg Asn His Phe Arg
        195                 200                 205

Cys Gln Val Gln Phe Tyr Gly Leu Ser Glu Asn Asp Glu Trp Thr Gln
    210                 215                 220

Asp Arg Ala Lys Pro Val Thr Gln Ile Val Ser Ala Glu Ala Trp Gly
225                 230                 235                 240

Arg Ala Cys Gly Phe Thr Ser Ser Tyr Gln Gln Gly Val Leu Ser Ala
                245                 250                 255

Thr Ile Leu Tyr Glu Ile Leu Leu Gly Lys Ala Thr Leu Tyr Ala Val
            260                 265                 270

Leu Val Ser Ala Leu Val Leu Met Ala Met Val Lys Arg Lys Asp Phe
        275                 280                 285


<210> SEQ ID NO 20
<211> LENGTH: 287
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: AA of full length of beta chain of F5 mut5

<400> SEQUENCE: 20

Ile Ala Gly Ile Thr Gln Ala Pro Thr Ser Gln Ile Leu Ala Ala Gly
1               5                   10                  15

Arg Arg Met Thr Leu Arg Cys Thr Gln Asp Met Arg His Asn Ala Met
            20                  25                  30

Tyr Trp Tyr Arg Gln Asp Leu Gly Leu Gly Leu Arg Leu Ile His Tyr
        35                  40                  45

Ser Asn Val Met Gly Ala Thr Gly Lys Gly Glu Val Pro Asp Gly Tyr
    50                  55                  60

Ser Val Ser Arg Ala Asn Thr Asp Asp Phe Pro Leu Thr Leu Ala Ser
65                  70                  75                  80

Ala Val Pro Ser Gln Thr Ser Val Tyr Phe Cys Ala Ser Ser Leu Ser
                85                  90                  95

Phe Gly Thr Glu Ala Phe Phe Gly Gln Gly Thr Arg Leu Thr Val Val
            100                 105                 110

Glu Asp Leu Asn Lys Val Phe Pro Pro Glu Val Ala Val Phe Glu Pro
        115                 120                 125

Ser Glu Ala Glu Ile Ser His Thr Gln Lys Ala Thr Leu Val Cys Leu
```

```
    130                 135                 140

Ala Thr Gly Phe Phe Pro Asp His Val Glu Leu Ser Trp Trp Val Asn
145                 150                 155                 160

Gly Lys Glu Val His Ser Gly Val Ser Thr Asp Pro Gln Pro Leu Lys
                165                 170                 175

Glu Gln Pro Ala Leu Asn Asp Ser Arg Tyr Cys Leu Ser Ser Arg Leu
            180                 185                 190

Arg Val Ser Ala Thr Phe Trp Gln Asn Pro Arg Asn His Phe Arg Cys
        195                 200                 205

Gln Val Gln Phe Tyr Gly Leu Ser Glu Asn Asp Glu Trp Thr Gln Asp
    210                 215                 220

Arg Ala Lys Pro Val Thr Gln Ile Val Ser Ala Glu Ala Trp Gly Arg
225                 230                 235                 240

Ala Cys Gly Phe Thr Ser Ser Tyr Gln Gln Gly Val Leu Ser Ala Thr
                245                 250                 255

Ile Leu Tyr Glu Ile Leu Leu Gly Lys Ala Thr Leu Tyr Ala Val Leu
            260                 265                 270

Val Ser Ala Leu Val Leu Met Ala Met Val Lys Arg Lys Asp Phe
        275                 280                 285


<210> SEQ ID NO 21
<211> LENGTH: 933
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: NT of beta chain of WT 1G4

<400> SEQUENCE: 21

atgagcatcg gcctcctgtg ctgtgcagcc ttgtctctcc tgtgggcagg tccagtgaat      60

gctggtgtca ctcagacccc aaaattccag gtcctgaaga caggacagag catgacactg     120

cagtgtgccc aggatatgaa ccatgaatac atgtcctggt atcgacaaga cccaggcatg     180

gggctgaggc tgattcatta ctcagttggt gctggtatca ctgaccaagg agaagtcccc     240

aatggctaca atgtctccag atcaaccaca gaggatttcc cgctcaggct gctgtcggct     300

gctccctccc agacatctgt gtacttctgt gccagcagtt acgtcgggaa caccggggag     360

ctgttttttg gagaaggctc taggctgacc gtactggagg acctgaaaaa cgtgttccca     420

cccgaggtcg ctgtgtttga gccatcagaa gcagagatct cccacaccca aaaggccaca     480

ctggtgtgcc tggccacagg cttctacccc gaccacgtgg agctgagctg gtgggtgaat     540

gggaaggagg tgcacagtgg ggtcagcaca gacccgcagc ccctcaagga gcagcccgcc     600

ctcaatgact ccagatacag cctgagcagc cgcctgaggg tctcggccac cttctggcag     660

aacccccgca accacttccg ctgtcaagtc cagttctacg ggctctcgga gaatgacgag     720

tggacccagg atagggccaa acctgtcacc cagatcgtca gcgccgaggc ctggggtaga     780

gcagactgtg gcttcacctc cgagtcttac cagcaagggg tcctgtctgc caccatcctc     840

tatgagatct tgctagggaa ggccaccttg tatgccgtgc tggtcagtgc cctcgtgctg     900

atggccatgg tcaagagaaa ggattccaga ggc                                  933


<210> SEQ ID NO 22
<211> LENGTH: 933
<212> TYPE: DNA
<213> ORGANISM: Artificial Sequence
```

<220> FEATURE:
<223> OTHER INFORMATION: Synthetic
<220> FEATURE:
<221> NAME/KEY: misc_feature
<223> OTHER INFORMATION: NT of beta chain of 1G4 mut 1

<400> SEQUENCE: 22
atgagcatcg gcctcctgtg ctgtgcagcc ttgtctctcc tgtgggcagg tccagtgaat 60
gctggtgtca ctcagacccc aaaattccag gtcctgaaga caggacagag catgacactg 120
cagtgtgccc aggatatgaa ccatgaatac atgtcctggt atcgacaaga cccaggcatg 180
gggctgaggc tgattcatta ctcagttgcc gctggtatca ctgaccaagg agaagtcccc 240
aatggctaca atgtctccag atcaaccaca gaggatttcc cgctcaggct gctgtcggct 300
gctccctccc agacatctgt gtacttctgt gccagcagtt acgtcgggaa caccggggag 360 ctgtttttttg gagaaggctc taggctgacc gtactggagg acctgaaaaa cgtgttccca 420
cccgaggtcg ctgtgtttga gccatcagaa gcagagatct cccacaccca aaaggccaca 480
ctggtgtgcc tggccacagg cttctacccc gaccacgtgg agctgagctg gtgggtgaat 540
gggaaggagg tgcacagtgg ggtcagcaca gacccgcagc ccctcaagga gcagcccgcc 600
ctcaatgact ccagatacag cctgagcagc cgcctgaggg tctcggccac cttctggcag 660
aacccccgca accacttccg ctgtcaagtc cagttctacg ggctctcgga gaatgacgag 720
tggacccagg atagggccaa acctgtcacc cagatcgtca gcgccgaggc ctggggtaga 780
gcagactgtg gcttcacctc cgagtcttac cagcaagggg tcctgtctgc caccatcctc 840
tatgagatct tgctagggaa ggccaccttg tatgccgtgc tggtcagtgc cctcgtgctg 900
atggccatgg tcaagagaaa ggattccaga ggc 933

<210> SEQ ID NO 23
<211> LENGTH: 933
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: NT of beta chain of 1G4 mut 2

<400> SEQUENCE: 23
atgagcatcg gcctcctgtg ctgtgcagcc ttgtctctcc tgtgggcagg tccagtgaat 60
gctggtgtca ctcagacccc aaaattccag gtcctgaaga caggacagag catgacactg 120
cagtgtgccc aggatatgaa ccatgaatac atgtcctggt atcgacaaga cccaggcatg 180
gggctgaggc tgattcatta ctcagttggt atcggtatca ctgaccaagg agaagtcccc 240
aatggctaca atgtctccag atcaaccaca gaggatttcc cgctcaggct gctgtcggct 300
gctccctccc agacatctgt gtacttctgt gccagcagtt acgtcgggaa caccggggag 360 ctgtttttttg gagaaggctc taggctgacc gtactggagg acctgaaaaa cgtgttccca 420
cccgaggtcg ctgtgtttga gccatcagaa gcagagatct cccacaccca aaaggccaca 480
ctggtgtgcc tggccacagg cttctacccc gaccacgtgg agctgagctg gtgggtgaat 540
gggaaggagg tgcacagtgg ggtcagcaca gacccgcagc ccctcaagga gcagcccgcc 600
ctcaatgact ccagatacag cctgagcagc cgcctgaggg tctcggccac cttctggcag 660
aacccccgca accacttccg ctgtcaagtc cagttctacg ggctctcgga gaatgacgag 720
tggacccagg atagggccaa acctgtcacc cagatcgtca gcgccgaggc ctggggtaga 780
gcagactgtg gcttcacctc cgagtcttac cagcaagggg tcctgtctgc caccatcctc 840
tatgagatct tgctagggaa ggccaccttg tatgccgtgc tggtcagtgc cctcgtgctg 900
atggccatgg tcaagagaaa ggattccaga ggc 933

<210> SEQ ID NO 24
<211> LENGTH: 933
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: NT of beta chain of 1G4 mut3

<400> SEQUENCE: 24
atgagcatcg gcctcctgtg ctgtgcagcc ttgtctctcc tgtgggcagg tccagtgaat 60
gctggtgtca ctcagacccc aaaattccag gtcctgaaga caggacagag catgacactg 120
cagtgtgccc aggatatgaa ccatgaatac atgtcctggt atcgacaaga cccaggcatg 180
gggctgaggc tgattcatta ctcagttgcc atcggtatca ctgaccaagg agaagtcccc 240
aatggctaca atgtctccag atcaaccaca gaggatttcc cgctcaggct gctgtcggct 300
gctccctccc agacatctgt gtacttctgt gccagcagtt acgtcgggaa caccggggag 360 ctgtttttg gagaaggctc taggctgacc gtactggagg acctgaaaaa cgtgttccca 420
cccgaggtcg ctgtgtttga gccatcagaa gcagagatct cccacaccca aaaggccaca 480
ctggtgtgcc tggccacagg cttctacccc gaccacgtgg agctgagctg gtgggtgaat 540
gggaaggagg tgcacagtgg ggtcagcaca gacccgcagc ccctcaagga gcagcccgcc 600
ctcaatgact ccagatacag cctgagcagc cgcctgaggg tctcggccac cttctggcag 660
aacccccgca accacttccg ctgtcaagtc cagttctacg ggctctcgga gaatgacgag 720
tggacccagg atagggccaa acctgtcacc cagatcgtca gcgccgaggc ctggggtaga 780
gcagactgtg gcttcacctc cgagtcttac cagcaagggg tcctgtctgc caccatcctc 840
tatgagatct tgctagggaa ggccaccttg tatgccgtgc tggtcagtgc cctcgtgctg 900
atggccatgg tcaagagaaa ggattccaga ggc 933

<210> SEQ ID NO 25
<211> LENGTH: 822
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: NT of alpha chain of WT 1G4 TCR

<400> SEQUENCE: 25
atggagaccc tcttgggcct gcttatcctt tggctgcagc tgcaatgggt gagcagcaaa 60
caggaggtga cgcagattcc tgcagctctg agtgtcccag aaggagaaaa cttggttctc 120
aactgcagtt tcactgatag cgctatttac aacctccagt ggtttaggca ggaccctggg 180
aaaggtctca catctctgtt gcttattcag tcaagtcaga gagagcaaac aagtggaaga 240
cttaatgcct cgctggataa atcatcagga cgtagtactt tatacattgc agcttctcag 300
cctggtgact cagccaccta cctctgtgct gtgaggccca catcaggagg aagctacata 360
cctacatttg gaagaggaac cagccttatt gttcatccgt atatccagaa ccctgaccct 420
gccgtgtacc agctgagaga ctctaaatcc agtgacaagt ctgtctgcct attcaccgat 480
tttgattctc aaacaaatgt gtcacaaagt aaggattctg atgtgtatat cacagacaaa 540
actgtgctag acatgaggtc tatggacttc aagagcaaca gtgctgtggc ctggagcaac 600
aaatctgact ttgcatgtgc aaacgccttc aacaacagca ttattccaga agacaccttc 660
ttccccagcc cagaaagttc ctgtgatgtc aagctggtcg agaaaagctt tgaaacagat 720
acgaacctaa actttcaaaa cctgtcagtg attgggttcc gaatcctcct cctgaaagtg 780
gccgggttta atctgctcat gacgctgcgg ctgtggtcca gc 822

<210> SEQ ID NO 26
<211> LENGTH: 804
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: NT of alpha chain of WT F4

<400> SEQUENCE: 26
atgttgcttg aacatttatt aataatcttg tggatgcagc tgacatgggt cagtggtcaa 60
cagctgaatc agagtcctca atctatgttt atccaggaag gagaagatgt ctccatgaac 120
tgcacttctt caagcatatt taacacctgg ctatggtaca agcaggaccc tggggaaggt 180
cctgtcctct tgatagcctt atataaggct ggtgaattga cctcaaatgg aagactgact 240
gctcagtttg gtataaccag aaaggacagc ttcctgaata tctcagcatc catacctagt 300
gatgtaggca tctacttctg tgctggtggg accggtaacc agttctattt tgggacaggg 360
acaagtttga cggtcattcc aaatatccag aaccctgacc ctgccgtgta ccagctgaga 420
gactctaaat ccagtgacaa gtctgtctgc ctattcaccg attttgattc tcaaacaaat 480
gtgtcacaaa gtaaggattc tgatgtgtat atcacagaca aaactgtgct agacatgagg 540
tctatggact tcaagagcaa cagtgctgtg gcctggagca acaaatctga ctttgcatgt 600
gcaaacgcct tcaacaacag cattattcca gaagacacct tcttccccag cccagaaagt 660
tcctgtgatg tcaagctggt cgagaaaagc tttgaaacag atacgaacct aaactttcaa 720
aacctgtcag tgattgggtt ccgaatcctc ctcctgaagg tggccgggtt taatctgctc 780
atgacgctgc ggctgtggtc cagc 804

<210> SEQ ID NO 27
<211> LENGTH: 921
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: NT of beta chain of WT F4

<400> SEQUENCE: 27
atgggcacaa ggttgttctt ctatgtggcc ctttgtctcc tgtggacagg acacatggat 60
gctggaatca cccagagccc aagacacaag gtcacagaga caggaacacc agtgactctg 120
agatgtcacc agactgagaa ccaccgctat atgtactggt atcgacaaga cccggggcat 180
gggctgaggc tgatccatta ctcatatggt gttaaagata ctgacaaagg agaagtctca 240
gatggctata gtgtctctag atcaaagaca gaggatttcc tcctcactct ggagtccgct 300
accagctccc agacatctgt gtacttctgt gccatcagtg aggtaggggt tgggcagccc 360
cagcattttg gtgatgggac tcgactctcc atcctagagg acctgaacaa ggtgttccca 420
cccgaggtcg ctgtgtttga gccatcagaa gcagagatct cccacaccca aaaggccaca 480
ctggtgtgcc tggccacagg cttcttcccc gaccacgtgg agctgagctg gtgggtgaat 540
gggaaggagg tgcacagtgg ggtcagcacg gacccgcagc ccctcaagga gcagcccgcc 600
ctcaatgact ccagatactg cctgagcagc cgcctgaggg tctcggccac cttctggcag 660
aacccccgca accacttccg ctgtcaagtc cagttctacg ggctctcgga gaatgacgag 720
tggacccagg atagggccaa acccgtcacc cagatcgtca gcgccgaggc ctggggtaga 780
gcatgtggct ttacctcgtc ctaccagcaa ggggtcctgt ctgccaccat cctctatgag 840
atcctgctag ggaaggccac cctgtatgct gtgctggtca gcgcccttgt gttgatggcc 900
atggtcaaga gaaaggattt c 921

<210> SEQ ID NO 28
<211> LENGTH: 921
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: NT of beta chain of F4 mut 1

<400> SEQUENCE: 28
atgggcacaa ggttgttctt ctatgtggcc ctttgtctcc tgtggacagg acacatggat 60
gctggaatca cccagagccc aagacacaag gtcacagaga caggaacacc agtgactctg 120
agatgtcacc agactgagaa ccaccgctat atgtactggt atcgacaaga cccggggcat 180
gggctgaggc tgatccatta ctcatatgcc gttaaagata ctgacaaagg agaagtctca 240
gatggctata gtgtctctag atcaaagaca gaggatttcc tcctcactct ggagtccgct 300
accagctccc agacatctgt gtacttctgt gccatcagtg aggtaggggt tgggcagccc 360
cagcattttg gtgatgggac tcgactctcc atcctagagg acctgaacaa ggtgttccca 420
cccgaggtcg ctgtgtttga gccatcagaa gcagagatct cccacaccca aaaggccaca 480
ctggtgtgcc tggccacagg cttcttcccc gaccacgtgg agctgagctg gtgggtgaat 540
gggaaggagg tgcacagtgg ggtcagcacg gacccgcagc ccctcaagga gcagcccgcc 600
ctcaatgact ccagatactg cctgagcagc cgcctgaggg tctcggccac cttctggcag 660
aacccccgca accacttccg ctgtcaagtc cagttctacg ggctctcgga gaatgacgag 720
tggacccagg atagggccaa acccgtcacc cagatcgtca gcgccgaggc ctggggtaga 780
gcatgtggct ttacctcgtc ctaccagcaa ggggtcctgt ctgccaccat cctctatgag 840
atcctgctag ggaaggccac cctgtatgct gtgctggtca gcgcccttgt gttgatggcc 900
atggtcaaga gaaaggattt c 921

<210> SEQ ID NO 29
<211> LENGTH: 921
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: NT of beta chain of F4 mut 2

<400> SEQUENCE: 29
atgggcacaa ggttgttctt ctatgtggcc ctttgtctcc tgtggacagg acacatggat 60

```
gctggaatca cccagagccc aagacacaag gtcacagaga caggaacacc agtgactctg    120

agatgtcacc agactgagaa ccaccgctat atgtactggt atcgacaaga cccggggcat    180

gggctgaggc tgatccatta ctcatatgcc gccaaagata ctgacaaagg agaagtctca    240

gatggctata gtgtctctag atcaaagaca gaggatttcc tcctcactct ggagtccgct    300

accagctccc agacatctgt gtacttctgt gccatcagtg aggtaggggt tgggcagccc    360

cagcattttg gtgatgggac tcgactctcc atcctagagg acctgaacaa ggtgttccca    420

cccgaggtcg ctgtgtttga gccatcagaa gcagagatct cccacaccca aaaggccaca    480

ctggtgtgcc tggccacagg cttcttcccc gaccacgtgg agctgagctg gtgggtgaat    540

gggaaggagg tgcacagtgg ggtcagcacg gacccgcagc ccctcaagga gcagcccgcc    600

ctcaatgact ccagatactg cctgagcagc cgcctgaggg tctcggccac cttctggcag    660

aacccccgca accacttccg ctgtcaagtc cagttctacg ggctctcgga gaatgacgag    720

tggacccagg atagggccaa acccgtcacc cagatcgtca gcgccgaggc ctggggtaga    780

gcatgtggct ttacctcgtc ctaccagcaa ggggtcctgt ctgccaccat cctctatgag    840

atcctgctag ggaaggccac cctgtatgct gtgctggtca gcgcccttgt gttgatggcc    900

atggtcaaga gaaaggattt c                                              921
```

<210> SEQ ID NO 30
<211> LENGTH: 822
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: NT of alpha chain of WT F5

<400> SEQUENCE: 30

```
atgatgaaat ccttgagagt tttactagtg atcctgtggc ttcagttgag ctgggtttgg     60

agccaacaga aggaggtgga gcagaattct ggacccctca gtgttccaga gggagccatt    120

gcctctctca actgcactta cagtgaccga ggttcccagt ccttcttctg gtacagacaa    180

tattctggga aaagccctga gttgataatg ttcatatact ccaatggtga caaagaagat    240

ggaaggttta cagcacagct caataaagcc agccagtatg tttctctgct catcagagac    300

tcccagccca gtgattcagc cacctacctc tgtgccgtga acttcggagg aggaaagctt    360

atcttcggac agggaacgga gttatctgtg aaacccaata tccagaaccc tgaccctgcc    420

gtgtaccagc tgagagactc taaatccagt gacaagtctg tctgcctatt caccgatttt    480

gattctcaaa caaatgtgtc acaaagtaag gattctgatg tgtatatcac agacaaaact    540

gtgctagaca tgaggtctat ggacttcaag agcaacagtg ctgtggcctg gagcaacaaa    600

tctgactttg catgtgcaaa cgccttcaac aacagcatta ttccagaaga caccttcttc    660

cccagcccag aaagttcctg tgatgtcaag ctggtcgaga aaagctttga aacagatacg    720

aacctaaact ttcaaaacct gtcagtgatt gggttccgaa tcctcctcct gaaagtggcc    780

gggtttaatc tgctcatgac gctgcggctg tggtccagct ga                       822
```

<210> SEQ ID NO 31
<211> LENGTH: 918
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: NT of beta chain of WT F5

<400> SEQUENCE: 31
atgagaatca ggctcctgtg ctgtgtggcc ttttctctcc tgtgggcagg tccagtgatt 60
gctgggatca cccaggcacc aacatctcag atcctggcag caggacggcg catgacactg 120
agatgtaccc aggatatgag acataatgcc atgtactggt atagacaaga tctaggactg 180
gggctaaggc tcatccatta ttcaaatact gcaggtacca ctggcaaagg agaagtccct 240
gatggttata gtgtctccag agcaaacaca gatgatttcc ccctcacgtt ggcgtctgct 300
gtaccctctc agacatctgt gtacttctgt gccagcagcc taagtttcgg cactgaagct 360
ttctttggac aaggcaccag actcacagtt gtagaggacc tgaacaaggt gttcccaccc 420
gaggtcgctg tgtttgagcc atcagaagca gagatctccc acacccaaaa ggccacactg 480
gtgtgcctgg ccacaggctt cttccccgac cacgtggagc tgagctggtg ggtgaatggg 540
aaggaggtgc acagtggggt cagcacggac ccgcagcccc tcaaggagca gcccgccctc 600
aatgactcca gatactgcct gagcagccgc ctgagggtct cggccacctt ctggcagaac 660
ccccgcaacc acttccgctg tcaagtccag ttctacgggc tctcggagaa tgacgagtgg 720
acccaggata gggccaaacc cgtcacccag atcgtcagcg ccgaggcctg gggtagagca 780
tgtggcttta cctcgtccta ccagcaaggg gtcctgtctg ccaccatcct ctatgagatc 840
ctgctaggga aggccaccct gtatgctgtg ctggtcagcg cccttgtgtt gatggccatg 900
gtcaagagaa aggatttc 918

<210> SEQ ID NO 32
<211> LENGTH: 918
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: NT of beta chain of F5 mut1

<400> SEQUENCE: 32
atgagaatca ggctcctgtg ctgtgtggcc ttttctctcc tgtgggcagg tccagtgatt 60
gctgggatca cccaggcacc aacatctcag atcctggcag caggacggcg catgacactg 120
agatgtaccc aggatatgag acataatgcc atgtactggt atagacaaga tctaggactg 180
gggctaaggc tcatccatta ttcaaatact gcagccacca ctggcaaagg agaagtccct 240
gatggttata gtgtctccag agcaaacaca gatgatttcc ccctcacgtt ggcgtctgct 300
gtaccctctc agacatctgt gtacttctgt gccagcagcc taagtttcgg cactgaagct 360
ttctttggac aaggcaccag actcacagtt gtagaggacc tgaacaaggt gttcccaccc 420
gaggtcgctg tgtttgagcc atcagaagca gagatctccc acacccaaaa ggccacactg 480
gtgtgcctgg ccacaggctt cttccccgac cacgtggagc tgagctggtg ggtgaatggg 540
aaggaggtgc acagtggggt cagcacggac ccgcagcccc tcaaggagca gcccgccctc 600
aatgactcca gatactgcct gagcagccgc ctgagggtct cggccacctt ctggcagaac 660
ccccgcaacc acttccgctg tcaagtccag ttctacgggc tctcggagaa tgacgagtgg 720
acccaggata gggccaaacc cgtcacccag atcgtcagcg ccgaggcctg gggtagagca 780
tgtggcttta cctcgtccta ccagcaaggg gtcctgtctg ccaccatcct ctatgagatc 840

-continued

```
ctgctaggga aggccaccct gtatgctgtg ctggtcagcg cccttgtgtt gatggccatg    900

gtcaagagaa aggatttc                                                  918


<210> SEQ ID NO 33
<211> LENGTH: 918
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: NT of beta chain of F5 mut5

<400> SEQUENCE: 33

atgagaatca ggctcctgtg ctgtgtggcc ttttctctcc tgtgggcagg tccagtgatt     60

gctgggatca cccaggcacc aacatctcag atcctggcag caggacggcg catgacactg    120

agatgtaccc aggatatgag acataatgcc atgtactggt atagacaaga tctaggactg    180

gggctaaggc tcatccatta ttcaaatgtg atgggtgcca ctggcaaagg agaagtccct    240

gatggttata gtgtctccag agcaaacaca gatgatttcc ccctcacgtt ggcgtctgct    300

gtaccctctc agacatctgt gtacttctgt gccagcagcc taagtttcgg cactgaagct    360

ttctttggac aaggcaccag actcacagtt gtagaggacc tgaacaaggt gttcccaccc    420

gaggtcgctg tgtttgagcc atcagaagca gagatctccc acacccaaaa ggccacactg    480

gtgtgcctgg ccacaggctt cttccccgac cacgtggagc tgagctggtg ggtgaatggg    540

aaggaggtgc acagtggggt cagcacggac ccgcagcccc tcaaggagca gcccgccctc    600

aatgactcca gatactgcct gagcagccgc ctgagggtct cggccacctt ctggcagaac    660

ccccgcaacc acttccgctg tcaagtccag ttctacgggc tctcggagaa tgacgagtgg    720

acccaggata gggccaaacc cgtcacccag atcgtcagcg ccgaggcctg gggtagagca    780

tgtggcttta cctcgtccta ccagcaaggg gtcctgtctg ccaccatcct ctatgagatc    840

ctgctaggga aggccaccct gtatgctgtg ctggtcagcg cccttgtgtt gatggccatg    900

gtcaagagaa aggatttc                                                  918


<210> SEQ ID NO 34
<211> LENGTH: 918
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: NT of beta chain of F5mut4

<400> SEQUENCE: 34

atgagaatca ggctcctgtg ctgtgtggcc ttttctctcc tgtgggcagg tccagtgatt     60

gctgggatca cccaggcacc aacatctcag atcctggcag caggacggcg catgacactg    120

agatgtaccc aggatatgag acataatgcc atgtactggt atagacaaga tctaggactg    180

gggctaaggc tcatccatta ttcaaatact atgggtgcca ctggcaaagg agaagtccct    240

gatggttata gtgtctccag agcaaacaca gatgatttcc ccctcacgtt ggcgtctgct    300

gtaccctctc agacatctgt gtacttctgt gccagcagcc taagtttcgg cactgaagct    360

ttctttggac aaggcaccag actcacagtt gtagaggacc tgaacaaggt gttcccaccc    420

gaggtcgctg tgtttgagcc atcagaagca gagatctccc acacccaaaa ggccacactg    480

gtgtgcctgg ccacaggctt cttccccgac cacgtggagc tgagctggtg ggtgaatggg    540
```

```
aaggaggtgc acagtggggt cagcacggac ccgcagcccc tcaaggagca gcccgccctc    600

aatgactcca gatactgcct gagcagccgc ctgagggtct cggccacctt ctggcagaac    660

ccccgcaacc acttccgctg tcaagtccag ttctacgggc tctcggagaa tgacgagtgg    720

acccaggata gggccaaacc cgtcacccag atcgtcagcg ccgaggcctg ggtagagca     780

tgtggcttta cctcgtccta ccagcaaggg gtcctgtctg ccaccatcct ctatgagatc    840

ctgctaggga aggccaccct gtatgctgtg ctggtcagcg cccttgtgtt gatggccatg    900

gtcaagagaa aggatttc                                                  918
```

<210> SEQ ID NO 35
<211> LENGTH: 918
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: NT of beta chain of F5mut 3

<400> SEQUENCE: 35

```
atgagaatca ggctcctgtg ctgtgtggcc ttttctctcc tgtgggcagg tccagtgatt     60

gctgggatca cccaggcacc aacatctcag atcctggcag caggacggcg catgacactg    120

agatgtaccc aggatatgag acataatgcc atgtactggt atagacaaga tctaggactg    180

gggctaaggc tcatccatta ttcaaatgtg atgggtacca ctggcaaagg agaagtccct    240

gatggttata gtgtctccag agcaaacaca gatgatttcc ccctcacgtt ggcgtctgct    300

gtaccctctc agacatctgt gtacttctgt gccagcagcc taagtttcgg cactgaagct    360

ttctttggac aaggcaccag actcacagtt gtagaggacc tgaacaaggt gttcccaccc    420

gaggtcgctg tgtttgagcc atcagaagca gagatctccc acacccaaaa ggccacactg    480

gtgtgcctgg ccacaggctt cttccccgac cacgtggagc tgagctggtg ggtgaatggg    540

aaggaggtgc acagtggggt cagcacggac ccgcagcccc tcaaggagca gcccgccctc    600

aatgactcca gatactgcct gagcagccgc ctgagggtct cggccacctt ctggcagaac    660

ccccgcaacc acttccgctg tcaagtccag ttctacgggc tctcggagaa tgacgagtgg    720

acccaggata gggccaaacc cgtcacccag atcgtcagcg ccgaggcctg ggtagagca     780

tgtggcttta cctcgtccta ccagcaaggg gtcctgtctg ccaccatcct ctatgagatc    840

ctgctaggga aggccaccct gtatgctgtg ctggtcagcg cccttgtgtt gatggccatg    900

gtcaagagaa aggatttc                                                  918
```

<210> SEQ ID NO 36
<211> LENGTH: 918
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: NT of beta chain of F5mut2

<400> SEQUENCE: 36

```
atgagaatca ggctcctgtg ctgtgtggcc ttttctctcc tgtgggcagg tccagtgatt     60

gctgggatca cccaggcacc aacatctcag atcctggcag caggacggcg catgacactg    120

agatgtaccc aggatatgag acataatgcc atgtactggt atagacaaga tctaggactg    180
```

-continued

```
gggctaaggc tcatccatta ttcaaatgtg gcaggtgcca ctggcaaagg agaagtccct    240

gatggttata gtgtctccag agcaaacaca gatgatttcc ccctcacgtt ggcgtctgct    300

gtaccctctc agacatctgt gtacttctgt gccagcagcc taagtttcgg cactgaagct    360

ttctttggac aaggcaccag actcacagtt gtagaggacc tgaacaaggt gttcccaccc    420

gaggtcgctg tgtttgagcc atcagaagca gagatctccc acacccaaaa ggccacactg    480

gtgtgcctgg ccacaggctt cttccccgac cacgtggagc tgagctggtg ggtgaatggg    540

aaggaggtgc acagtggggt cagcacggac ccgcagcccc tcaaggagca gcccgccctc    600

aatgactcca gatactgcct gagcagccgc ctgagggtct cggccacctt ctggcagaac    660

ccccgcaacc acttccgctg tcaagtccag ttctacgggc tctcggagaa tgacgagtgg    720

acccaggata gggccaaacc cgtcacccag atcgtcagcg ccgaggcctg ggtagagca     780

tgtggcttta cctcgtccta ccagcaaggg gtcctgtctg ccaccatcct ctatgagatc    840

ctgctaggga aggccaccct gtatgctgtg ctggtcagcg cccttgtgtt gatggccatg    900

gtcaagagaa aggatttc                                                  918
```

<210> SEQ ID NO 37
<211> LENGTH: 287
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: AA of full length beta chain of F5mut2

<400> SEQUENCE: 37

```
Ile Ala Gly Ile Thr Gln Ala Pro Thr Ser Gln Ile Leu Ala Ala Gly
1               5                   10                  15

Arg Arg Met Thr Leu Arg Cys Thr Gln Asp Met Arg His Asn Ala Met
            20                  25                  30

Tyr Trp Tyr Arg Gln Asp Leu Gly Leu Gly Leu Arg Leu Ile His Tyr
        35                  40                  45

Ser Asn Val Ala Gly Ala Thr Gly Lys Gly Glu Val Pro Asp Gly Tyr
    50                  55                  60

Ser Val Ser Arg Ala Asn Thr Asp Asp Phe Pro Leu Thr Leu Ala Ser
65                  70                  75                  80

Ala Val Pro Ser Gln Thr Ser Val Tyr Phe Cys Ala Ser Ser Leu Ser
                85                  90                  95

Phe Gly Thr Glu Ala Phe Phe Gly Gln Gly Thr Arg Leu Thr Val Val
            100                 105                 110

Glu Asp Leu Asn Lys Val Phe Pro Pro Glu Val Ala Val Phe Glu Pro
        115                 120                 125

Ser Glu Ala Glu Ile Ser His Thr Gln Lys Ala Thr Leu Val Cys Leu
    130                 135                 140

Ala Thr Gly Phe Phe Pro Asp His Val Glu Leu Ser Trp Trp Val Asn
145                 150                 155                 160

Gly Lys Glu Val His Ser Gly Val Ser Thr Asp Pro Gln Pro Leu Lys
                165                 170                 175

Glu Gln Pro Ala Leu Asn Asp Ser Arg Tyr Cys Leu Ser Ser Arg Leu
            180                 185                 190

Arg Val Ser Ala Thr Phe Trp Gln Asn Pro Arg Asn His Phe Arg Cys
        195                 200                 205

Gln Val Gln Phe Tyr Gly Leu Ser Glu Asn Asp Glu Trp Thr Gln Asp
```

```
    210                 215                 220

Arg Ala Lys Pro Val Thr Gln Ile Val Ser Ala Glu Ala Trp Gly Arg
225                 230                 235                 240

Ala Cys Gly Phe Thr Ser Ser Tyr Gln Gln Gly Val Leu Ser Ala Thr
                245                 250                 255

Ile Leu Tyr Glu Ile Leu Leu Gly Lys Ala Thr Leu Tyr Ala Val Leu
            260                 265                 270

Val Ser Ala Leu Val Leu Met Ala Met Val Lys Arg Lys Asp Phe
        275                 280                 285


<210> SEQ ID NO 38
<211> LENGTH: 287
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: AA of full length beta chain of F5mut3

<400> SEQUENCE: 38

Ile Ala Gly Ile Thr Gln Ala Pro Thr Ser Gln Ile Leu Ala Ala Gly
1               5                   10                  15

Arg Arg Met Thr Leu Arg Cys Thr Gln Asp Met Arg His Asn Ala Met
            20                  25                  30

Tyr Trp Tyr Arg Gln Asp Leu Gly Leu Gly Leu Arg Leu Ile His Tyr
        35                  40                  45

Ser Asn Val Met Gly Thr Thr Gly Lys Gly Glu Val Pro Asp Gly Tyr
    50                  55                  60

Ser Val Ser Arg Ala Asn Thr Asp Asp Phe Pro Leu Thr Leu Ala Ser
65                  70                  75                  80

Ala Val Pro Ser Gln Thr Ser Val Tyr Phe Cys Ala Ser Ser Leu Ser
                85                  90                  95

Phe Gly Thr Glu Ala Phe Phe Gly Gln Gly Thr Arg Leu Thr Val Val
            100                 105                 110

Glu Asp Leu Asn Lys Val Phe Pro Pro Glu Val Ala Val Phe Glu Pro
        115                 120                 125

Ser Glu Ala Glu Ile Ser His Thr Gln Lys Ala Thr Leu Val Cys Leu
    130                 135                 140

Ala Thr Gly Phe Phe Pro Asp His Val Glu Leu Ser Trp Trp Val Asn
145                 150                 155                 160

Gly Lys Glu Val His Ser Gly Val Ser Thr Asp Pro Gln Pro Leu Lys
                165                 170                 175

Glu Gln Pro Ala Leu Asn Asp Ser Arg Tyr Cys Leu Ser Ser Arg Leu
            180                 185                 190

Arg Val Ser Ala Thr Phe Trp Gln Asn Pro Arg Asn His Phe Arg Cys
        195                 200                 205

Gln Val Gln Phe Tyr Gly Leu Ser Glu Asn Asp Glu Trp Thr Gln Asp
    210                 215                 220

Arg Ala Lys Pro Val Thr Gln Ile Val Ser Ala Glu Ala Trp Gly Arg
225                 230                 235                 240

Ala Cys Gly Phe Thr Ser Ser Tyr Gln Gln Gly Val Leu Ser Ala Thr
                245                 250                 255

Ile Leu Tyr Glu Ile Leu Leu Gly Lys Ala Thr Leu Tyr Ala Val Leu
            260                 265                 270

Val Ser Ala Leu Val Leu Met Ala Met Val Lys Arg Lys Asp Phe
```

275 280 285

<210> SEQ ID NO 39
<211> LENGTH: 287
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: AA of full length beta chain of F5mut4

<400> SEQUENCE: 39

```
Ile Ala Gly Ile Thr Gln Ala Pro Thr Ser Gln Ile Leu Ala Ala Gly
1               5                   10                  15

Arg Arg Met Thr Leu Arg Cys Thr Gln Asp Met Arg His Asn Ala Met
            20                  25                  30

Tyr Trp Tyr Arg Gln Asp Leu Gly Leu Gly Leu Arg Leu Ile His Tyr
        35                  40                  45

Ser Asn Thr Met Gly Ala Thr Gly Lys Gly Glu Val Pro Asp Gly Tyr
    50                  55                  60

Ser Val Ser Arg Ala Asn Thr Asp Asp Phe Pro Leu Thr Leu Ala Ser
65                  70                  75                  80

Ala Val Pro Ser Gln Thr Ser Val Tyr Phe Cys Ala Ser Ser Leu Ser
                85                  90                  95

Phe Gly Thr Glu Ala Phe Phe Gly Gln Gly Thr Arg Leu Thr Val Val
            100                 105                 110

Glu Asp Leu Asn Lys Val Phe Pro Pro Glu Val Ala Val Phe Glu Pro
        115                 120                 125

Ser Glu Ala Glu Ile Ser His Thr Gln Lys Ala Thr Leu Val Cys Leu
    130                 135                 140

Ala Thr Gly Phe Phe Pro Asp His Val Glu Leu Ser Trp Trp Val Asn
145                 150                 155                 160

Gly Lys Glu Val His Ser Gly Val Ser Thr Asp Pro Gln Pro Leu Lys
                165                 170                 175

Glu Gln Pro Ala Leu Asn Asp Ser Arg Tyr Cys Leu Ser Ser Arg Leu
            180                 185                 190

Arg Val Ser Ala Thr Phe Trp Gln Asn Pro Arg Asn His Phe Arg Cys
        195                 200                 205

Gln Val Gln Phe Tyr Gly Leu Ser Glu Asn Asp Glu Trp Thr Gln Asp
    210                 215                 220

Arg Ala Lys Pro Val Thr Gln Ile Val Ser Ala Glu Ala Trp Gly Arg
225                 230                 235                 240

Ala Cys Gly Phe Thr Ser Ser Tyr Gln Gln Gly Val Leu Ser Ala Thr
                245                 250                 255

Ile Leu Tyr Glu Ile Leu Leu Gly Lys Ala Thr Leu Tyr Ala Val Leu
            260                 265                 270

Val Ser Ala Leu Val Leu Met Ala Met Val Lys Arg Lys Asp Phe
        275                 280                 285
```

<210> SEQ ID NO 40
<211> LENGTH: 49
<212> TYPE: DNA
<213> ORGANISM: Artificial Sequence
<220> FEATURE:
<223> OTHER INFORMATION: Synthetic

<400> SEQUENCE: 40
gactaattaa ccctcactaa agggacacca tgagcatcgg cctcctgtg 49

<210> SEQ ID NO 41
<211> LENGTH: 40
<212> TYPE: DNA
<213> ORGANISM: Artificial Sequence
<220> FEATURE:
<223> OTHER INFORMATION: Synthetic

<400> SEQUENCE: 41
ctccccggtg ttcccgacgt aactgctggc acagaagtac 40

<210> SEQ ID NO 42
<211> LENGTH: 44
<212> TYPE: DNA
<213> ORGANISM: Artificial Sequence
<220> FEATURE:
<223> OTHER INFORMATION: Synthetic

<400> SEQUENCE: 42
cagcagttac gtcgggaaca ccggggagct gttttttgga gaag 44

<210> SEQ ID NO 43
<211> LENGTH: 90
<212> TYPE: DNA
<213> ORGANISM: Artificial Sequence
<220> FEATURE:
<223> OTHER INFORMATION: Synthetic

<400> SEQUENCE: 43
tttttttttt tttttttttt tttttttttt tttttttttt tttttttttt tttttttttt 60
tttttcagcc tctggaatcc tttctcttga 90

<210> SEQ ID NO 44
<211> LENGTH: 49
<212> TYPE: DNA
<213> ORGANISM: Artificial Sequence
<220> FEATURE:
<223> OTHER INFORMATION: Synthetic

<400> SEQUENCE: 44
gactaattaa ccctcactaa agggacacca tgagcatcgg cctcctgtg 49

<210> SEQ ID NO 45
<211> LENGTH: 87
<212> TYPE: DNA
<213> ORGANISM: Artificial Sequence
<220> FEATURE:
<223> OTHER INFORMATION: Synthetic

<400> SEQUENCE: 45
tttttttttt tttttttttt tttttttttt tttttttttt tttttttttt tttttttttt 60
tttttcagcc tctggaatcc tttctct 87

<210> SEQ ID NO 46
<211> LENGTH: 67
<212> TYPE: DNA
<213> ORGANISM: Artificial Sequence
<220> FEATURE:
<223> OTHER INFORMATION: Synthetic

<400> SEQUENCE: 46
ctggttcctc ttccaaatgt aggtatgtag cttcctcctg atgtgggcct cacagcacag 60
aggtagg 67

<210> SEQ ID NO 47
<211> LENGTH: 47
<212> TYPE: DNA
<213> ORGANISM: Artificial Sequence
<220> FEATURE:
<223> OTHER INFORMATION: Synthetic

<400> SEQUENCE: 47
gactaattaa ccctcactaa agggacacca tggagaccct cttgggc 47

<210> SEQ ID NO 48
<211> LENGTH: 66
<212> TYPE: DNA
<213> ORGANISM: Artificial Sequence
<220> FEATURE:
<223> OTHER INFORMATION: Synthetic

<400> SEQUENCE: 48
ctacatacct acatttggaa gaggaaccag ccttattgtt catccgtata tccagaaccc 60
tgaccc 66

<210> SEQ ID NO 49
<211> LENGTH: 89
<212> TYPE: DNA
<213> ORGANISM: Artificial Sequence
<220> FEATURE:
<223> OTHER INFORMATION: Synthetic

<400> SEQUENCE: 49
tttttttttt tttttttttt tttttttttt tttttttttt tttttttttt tttttttttt 60
tttttcagct ggaccacagc cgcagcgtc 89

<210> SEQ ID NO 50
<211> LENGTH: 47
<212> TYPE: DNA
<213> ORGANISM: Artificial Sequence
<220> FEATURE:
<223> OTHER INFORMATION: Synthetic

<400> SEQUENCE: 50
gactaattaa ccctcactaa agggacacca tggagaccct cttgggc 47

<210> SEQ ID NO 51
<211> LENGTH: 87
<212> TYPE: DNA
<213> ORGANISM: Artificial Sequence
<220> FEATURE:
<223> OTHER INFORMATION: Synthetic

<400> SEQUENCE: 51
tttttttttt tttttttttt tttttttttt tttttttttt tttttttttt tttttttttt 60
tttttcagct ggaccacagc cgcagcg 87

<210> SEQ ID NO 52
<211> LENGTH: 49
<212> TYPE: DNA
<213> ORGANISM: Artificial Sequence
<220> FEATURE:
<223> OTHER INFORMATION: Synthetic

<400> SEQUENCE: 52
gactaattaa ccctcactaa agggacacca tgagcatcgg cctcctgtg 49

<210> SEQ ID NO 53
<211> LENGTH: 22
<212> TYPE: DNA
<213> ORGANISM: Artificial Sequence
<220> FEATURE:
<223> OTHER INFORMATION: Synthetic

<400> SEQUENCE: 53
tgagtaatga atcagcctca gc 22

<210> SEQ ID NO 54
<211> LENGTH: 55
<212> TYPE: DNA
<213> ORGANISM: Artificial Sequence
<220> FEATURE:
<223> OTHER INFORMATION: Synthetic

<400> SEQUENCE: 54
gctgaggctg attcattact cagttgccgc tggtatcact gaccaaggag aagtc 55

<210> SEQ ID NO 55
<211> LENGTH: 87
<212> TYPE: DNA
<213> ORGANISM: Artificial Sequence
<220> FEATURE:
<223> OTHER INFORMATION: Synthetic

<400> SEQUENCE: 55
tttttttttt tttttttttt tttttttttt tttttttttt tttttttttt tttttttttt 60
tttttcagcc tctggaatcc tttctct 87

<210> SEQ ID NO 56
<211> LENGTH: 55
<212> TYPE: DNA
<213> ORGANISM: Artificial Sequence
<220> FEATURE:
<223> OTHER INFORMATION: Synthetic

<400> SEQUENCE: 56
gctgaggctg attcattact cagttggtat cggtatcact gaccaaggag aagtc 55

<210> SEQ ID NO 57
<211> LENGTH: 87
<212> TYPE: DNA
<213> ORGANISM: Artificial Sequence
<220> FEATURE:
<223> OTHER INFORMATION: Synthetic

<400> SEQUENCE: 57
tttttttttt tttttttttt tttttttttt tttttttttt tttttttttt tttttttttt 60
tttttcagcc tctggaatcc tttctct 87

<210> SEQ ID NO 58
<211> LENGTH: 55
<212> TYPE: DNA
<213> ORGANISM: Artificial Sequence
<220> FEATURE:
<223> OTHER INFORMATION: Synthetic

<400> SEQUENCE: 58
gctgaggctg attcattact cagttgccat cggtatcact gaccaaggag aagtc 55

<210> SEQ ID NO 59
<211> LENGTH: 87

<212> TYPE: DNA
<213> ORGANISM: Artificial Sequence
<220> FEATURE:
<223> OTHER INFORMATION: Synthetic

<400> SEQUENCE: 59
tttttttttt tttttttttt tttttttttt tttttttttt tttttttttt tttttttttt 60
tttttcagcc tctggaatcc tttctct 87

<210> SEQ ID NO 60
<211> LENGTH: 49
<212> TYPE: DNA
<213> ORGANISM: Artificial Sequence
<220> FEATURE:
<223> OTHER INFORMATION: Synthetic

<400> SEQUENCE: 60
gactaattaa ccctcactaa agggacacca tgagcatcgg cctcctgtg 49

<210> SEQ ID NO 61
<211> LENGTH: 86
<212> TYPE: DNA
<213> ORGANISM: Artificial Sequence
<220> FEATURE:
<223> OTHER INFORMATION: Synthetic

<400> SEQUENCE: 61
tttttttttt tttttttttt tttttttttt tttttttttt tttttttttt tttttttttt 60
ttttcagcct ctggaatcct ttctct 86

<210> SEQ ID NO 62
<211> LENGTH: 57
<212> TYPE: DNA
<213> ORGANISM: Artificial Sequence
<220> FEATURE:
<223> OTHER INFORMATION: Synthetic

<400> SEQUENCE: 62
gactaattaa ccctcactaa agggacacca tgatgaaatc cttgagagtt ttactag 57

<210> SEQ ID NO 63
<211> LENGTH: 89
<212> TYPE: DNA
<213> ORGANISM: Artificial Sequence
<220> FEATURE:
<223> OTHER INFORMATION: Synthetic

<400> SEQUENCE: 63
tttttttttt tttttttttt tttttttttt tttttttttt tttttttttt tttttttttt 60
tttttcagct ggaccacagc cgcagcgtc 89

<210> SEQ ID NO 64
<211> LENGTH: 83
<212> TYPE: DNA
<213> ORGANISM: Artificial Sequence
<220> FEATURE:
<223> OTHER INFORMATION: Synthetic

<400> SEQUENCE: 64
tcagaattaa ccctcactaa agggactagt cctgcaggtt taaacgaatt cgcccttcac 60
catgagaatc aggctcctgt gct 83

<210> SEQ ID NO 65

<211> LENGTH: 89
<212> TYPE: DNA
<213> ORGANISM: Artificial Sequence
<220> FEATURE:
<223> OTHER INFORMATION: Synthetic

<400> SEQUENCE: 65
tttttttttt tttttttttt tttttttttt tttttttttt tttttttttt tttttttttt 60
ttttttcaga aatcctttct cttgaccat 89

<210> SEQ ID NO 66
<211> LENGTH: 83
<212> TYPE: DNA
<213> ORGANISM: Artificial Sequence
<220> FEATURE:
<223> OTHER INFORMATION: Synthetic

<400> SEQUENCE: 66
tcagaattaa ccctcactaa agggactagt cctgcaggtt taaacgaatt cgcccttcac 60
catgagaatc aggctcctgt gct 83

<210> SEQ ID NO 67
<211> LENGTH: 22
<212> TYPE: DNA
<213> ORGANISM: Artificial Sequence
<220> FEATURE:
<223> OTHER INFORMATION: Synthetic

<400> SEQUENCE: 67
tgaataatgg atgagcctta gc 22

<210> SEQ ID NO 68
<211> LENGTH: 56
<212> TYPE: DNA
<213> ORGANISM: Artificial Sequence
<220> FEATURE:
<223> OTHER INFORMATION: Synthetic

<400> SEQUENCE: 68
gctaaggctc atccattatt caaatactgc aggtgccact ggcaaaggag aagtcc 56

<210> SEQ ID NO 69
<211> LENGTH: 89
<212> TYPE: DNA
<213> ORGANISM: Artificial Sequence
<220> FEATURE:
<223> OTHER INFORMATION: Synthetic

<400> SEQUENCE: 69
tttttttttt tttttttttt tttttttttt tttttttttt tttttttttt tttttttttt 60
ttttttcaga aatcctttct cttgaccat 89

<210> SEQ ID NO 70
<211> LENGTH: 56
<212> TYPE: DNA
<213> ORGANISM: Artificial Sequence
<220> FEATURE:
<223> OTHER INFORMATION: Synthetic

<400> SEQUENCE: 70
gctaaggctc atccattatt caaatgtggc aggtgccact ggcaaaggag aagtcc 56

<210> SEQ ID NO 71
<211> LENGTH: 89

<212> TYPE: DNA
<213> ORGANISM: Artificial Sequence
<220> FEATURE:
<223> OTHER INFORMATION: Synthetic

<400> SEQUENCE: 71
tttttttttt tttttttttt tttttttttt tttttttttt tttttttttt tttttttttt 60
ttttttcaga aatcctttct cttgaccat 89

<210> SEQ ID NO 72
<211> LENGTH: 56
<212> TYPE: DNA
<213> ORGANISM: Artificial Sequence
<220> FEATURE:
<223> OTHER INFORMATION: Synthetic

<400> SEQUENCE: 72
gctaaggctc atccattatt caaatgtgat gggtaccact ggcaaaggag aagtcc 56

<210> SEQ ID NO 73
<211> LENGTH: 89
<212> TYPE: DNA
<213> ORGANISM: Artificial Sequence
<220> FEATURE:
<223> OTHER INFORMATION: Synthetic

<400> SEQUENCE: 73
tttttttttt tttttttttt tttttttttt tttttttttt tttttttttt tttttttttt 60
ttttttcaga aatcctttct cttgaccat 89

<210> SEQ ID NO 74
<211> LENGTH: 56
<212> TYPE: DNA
<213> ORGANISM: Artificial Sequence
<220> FEATURE:
<223> OTHER INFORMATION: Synthetic

<400> SEQUENCE: 74
gctaaggctc atccattatt caaatactat gggtgccact ggcaaaggag aagtcc 56

<210> SEQ ID NO 75
<211> LENGTH: 89
<212> TYPE: DNA
<213> ORGANISM: Artificial Sequence
<220> FEATURE:
<223> OTHER INFORMATION: Synthetic

<400> SEQUENCE: 75
tttttttttt tttttttttt tttttttttt tttttttttt tttttttttt tttttttttt 60
ttttttcaga aatcctttct cttgaccat 89

<210> SEQ ID NO 76
<211> LENGTH: 56
<212> TYPE: DNA
<213> ORGANISM: Artificial Sequence
<220> FEATURE:
<223> OTHER INFORMATION: Synthetic

<400> SEQUENCE: 76
gctaaggctc atccattatt caaatgtgat gggtgccact ggcaaaggag aagtcc 56

<210> SEQ ID NO 77
<211> LENGTH: 89
<212> TYPE: DNA

<213> ORGANISM: Artificial Sequence
<220> FEATURE:
<223> OTHER INFORMATION: Synthetic

<400> SEQUENCE: 77
tttttttttt tttttttttt tttttttttt tttttttttt tttttttttt tttttttttt 60
ttttttcaga aatcctttct cttgaccat 89

<210> SEQ ID NO 78
<211> LENGTH: 50
<212> TYPE: DNA
<213> ORGANISM: Artificial Sequence
<220> FEATURE:
<223> OTHER INFORMATION: Synthetic

<400> SEQUENCE: 78
gactaattaa ccctcactaa agggacacca tgggcacaag gttgttcttc 50

<210> SEQ ID NO 79
<211> LENGTH: 89
<212> TYPE: DNA
<213> ORGANISM: Artificial Sequence
<220> FEATURE:
<223> OTHER INFORMATION: Synthetic

<400> SEQUENCE: 79
tttttttttt tttttttttt tttttttttt tttttttttt tttttttttt tttttttttt 60
ttttttcaga aatcctttct cttgaccat 89

<210> SEQ ID NO 80
<211> LENGTH: 50
<212> TYPE: DNA
<213> ORGANISM: Artificial Sequence
<220> FEATURE:
<223> OTHER INFORMATION: Synthetic

<400> SEQUENCE: 80
gactaattaa ccctcactaa agggacacca tgggcacaag gttgttcttc 50

<210> SEQ ID NO 81
<211> LENGTH: 89
<212> TYPE: DNA
<213> ORGANISM: Artificial Sequence
<220> FEATURE:
<223> OTHER INFORMATION: Synthetic

<400> SEQUENCE: 81
tttttttttt tttttttttt tttttttttt tttttttttt tttttttttt tttttttttt 60
ttttttcaga aatcctttct cttgaccat 89

<210> SEQ ID NO 82
<211> LENGTH: 50
<212> TYPE: DNA
<213> ORGANISM: Artificial Sequence
<220> FEATURE:
<223> OTHER INFORMATION: Synthetic

<400> SEQUENCE: 82
gactaattaa ccctcactaa agggacacca tgggcacaag gttgttcttc 50

<210> SEQ ID NO 83
<211> LENGTH: 20
<212> TYPE: DNA
<213> ORGANISM: Artificial Sequence
<220> FEATURE:
<223> OTHER INFORMATION: Synthetic

<400> SEQUENCE: 83
gtaatggatc agcctcagcc 20

<210> SEQ ID NO 84
<211> LENGTH: 55
<212> TYPE: DNA
<213> ORGANISM: Artificial Sequence
<220> FEATURE:
<223> OTHER INFORMATION: Synthetic

<400> SEQUENCE: 84
gctgaggctg atccattact catatgccgt taaagatact gacaaaggag aagtc 55

<210> SEQ ID NO 85
<211> LENGTH: 89
<212> TYPE: DNA
<213> ORGANISM: Artificial Sequence
<220> FEATURE:
<223> OTHER INFORMATION: Synthetic

<400> SEQUENCE: 85
tttttttttt tttttttttt tttttttttt tttttttttt tttttttttt tttttttttt 60
ttttttcaga aatcctttct cttgaccat 89

<210> SEQ ID NO 86
<211> LENGTH: 55
<212> TYPE: DNA
<213> ORGANISM: Artificial Sequence
<220> FEATURE:
<223> OTHER INFORMATION: Synthetic

<400> SEQUENCE: 86
gctgaggctg atccattact catatgccgc caaagatact gacaaaggag aagtc 55

<210> SEQ ID NO 87
<211> LENGTH: 89
<212> TYPE: DNA
<213> ORGANISM: Artificial Sequence
<220> FEATURE:
<223> OTHER INFORMATION: Synthetic

<400> SEQUENCE: 87
tttttttttt tttttttttt tttttttttt tttttttttt tttttttttt tttttttttt 60
ttttttcaga aatcctttct cttgaccat 89

<210> SEQ ID NO 88
<211> LENGTH: 50
<212> TYPE: DNA
<213> ORGANISM: Artificial Sequence
<220> FEATURE:
<223> OTHER INFORMATION: Synthetic

<400> SEQUENCE: 88
gactaattaa ccctcactaa agggacacca tgggcacaag gttgttcttc 50

<210> SEQ ID NO 89
<211> LENGTH: 89
<212> TYPE: DNA
<213> ORGANISM: Artificial Sequence
<220> FEATURE:
<223> OTHER INFORMATION: Synthetic

<400> SEQUENCE: 89
tttttttttt tttttttttt tttttttttt tttttttttt tttttttttt tttttttttt        60 tttttcaga aatcctttct cttgaccat        89

<210> SEQ ID NO 90
<211> LENGTH: 56
<212> TYPE: DNA
<213> ORGANISM: Artificial Sequence
<220> FEATURE:
<223> OTHER INFORMATION: Synthetic

<400> SEQUENCE: 90
gactaattaa ccctcactaa aggacacca tgctccttga acatttatta ataatc        56

<210> SEQ ID NO 91
<211> LENGTH: 88
<212> TYPE: DNA
<213> ORGANISM: Artificial Sequence
<220> FEATURE:
<223> OTHER INFORMATION: Synthetic

<400> SEQUENCE: 91
tttttttttt tttttttttt tttttttttt tttttttttt tttttttttt tttttttttt        60
tttttcagcg gaccacagcc gcagcgtc        88

<210> SEQ ID NO 92
<211> LENGTH: 9
<212> TYPE: PRT
<213> ORGANISM: Artificial Sequence
<220> FEATURE:
<223> OTHER INFORMATION: Synthetic

<400> SEQUENCE: 92

Ser Leu Leu Met Trp Ile Thr Gln Cys
1               5

<210> SEQ ID NO 93
<211> LENGTH: 9
<212> TYPE: PRT
<213> ORGANISM: Artificial Sequence
<220> FEATURE:
<223> OTHER INFORMATION: Synthetic

<400> SEQUENCE: 93

Lys Thr Trp Gly Gln Tyr Trp Gln Val
1               5

<210> SEQ ID NO 94
<211> LENGTH: 9
<212> TYPE: PRT
<213> ORGANISM: Artificial Sequence
<220> FEATURE:
<223> OTHER INFORMATION: Synthetic

<400> SEQUENCE: 94

Ala Ala Gly Ile Gly Ile Leu Thr Val
1               5

<210> SEQ ID NO 95
<211> LENGTH: 112
<212> TYPE: PRT
<213> ORGANISM: Artificial Sequence
<220> FEATURE:
<223> OTHER INFORMATION: Synthetic
<220> FEATURE:

<221> NAME/KEY: MISC_FEATURE
<223> OTHER INFORMATION: variable region of modified F5 TCR beta chain
      comprising AAGT (mature)

<400> SEQUENCE: 95

```
Ile Ala Gly Ile Thr Gln Ala Pro Thr Ser Gln Ile Leu Ala Ala Gly
1               5                   10                  15

Arg Arg Met Thr Leu Arg Cys Thr Gln Asp Met Arg His Asn Ala Met
            20                  25                  30

Tyr Trp Tyr Arg Gln Asp Leu Gly Leu Gly Leu Arg Leu Ile His Tyr
        35                  40                  45

Ser Asn Ala Ala Gly Thr Thr Gly Lys Gly Glu Val Pro Asp Gly Tyr
    50                  55                  60

Ser Val Ser Arg Ala Asn Thr Asp Asp Phe Pro Leu Thr Leu Ala Ser
65                  70                  75                  80

Ala Val Pro Ser Gln Thr Ser Val Tyr Phe Cys Ala Ser Ser Leu Ser
                85                  90                  95

Phe Gly Thr Glu Ala Phe Phe Gly Gln Gly Thr Arg Leu Thr Val Val
            100                 105                 110
```

<210> SEQ ID NO 96
<211> LENGTH: 112
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: variable region of modified F5 TCR beta chain
      comprising IAGT

<400> SEQUENCE: 96

```
Ile Ala Gly Ile Thr Gln Ala Pro Thr Ser Gln Ile Leu Ala Ala Gly
1               5                   10                  15

Arg Arg Met Thr Leu Arg Cys Thr Gln Asp Met Arg His Asn Ala Met
            20                  25                  30

Tyr Trp Tyr Arg Gln Asp Leu Gly Leu Gly Leu Arg Leu Ile His Tyr
        35                  40                  45

Ser Asn Ile Ala Gly Thr Thr Gly Lys Gly Glu Val Pro Asp Gly Tyr
    50                  55                  60

Ser Val Ser Arg Ala Asn Thr Asp Asp Phe Pro Leu Thr Leu Ala Ser
65                  70                  75                  80

Ala Val Pro Ser Gln Thr Ser Val Tyr Phe Cys Ala Ser Ser Leu Ser
                85                  90                  95

Phe Gly Thr Glu Ala Phe Phe Gly Gln Gly Thr Arg Leu Thr Val Val
            100                 105                 110
```

<210> SEQ ID NO 97
<211> LENGTH: 112
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: variable region of modified F5 TCR beta chain
      comprising TIGT

<400> SEQUENCE: 97

```
Ile Ala Gly Ile Thr Gln Ala Pro Thr Ser Gln Ile Leu Ala Ala Gly
1               5                   10                  15
```

```
Arg Arg Met Thr Leu Arg Cys Thr Gln Asp Met Arg His Asn Ala Met
            20                  25                  30

Tyr Trp Tyr Arg Gln Asp Leu Gly Leu Gly Leu Arg Leu Ile His Tyr
        35                  40                  45

Ser Asn Thr Ile Gly Thr Thr Gly Lys Gly Glu Val Pro Asp Gly Tyr
    50                  55                  60

Ser Val Ser Arg Ala Asn Thr Asp Asp Phe Pro Leu Thr Leu Ala Ser
65                  70                  75                  80

Ala Val Pro Ser Gln Thr Ser Val Tyr Phe Cys Ala Ser Ser Leu Ser
                85                  90                  95

Phe Gly Thr Glu Ala Phe Phe Gly Gln Gly Thr Arg Leu Thr Val Val
            100                 105                 110


<210> SEQ ID NO 98
<211> LENGTH: 112
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: variable region of modified F5 TCR beta chain
      comprising TVGT

<400> SEQUENCE: 98

Ile Ala Gly Ile Thr Gln Ala Pro Thr Ser Gln Ile Leu Ala Ala Gly
1               5                   10                  15

Arg Arg Met Thr Leu Arg Cys Thr Gln Asp Met Arg His Asn Ala Met
            20                  25                  30

Tyr Trp Tyr Arg Gln Asp Leu Gly Leu Gly Leu Arg Leu Ile His Tyr
        35                  40                  45

Ser Asn Thr Val Gly Thr Thr Gly Lys Gly Glu Val Pro Asp Gly Tyr
    50                  55                  60

Ser Val Ser Arg Ala Asn Thr Asp Asp Phe Pro Leu Thr Leu Ala Ser
65                  70                  75                  80

Ala Val Pro Ser Gln Thr Ser Val Tyr Phe Cys Ala Ser Ser Leu Ser
                85                  90                  95

Phe Gly Thr Glu Ala Phe Phe Gly Gln Gly Thr Arg Leu Thr Val Val
            100                 105                 110


<210> SEQ ID NO 99
<211> LENGTH: 112
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: variable region of modified F5 TCR beta chain
      comprising TAGG

<400> SEQUENCE: 99

Ile Ala Gly Ile Thr Gln Ala Pro Thr Ser Gln Ile Leu Ala Ala Gly
1               5                   10                  15

Arg Arg Met Thr Leu Arg Cys Thr Gln Asp Met Arg His Asn Ala Met
            20                  25                  30

Tyr Trp Tyr Arg Gln Asp Leu Gly Leu Gly Leu Arg Leu Ile His Tyr
        35                  40                  45

Ser Asn Thr Ala Gly Gly Thr Gly Lys Gly Glu Val Pro Asp Gly Tyr
    50                  55                  60
```

Ser Val Ser Arg Ala Asn Thr Asp Asp Phe Pro Leu Thr Leu Ala Ser
65 70 75 80

Ala Val Pro Ser Gln Thr Ser Val Tyr Phe Cys Ala Ser Ser Leu Ser
85 90 95

Phe Gly Thr Glu Ala Phe Phe Gly Gln Gly Thr Arg Leu Thr Val Val
100 105 110

<210> SEQ ID NO 100
<211> LENGTH: 112
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: variable region of modified F5 TCR beta chain comprising TAGS

<400> SEQUENCE: 100

Ile Ala Gly Ile Thr Gln Ala Pro Thr Ser Gln Ile Leu Ala Ala Gly
1 5 10 15

Arg Arg Met Thr Leu Arg Cys Thr Gln Asp Met Arg His Asn Ala Met
20 25 30

Tyr Trp Tyr Arg Gln Asp Leu Gly Leu Gly Leu Arg Leu Ile His Tyr
35 40 45

Ser Asn Thr Ala Gly Ser Thr Gly Lys Gly Glu Val Pro Asp Gly Tyr
50 55 60

Ser Val Ser Arg Ala Asn Thr Asp Asp Phe Pro Leu Thr Leu Ala Ser
65 70 75 80

Ala Val Pro Ser Gln Thr Ser Val Tyr Phe Cys Ala Ser Ser Leu Ser
85 90 95

Phe Gly Thr Glu Ala Phe Phe Gly Gln Gly Thr Arg Leu Thr Val Val
100 105 110

<210> SEQ ID NO 101
<211> LENGTH: 112
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: variable region of modified F5 TCR beta chain comprising VMGT

<400> SEQUENCE: 101

Ile Ala Gly Ile Thr Gln Ala Pro Thr Ser Gln Ile Leu Ala Ala Gly
1 5 10 15

Arg Arg Met Thr Leu Arg Cys Thr Gln Asp Met Arg His Asn Ala Met
20 25 30

Tyr Trp Tyr Arg Gln Asp Leu Gly Leu Gly Leu Arg Leu Ile His Tyr
35 40 45

Ser Asn Val Met Gly Thr Thr Gly Lys Gly Glu Val Pro Asp Gly Tyr
50 55 60

Ser Val Ser Arg Ala Asn Thr Asp Asp Phe Pro Leu Thr Leu Ala Ser
65 70 75 80

Ala Val Pro Ser Gln Thr Ser Val Tyr Phe Cys Ala Ser Ser Leu Ser
85 90 95

Phe Gly Thr Glu Ala Phe Phe Gly Gln Gly Thr Arg Leu Thr Val Val
100 105 110

<210> SEQ ID NO 102
<211> LENGTH: 112
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: variable region of modified F5 TCR beta chain
comprising VAGA

<400> SEQUENCE: 102

```
Ile Ala Gly Ile Thr Gln Ala Pro Thr Ser Gln Ile Leu Ala Ala Gly
1               5                   10                  15

Arg Arg Met Thr Leu Arg Cys Thr Gln Asp Met Arg His Asn Ala Met
            20                  25                  30

Tyr Trp Tyr Arg Gln Asp Leu Gly Leu Gly Leu Arg Leu Ile His Tyr
        35                  40                  45

Ser Asn Val Ala Gly Ala Thr Gly Lys Gly Glu Val Pro Asp Gly Tyr
    50                  55                  60

Ser Val Ser Arg Ala Asn Thr Asp Asp Phe Pro Leu Thr Leu Ala Ser
65                  70                  75                  80

Ala Val Pro Ser Gln Thr Ser Val Tyr Phe Cys Ala Ser Ser Leu Ser
                85                  90                  95

Phe Gly Thr Glu Ala Phe Phe Gly Gln Gly Thr Arg Leu Thr Val Val
            100                 105                 110
```

<210> SEQ ID NO 103
<211> LENGTH: 112
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: variable region of modified F5 TCR beta chain
comprising TMGA

<400> SEQUENCE: 103

```
Ile Ala Gly Ile Thr Gln Ala Pro Thr Ser Gln Ile Leu Ala Ala Gly
1               5                   10                  15

Arg Arg Met Thr Leu Arg Cys Thr Gln Asp Met Arg His Asn Ala Met
            20                  25                  30

Tyr Trp Tyr Arg Gln Asp Leu Gly Leu Gly Leu Arg Leu Ile His Tyr
        35                  40                  45

Ser Asn Thr Met Gly Ala Thr Gly Lys Gly Glu Val Pro Asp Gly Tyr
    50                  55                  60

Ser Val Ser Arg Ala Asn Thr Asp Asp Phe Pro Leu Thr Leu Ala Ser
65                  70                  75                  80

Ala Val Pro Ser Gln Thr Ser Val Tyr Phe Cys Ala Ser Ser Leu Ser
                85                  90                  95

Phe Gly Thr Glu Ala Phe Phe Gly Gln Gly Thr Arg Leu Thr Val Val
            100                 105                 110
```

<210> SEQ ID NO 104
<211> LENGTH: 287
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: full length modified F5 TCR beta chain
      comprising AAGT

<400> SEQUENCE: 104

Ile Ala Gly Ile Thr Gln Ala Pro Thr Ser Gln Ile Leu Ala Ala Gly
1               5                   10                  15

Arg Arg Met Thr Leu Arg Cys Thr Gln Asp Met Arg His Asn Ala Met
            20                  25                  30

Tyr Trp Tyr Arg Gln Asp Leu Gly Leu Gly Leu Arg Leu Ile His Tyr
        35                  40                  45

Ser Asn Ala Ala Gly Thr Thr Gly Lys Gly Glu Val Pro Asp Gly Tyr
    50                  55                  60

Ser Val Ser Arg Ala Asn Thr Asp Asp Phe Pro Leu Thr Leu Ala Ser
65                  70                  75                  80

Ala Val Pro Ser Gln Thr Ser Val Tyr Phe Cys Ala Ser Ser Leu Ser
                85                  90                  95

Phe Gly Thr Glu Ala Phe Phe Gly Gln Gly Thr Arg Leu Thr Val Val
            100                 105                 110

Glu Asp Leu Asn Lys Val Phe Pro Pro Glu Val Ala Val Phe Glu Pro
        115                 120                 125

Ser Glu Ala Glu Ile Ser His Thr Gln Lys Ala Thr Leu Val Cys Leu
    130                 135                 140

Ala Thr Gly Phe Phe Pro Asp His Val Glu Leu Ser Trp Trp Val Asn
145                 150                 155                 160

Gly Lys Glu Val His Ser Gly Val Ser Thr Asp Pro Gln Pro Leu Lys
                165                 170                 175

Glu Gln Pro Ala Leu Asn Asp Ser Arg Tyr Cys Leu Ser Ser Arg Leu
            180                 185                 190

Arg Val Ser Ala Thr Phe Trp Gln Asn Pro Arg Asn His Phe Arg Cys
        195                 200                 205

Gln Val Gln Phe Tyr Gly Leu Ser Glu Asn Asp Glu Trp Thr Gln Asp
    210                 215                 220

Arg Ala Lys Pro Val Thr Gln Ile Val Ser Ala Glu Ala Trp Gly Arg
225                 230                 235                 240

Ala Cys Gly Phe Thr Ser Ser Tyr Gln Gln Gly Val Leu Ser Ala Thr
                245                 250                 255

Ile Leu Tyr Glu Ile Leu Leu Gly Lys Ala Thr Leu Tyr Ala Val Leu
            260                 265                 270

Val Ser Ala Leu Val Leu Met Ala Met Val Lys Arg Lys Asp Phe
        275                 280                 285

<210> SEQ ID NO 105
<211> LENGTH: 287
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: full length modified F5 TCR beta chain
      comprising IAGT

<400> SEQUENCE: 105

Ile Ala Gly Ile Thr Gln Ala Pro Thr Ser Gln Ile Leu Ala Ala Gly
1               5                   10                  15

Arg Arg Met Thr Leu Arg Cys Thr Gln Asp Met Arg His Asn Ala Met
            20                  25                  30

-continued

```
Tyr Trp Tyr Arg Gln Asp Leu Gly Leu Gly Leu Arg Leu Ile His Tyr
        35                  40                  45

Ser Asn Ile Ala Gly Thr Thr Gly Lys Gly Glu Val Pro Asp Gly Tyr
    50                  55                  60

Ser Val Ser Arg Ala Asn Thr Asp Asp Phe Pro Leu Thr Leu Ala Ser
65                  70                  75                  80

Ala Val Pro Ser Gln Thr Ser Val Tyr Phe Cys Ala Ser Ser Leu Ser
                85                  90                  95

Phe Gly Thr Glu Ala Phe Phe Gly Gln Gly Thr Arg Leu Thr Val Val
            100                 105                 110

Glu Asp Leu Asn Lys Val Phe Pro Pro Glu Val Ala Val Phe Glu Pro
        115                 120                 125

Ser Glu Ala Glu Ile Ser His Thr Gln Lys Ala Thr Leu Val Cys Leu
    130                 135                 140

Ala Thr Gly Phe Phe Pro Asp His Val Glu Leu Ser Trp Trp Val Asn
145                 150                 155                 160

Gly Lys Glu Val His Ser Gly Val Ser Thr Asp Pro Gln Pro Leu Lys
                165                 170                 175

Glu Gln Pro Ala Leu Asn Asp Ser Arg Tyr Cys Leu Ser Ser Arg Leu
            180                 185                 190

Arg Val Ser Ala Thr Phe Trp Gln Asn Pro Arg Asn His Phe Arg Cys
        195                 200                 205

Gln Val Gln Phe Tyr Gly Leu Ser Glu Asn Asp Glu Trp Thr Gln Asp
    210                 215                 220

Arg Ala Lys Pro Val Thr Gln Ile Val Ser Ala Glu Ala Trp Gly Arg
225                 230                 235                 240

Ala Cys Gly Phe Thr Ser Ser Tyr Gln Gln Gly Val Leu Ser Ala Thr
                245                 250                 255

Ile Leu Tyr Glu Ile Leu Leu Gly Lys Ala Thr Leu Tyr Ala Val Leu
            260                 265                 270

Val Ser Ala Leu Val Leu Met Ala Met Val Lys Arg Lys Asp Phe
        275                 280                 285


<210> SEQ ID NO 106
<211> LENGTH: 287
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: full length modified F5 TCR beta chain
      comprising TIGT

<400> SEQUENCE: 106

Ile Ala Gly Ile Thr Gln Ala Pro Thr Ser Gln Ile Leu Ala Ala Gly
1               5                   10                  15

Arg Arg Met Thr Leu Arg Cys Thr Gln Asp Met Arg His Asn Ala Met
            20                  25                  30

Tyr Trp Tyr Arg Gln Asp Leu Gly Leu Gly Leu Arg Leu Ile His Tyr
        35                  40                  45

Ser Asn Thr Ile Gly Thr Thr Gly Lys Gly Glu Val Pro Asp Gly Tyr
    50                  55                  60

Ser Val Ser Arg Ala Asn Thr Asp Asp Phe Pro Leu Thr Leu Ala Ser
65                  70                  75                  80

Ala Val Pro Ser Gln Thr Ser Val Tyr Phe Cys Ala Ser Ser Leu Ser
                85                  90                  95
```

```
Phe Gly Thr Glu Ala Phe Phe Gly Gln Gly Thr Arg Leu Thr Val Val
            100                 105                 110

Glu Asp Leu Asn Lys Val Phe Pro Pro Glu Val Ala Val Phe Glu Pro
        115                 120                 125

Ser Glu Ala Glu Ile Ser His Thr Gln Lys Ala Thr Leu Val Cys Leu
    130                 135                 140

Ala Thr Gly Phe Phe Pro Asp His Val Glu Leu Ser Trp Trp Val Asn
145                 150                 155                 160

Gly Lys Glu Val His Ser Gly Val Ser Thr Asp Pro Gln Pro Leu Lys
                165                 170                 175

Glu Gln Pro Ala Leu Asn Asp Ser Arg Tyr Cys Leu Ser Ser Arg Leu
            180                 185                 190

Arg Val Ser Ala Thr Phe Trp Gln Asn Pro Arg Asn His Phe Arg Cys
        195                 200                 205

Gln Val Gln Phe Tyr Gly Leu Ser Glu Asn Asp Glu Trp Thr Gln Asp
    210                 215                 220

Arg Ala Lys Pro Val Thr Gln Ile Val Ser Ala Glu Ala Trp Gly Arg
225                 230                 235                 240

Ala Cys Gly Phe Thr Ser Ser Tyr Gln Gln Gly Val Leu Ser Ala Thr
                245                 250                 255

Ile Leu Tyr Glu Ile Leu Leu Gly Lys Ala Thr Leu Tyr Ala Val Leu
            260                 265                 270

Val Ser Ala Leu Val Leu Met Ala Met Val Lys Arg Lys Asp Phe
        275                 280                 285
```

<210> SEQ ID NO 107
<211> LENGTH: 287
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: full length modified F5 TCR beta chain comprising TVGT

<400> SEQUENCE: 107

```
Ile Ala Gly Ile Thr Gln Ala Pro Thr Ser Gln Ile Leu Ala Ala Gly
1               5                   10                  15

Arg Arg Met Thr Leu Arg Cys Thr Gln Asp Met Arg His Asn Ala Met
            20                  25                  30

Tyr Trp Tyr Arg Gln Asp Leu Gly Leu Gly Leu Arg Leu Ile His Tyr
        35                  40                  45

Ser Asn Thr Val Gly Thr Thr Gly Lys Gly Glu Val Pro Asp Gly Tyr
    50                  55                  60

Ser Val Ser Arg Ala Asn Thr Asp Asp Phe Pro Leu Thr Leu Ala Ser
65                  70                  75                  80

Ala Val Pro Ser Gln Thr Ser Val Tyr Phe Cys Ala Ser Ser Leu Ser
                85                  90                  95

Phe Gly Thr Glu Ala Phe Phe Gly Gln Gly Thr Arg Leu Thr Val Val
            100                 105                 110

Glu Asp Leu Asn Lys Val Phe Pro Pro Glu Val Ala Val Phe Glu Pro
        115                 120                 125

Ser Glu Ala Glu Ile Ser His Thr Gln Lys Ala Thr Leu Val Cys Leu
    130                 135                 140

Ala Thr Gly Phe Phe Pro Asp His Val Glu Leu Ser Trp Trp Val Asn
```

145 150 155 160

Gly Lys Glu Val His Ser Gly Val Ser Thr Asp Pro Gln Pro Leu Lys
165 170 175

Glu Gln Pro Ala Leu Asn Asp Ser Arg Tyr Cys Leu Ser Ser Arg Leu
180 185 190

Arg Val Ser Ala Thr Phe Trp Gln Asn Pro Arg Asn His Phe Arg Cys
195 200 205

Gln Val Gln Phe Tyr Gly Leu Ser Glu Asn Asp Glu Trp Thr Gln Asp
210 215 220

Arg Ala Lys Pro Val Thr Gln Ile Val Ser Ala Glu Ala Trp Gly Arg
225 230 235 240

Ala Cys Gly Phe Thr Ser Ser Tyr Gln Gln Gly Val Leu Ser Ala Thr
245 250 255

Ile Leu Tyr Glu Ile Leu Leu Gly Lys Ala Thr Leu Tyr Ala Val Leu
260 265 270

Val Ser Ala Leu Val Leu Met Ala Met Val Lys Arg Lys Asp Phe
275 280 285

<210> SEQ ID NO 108
<211> LENGTH: 287
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: full length modified F5 TCR beta chain comprising TAGG

<400> SEQUENCE: 108

Ile Ala Gly Ile Thr Gln Ala Pro Thr Ser Gln Ile Leu Ala Ala Gly
1 5 10 15

Arg Arg Met Thr Leu Arg Cys Thr Gln Asp Met Arg His Asn Ala Met
20 25 30

Tyr Trp Tyr Arg Gln Asp Leu Gly Leu Gly Leu Arg Leu Ile His Tyr
35 40 45

Ser Asn Thr Ala Gly Gly Thr Gly Lys Gly Glu Val Pro Asp Gly Tyr
50 55 60

Ser Val Ser Arg Ala Asn Thr Asp Asp Phe Pro Leu Thr Leu Ala Ser
65 70 75 80

Ala Val Pro Ser Gln Thr Ser Val Tyr Phe Cys Ala Ser Ser Leu Ser
85 90 95

Phe Gly Thr Glu Ala Phe Phe Gly Gln Gly Thr Arg Leu Thr Val Val
100 105 110

Glu Asp Leu Asn Lys Val Phe Pro Pro Glu Val Ala Val Phe Glu Pro
115 120 125

Ser Glu Ala Glu Ile Ser His Thr Gln Lys Ala Thr Leu Val Cys Leu
130 135 140

Ala Thr Gly Phe Phe Pro Asp His Val Glu Leu Ser Trp Trp Val Asn
145 150 155 160

Gly Lys Glu Val His Ser Gly Val Ser Thr Asp Pro Gln Pro Leu Lys
165 170 175

Glu Gln Pro Ala Leu Asn Asp Ser Arg Tyr Cys Leu Ser Ser Arg Leu
180 185 190

Arg Val Ser Ala Thr Phe Trp Gln Asn Pro Arg Asn His Phe Arg Cys
195 200 205

```
Gln Val Gln Phe Tyr Gly Leu Ser Glu Asn Asp Glu Trp Thr Gln Asp
    210                 215                 220

Arg Ala Lys Pro Val Thr Gln Ile Val Ser Ala Glu Ala Trp Gly Arg
225                 230                 235                 240

Ala Cys Gly Phe Thr Ser Ser Tyr Gln Gln Gly Val Leu Ser Ala Thr
                245                 250                 255

Ile Leu Tyr Glu Ile Leu Leu Gly Lys Ala Thr Leu Tyr Ala Val Leu
            260                 265                 270

Val Ser Ala Leu Val Leu Met Ala Met Val Lys Arg Lys Asp Phe
        275                 280                 285


<210> SEQ ID NO 109
<211> LENGTH: 287
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: full length modified F5 TCR beta chain
      comprising TAGS

<400> SEQUENCE: 109

Ile Ala Gly Ile Thr Gln Ala Pro Thr Ser Gln Ile Leu Ala Ala Gly
1               5                   10                  15

Arg Arg Met Thr Leu Arg Cys Thr Gln Asp Met Arg His Asn Ala Met
            20                  25                  30

Tyr Trp Tyr Arg Gln Asp Leu Gly Leu Gly Leu Arg Leu Ile His Tyr
        35                  40                  45

Ser Asn Thr Ala Gly Ser Thr Gly Lys Gly Glu Val Pro Asp Gly Tyr
    50                  55                  60

Ser Val Ser Arg Ala Asn Thr Asp Asp Phe Pro Leu Thr Leu Ala Ser
65                  70                  75                  80

Ala Val Pro Ser Gln Thr Ser Val Tyr Phe Cys Ala Ser Ser Leu Ser
                85                  90                  95

Phe Gly Thr Glu Ala Phe Phe Gly Gln Gly Thr Arg Leu Thr Val Val
            100                 105                 110

Glu Asp Leu Asn Lys Val Phe Pro Pro Glu Val Ala Val Phe Glu Pro
        115                 120                 125

Ser Glu Ala Glu Ile Ser His Thr Gln Lys Ala Thr Leu Val Cys Leu
    130                 135                 140

Ala Thr Gly Phe Phe Pro Asp His Val Glu Leu Ser Trp Trp Val Asn
145                 150                 155                 160

Gly Lys Glu Val His Ser Gly Val Ser Thr Asp Pro Gln Pro Leu Lys
                165                 170                 175

Glu Gln Pro Ala Leu Asn Asp Ser Arg Tyr Cys Leu Ser Ser Arg Leu
            180                 185                 190

Arg Val Ser Ala Thr Phe Trp Gln Asn Pro Arg Asn His Phe Arg Cys
        195                 200                 205

Gln Val Gln Phe Tyr Gly Leu Ser Glu Asn Asp Glu Trp Thr Gln Asp
    210                 215                 220

Arg Ala Lys Pro Val Thr Gln Ile Val Ser Ala Glu Ala Trp Gly Arg
225                 230                 235                 240

Ala Cys Gly Phe Thr Ser Ser Tyr Gln Gln Gly Val Leu Ser Ala Thr
                245                 250                 255

Ile Leu Tyr Glu Ile Leu Leu Gly Lys Ala Thr Leu Tyr Ala Val Leu
            260                 265                 270
```

Val Ser Ala Leu Val Leu Met Ala Met Val Lys Arg Lys Asp Phe
        275                 280                 285

<210> SEQ ID NO 110
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: leader sequence of 1G4 alpha chain

<400> SEQUENCE: 110

Met Glu Thr Leu Leu Gly Leu Leu Ile Leu Trp Leu Gln Leu Gln Trp
1               5                   10                  15

Val Ser Ser

<210> SEQ ID NO 111
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: leader sequence of 1G4 beta chain

<400> SEQUENCE: 111

Met Ser Ile Gly Leu Leu Cys Cys Ala Ala Leu Ser Leu Leu Trp Ala
1               5                   10                  15

Gly Pro Val

<210> SEQ ID NO 112
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: leader sequence of F4 alpha chain

<400> SEQUENCE: 112

Met Leu Leu Glu His Leu Leu Ile Ile Leu Trp Met Gln Leu Thr Trp
1               5                   10                  15

Val Ser

<210> SEQ ID NO 113
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: leader sequence of F4 beta chain

<400> SEQUENCE: 113

Met Gly Thr Arg Leu Phe Phe Tyr Val Ala Leu Cys Leu Leu Trp Thr
1               5                   10                  15

Gly His Met

<210> SEQ ID NO 114
<211> LENGTH: 22

<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: leader sequence of F5 alpha chain

<400> SEQUENCE: 114

```
Met Met Lys Ser Leu Arg Val Leu Leu Val Ile Leu Trp Leu Gln Leu
1               5                   10                  15

Ser Trp Val Trp Ser Gln
            20
```

<210> SEQ ID NO 115
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: leader sequence of F5 beta chain

<400> SEQUENCE: 115

```
Met Arg Ile Arg Leu Leu Cys Cys Val Ala Phe Ser Leu Leu Trp Ala
1               5                   10                  15

Gly Pro Val
```

<210> SEQ ID NO 116
<211> LENGTH: 110
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: variable region of modified F5 TCR beta chain comprising XXGX
<220> FEATURE:
<221> NAME/KEY: misc_feature
<222> LOCATION: (51)..(52)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid

<400> SEQUENCE: 116

```
Ile Ala Gly Ile Thr Gln Ala Pro Thr Ser Gln Ile Leu Ala Ala Gly
1               5                   10                  15

Arg Arg Met Thr Leu Arg Cys Thr Gln Asp Met Arg His Asn Ala Met
            20                  25                  30

Tyr Trp Tyr Arg Gln Asp Leu Gly Leu Gly Leu Arg Leu Ile His Tyr
        35                  40                  45

Ser Asn Xaa Xaa Thr Xaa Lys Gly Glu Val Pro Asp Gly Tyr Ser Val
    50                  55                  60

Ser Arg Ala Asn Thr Asp Asp Phe Pro Leu Thr Leu Ala Ser Ala Val
65                  70                  75                  80

Pro Ser Gln Thr Ser Val Tyr Phe Cys Ala Ser Ser Leu Ser Phe Gly
                85                  90                  95

Thr Glu Ala Phe Phe Gly Gln Gly Thr Arg Leu Thr Val Val
            100                 105                 110
```

<210> SEQ ID NO 117

<211> LENGTH: 113
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: variable region of modified 1G4 TCR beta chain
comprising XXGI
<220> FEATURE:
<221> NAME/KEY: misc_feature
<222> LOCATION: (51)..(52)
<223> OTHER INFORMATION: Xaa can be any naturally occurring amino acid

<400> SEQUENCE: 117

```
Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ser Trp Tyr Arg Gln Asp Pro Gly Met Gly Leu Arg Leu Ile His Tyr
        35                  40                  45

Ser Val Xaa Xaa Gly Ile Thr Asp Gln Gly Glu Val Pro Asn Gly Tyr
    50                  55                  60

Asn Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Ser Tyr Val
                85                  90                  95

Gly Asn Thr Gly Glu Leu Phe Phe Gly Glu Gly Ser Arg Leu Thr Val
            100                 105                 110

Leu
```

<210> SEQ ID NO 118
<211> LENGTH: 113
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (51)..(52)
<223> OTHER INFORMATION: Xaa can be any naturally occurring amino acid

<400> SEQUENCE: 118

```
Asp Ala Gly Ile Thr Gln Ser Pro Arg His Lys Val Thr Glu Thr Gly
1               5                   10                  15

Thr Pro Val Thr Leu Arg Cys His Gln Thr Glu Asn His Arg Tyr Met
            20                  25                  30

Tyr Trp Tyr Arg Gln Asp Pro Gly His Gly Leu Arg Leu Ile His Tyr
        35                  40                  45

Ser Tyr Xaa Xaa Lys Asp Thr Asp Lys Gly Glu Val Ser Asp Gly Tyr
    50                  55                  60

Ser Val Ser Arg Ser Lys Thr Glu Asp Phe Leu Leu Thr Leu Glu Ser
65                  70                  75                  80

Ala Thr Ser Ser Gln Thr Ser Val Tyr Phe Cys Ala Ile Ser Glu Val
                85                  90                  95

Gly Val Gly Gln Pro Gln His Phe Gly Asp Gly Thr Arg Leu Ser Ile
            100                 105                 110

Leu
```

<210> SEQ ID NO 119
<211> LENGTH: 287

<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: full length F5 TCR beta chain comprising XXGX
<220> FEATURE:
<221> NAME/KEY: misc_feature
<222> LOCATION: (51)..(52)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid

<400> SEQUENCE: 119

```
Ile Ala Gly Ile Thr Gln Ala Pro Thr Ser Gln Ile Leu Ala Ala Gly
1               5                   10                  15

Arg Arg Met Thr Leu Arg Cys Thr Gln Asp Met Arg His Asn Ala Met
            20                  25                  30

Tyr Trp Tyr Arg Gln Asp Leu Gly Leu Gly Leu Arg Leu Ile His Tyr
        35                  40                  45

Ser Asn Xaa Xaa Gly Xaa Thr Gly Lys Gly Glu Val Pro Asp Gly Tyr
    50                  55                  60

Ser Val Ser Arg Ala Asn Thr Asp Asp Phe Pro Leu Thr Leu Ala Ser
65                  70                  75                  80

Ala Val Pro Ser Gln Thr Ser Val Tyr Phe Cys Ala Ser Ser Leu Ser
                85                  90                  95

Phe Gly Thr Glu Ala Phe Phe Gly Gln Gly Thr Arg Leu Thr Val Val
            100                 105                 110

Glu Asp Leu Asn Lys Val Phe Pro Pro Glu Val Ala Val Phe Glu Pro
        115                 120                 125

Ser Glu Ala Glu Ile Ser His Thr Gln Lys Ala Thr Leu Val Cys Leu
    130                 135                 140

Ala Thr Gly Phe Phe Pro Asp His Val Glu Leu Ser Trp Trp Val Asn
145                 150                 155                 160

Gly Lys Glu Val His Ser Gly Val Ser Thr Asp Pro Gln Pro Leu Lys
                165                 170                 175

Glu Gln Pro Ala Leu Asn Asp Ser Arg Tyr Cys Leu Ser Ser Arg Leu
            180                 185                 190

Arg Val Ser Ala Thr Phe Trp Gln Asn Pro Arg Asn His Phe Arg Cys
        195                 200                 205

Gln Val Gln Phe Tyr Gly Leu Ser Glu Asn Asp Glu Trp Thr Gln Asp
    210                 215                 220

Arg Ala Lys Pro Val Thr Gln Ile Val Ser Ala Glu Ala Trp Gly Arg
225                 230                 235                 240

Ala Cys Gly Phe Thr Ser Ser Tyr Gln Gln Gly Val Leu Ser Ala Thr
                245                 250                 255

Ile Leu Tyr Glu Ile Leu Leu Gly Lys Ala Thr Leu Tyr Ala Val Leu
            260                 265                 270

Val Ser Ala Leu Val Leu Met Ala Met Val Lys Arg Lys Asp Phe
        275                 280                 285
```

<210> SEQ ID NO 120
<211> LENGTH: 292
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: full length 1G4 beta chain comprising XXGI
<220> FEATURE:
<221> NAME/KEY: misc_feature
<222> LOCATION: (51)..(52)
<223> OTHER INFORMATION: Xaa can be any naturally occurring amino acid

<400> SEQUENCE: 120

```
Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ser Trp Tyr Arg Gln Asp Pro Gly Met Gly Leu Arg Leu Ile His Tyr
        35                  40                  45

Ser Val Xaa Xaa Gly Ile Thr Asp Gln Gly Glu Val Pro Asn Gly Tyr
    50                  55                  60

Asn Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Ser Tyr Val
                85                  90                  95

Gly Asn Thr Gly Glu Leu Phe Phe Gly Glu Gly Ser Arg Leu Thr Val
            100                 105                 110

Leu Glu Asp Leu Lys Asn Val Phe Pro Pro Glu Val Ala Val Phe Glu
        115                 120                 125

Pro Ser Glu Ala Glu Ile Ser His Thr Gln Lys Ala Thr Leu Val Cys
    130                 135                 140

Leu Ala Thr Gly Phe Tyr Pro Asp His Val Glu Leu Ser Trp Trp Val
145                 150                 155                 160

Asn Gly Lys Glu Val His Ser Gly Val Ser Thr Asp Pro Gln Pro Leu
                165                 170                 175

Lys Glu Gln Pro Ala Leu Asn Asp Ser Arg Tyr Ser Leu Ser Ser Arg
            180                 185                 190

Leu Arg Val Ser Ala Thr Phe Trp Gln Asn Pro Arg Asn His Phe Arg
        195                 200                 205

Cys Gln Val Gln Phe Tyr Gly Leu Ser Glu Asn Asp Glu Trp Thr Gln
    210                 215                 220

Asp Arg Ala Lys Pro Val Thr Gln Ile Val Ser Ala Glu Ala Trp Gly
225                 230                 235                 240

Arg Ala Asp Cys Gly Phe Thr Ser Glu Ser Tyr Gln Gln Gly Val Leu
                245                 250                 255

Ser Ala Thr Ile Leu Tyr Glu Ile Leu Leu Gly Lys Ala Thr Leu Tyr
            260                 265                 270

Ala Val Leu Val Ser Ala Leu Val Leu Met Ala Met Val Lys Arg Lys
        275                 280                 285

Asp Ser Arg Gly
    290
```

<210> SEQ ID NO 121
<211> LENGTH: 288
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: full length F4 beta chain comprising XXKD
<220> FEATURE:
<221> NAME/KEY: misc_feature -continued

```
<222> LOCATION: (51)..(52)
<223> OTHER INFORMATION: Xaa can be any naturally occurring amino acid

<400> SEQUENCE: 121

Asp Ala Gly Ile Thr Gln Ser Pro Arg His Lys Val Thr Glu Thr Gly
1               5                   10                  15

Thr Pro Val Thr Leu Arg Cys His Gln Thr Glu Asn His Arg Tyr Met
            20                  25                  30

Tyr Trp Tyr Arg Gln Asp Pro Gly His Gly Leu Arg Leu Ile His Tyr
        35                  40                  45

Ser Tyr Xaa Xaa Lys Asp Thr Asp Lys Gly Glu Val Ser Asp Gly Tyr
    50                  55                  60

Ser Val Ser Arg Ser Lys Thr Glu Asp Phe Leu Leu Thr Leu Glu Ser
65                  70                  75                  80

Ala Thr Ser Ser Gln Thr Ser Val Tyr Phe Cys Ala Ile Ser Glu Val
                85                  90                  95

Gly Val Gly Gln Pro Gln His Phe Gly Asp Gly Thr Arg Leu Ser Ile
            100                 105                 110

Leu Glu Asp Leu Asn Lys Val Phe Pro Pro Glu Val Ala Val Phe Glu
        115                 120                 125

Pro Ser Glu Ala Glu Ile Ser His Thr Gln Lys Ala Thr Leu Val Cys
    130                 135                 140

Leu Ala Thr Gly Phe Phe Pro Asp His Val Glu Leu Ser Trp Trp Val
145                 150                 155                 160

Asn Gly Lys Glu Val His Ser Gly Val Ser Thr Asp Pro Gln Pro Leu
                165                 170                 175

Lys Glu Gln Pro Ala Leu Asn Asp Ser Arg Tyr Cys Leu Ser Ser Arg
            180                 185                 190

Leu Arg Val Ser Ala Thr Phe Trp Gln Asn Pro Arg Asn His Phe Arg
        195                 200                 205

Cys Gln Val Gln Phe Tyr Gly Leu Ser Glu Asn Asp Glu Trp Thr Gln
    210                 215                 220

Asp Arg Ala Lys Pro Val Thr Gln Ile Val Ser Ala Glu Ala Trp Gly
225                 230                 235                 240

Arg Ala Cys Gly Phe Thr Ser Ser Tyr Gln Gln Gly Val Leu Ser Ala
                245                 250                 255

Thr Ile Leu Tyr Glu Ile Leu Leu Gly Lys Ala Thr Leu Tyr Ala Val
            260                 265                 270

Leu Val Ser Ala Leu Val Leu Met Ala Met Val Lys Arg Lys Asp Phe
        275                 280                 285
```

MODIFIED T CELL RECEPTORS AND RELATED MATERIALS AND METHODS

CROSS-REFERENCE TO RELATED APPLICATIONS

This patent application is a Divisional of U.S. patent application Ser. No. 12/443,111, filed Apr. 29, 2009, which is a U.S. National Phase of International Patent Application No. PCT/US07/79487, filed Sep. 26, 2007, which claims the benefit of U.S. Provisional Patent Application No. 60/847,447, filed Sep. 26, 2006, which are incorporated by reference in their entirety herein.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 134,492 Byte ASCII (Text) file named “709180ST25.TXT” dated Nov. 2, 2011.

BACKGROUND OF THE INVENTION

In an ongoing adoptive transfer clinical trial, cancer patients received autologous peripheral blood mononuclear cells (PBMC) that were transduced with nucleic acids encoding a T cell receptor (TCR) specific for the melanoma antigen MART-1. Thus far, two out of 17 patients have demonstrated an objective clinical response (Morgan et al., *Sciencexpress*, e-publication Aug. 31, 2006). The results of this clinical trial demonstrate that normal autologous T lymphocytes, transduced ex vivo with anti-cancer antigen TCR genes and reinfused in cancer patients, can persist and express the transgene long term in vivo and mediate durable regression of large established tumors. However, approaches to increase the expression and function of the transgene are still needed.

There remains a need in the art for modified TCRs for use in treating patients with disease. The invention provides such T cell receptors and methods of treating cancer.

BRIEF SUMMARY OF THE INVENTION

The invention provides a modified T cell receptor (TCR) comprising an amino acid sequence of a wild-type (WT) TCR with no more than three amino acid substitutions, wherein the modified TCR, as compared to the WT TCR, (i) has an enhanced ability to recognize target cells when expressed by $CD4^+$ T cells and (ii) does not exhibit a decrease in antigen specificity when expressed by $CD8^+$ T cells.

The invention also provides related polypeptides and proteins, as well as related nucleic acids, recombinant expression vectors, host cells, and populations of cells. Further provided by the invention are antibodies, or an antigen binding portion thereof, and pharmaceutical compositions relating to the modified TCRs of the invention.

Further, the invention provides a method of detecting a diseased cell in a host, wherein the diseased cell expresses an antigen characteristic of a disease. The method comprises (a) contacting a sample comprising cells of the host with an inventive modified TCR, polypeptide, protein, nucleic acid, recombinant expression vector, host cell, or population of cells, thereby forming a complex between the modified TCR, polypeptide, protein, nucleic acid, recombinant expression vector, host cell, or population of cells and the antigen, and (b) detecting the complex, wherein detection of the complex is indicative of a diseased cell in the host.

Also provided by the invention is a method of treating or preventing a disease in a host. The method comprises administering to the host an inventive pharmaceutical composition in an amount effective to treat or prevent the disease in the host.

A method of identifying a candidate adoptive immunotherapy TCR is also provided. The method consists of (a) producing a nucleic acid encoding a modified TCR comprising a WT TCR amino acid sequence with no more than three amino acid substitutions, (b) expressing the nucleic acid in $CD4^+$ T cells and $CD8^+$ T cells, and (c) assaying the T cells for the ability to recognize target cells and for antigen specificity. A candidate adoptive immunotherapy TCR is identified when the modified TCR, as compared to the WT TCR, (i) has an enhanced ability to recognize target cells when expressed by $CD4^+$ T cells and (ii) does not exhibit a decrease in antigen specificity when expressed by $CD8^+$ T cells.

DETAILED DESCRIPTION OF THE INVENTION

The invention provides a modified T cell receptor (TCR) comprising an amino acid sequence of a wild-type (WT) TCR with no more than three amino acid substitutions, (e.g., 1, 2, or 3) wherein the modified TCR, as compared to the WT TCR, (i) has an enhanced ability to recognize target cells when expressed by $CD4^+$ T cells and (ii) does not exhibit a decrease in antigen specificity when expressed by $CD8^+$ T cells.

The term “wild-type” as used herein refers to a TCR which is naturally expressed by a T cell of a host, e.g., a TCR which is endogenous to a T cell of a host. Nucleic acids encoding wild-type TCRs are known in the art and can be obtained from the GenBank database of the National Center for Biotechnology Information (NCBI). For example, wild-type TCR nucleic acid sequences are available as GenBank Accession Nos. NG_001333, NG_000016, NG_001337, NG_001332, NG_001336, AF043179, HSJ004872, M13863, Z81026, AF397440, AY124793, and the like. Also, nucleic acids encoding wild-type TCRs can be obtained by methods known in the art, such as the PCR-based method described herein (see Example 1). The cells used to obtain the nucleic acids encoding the wild-type TCR are not limited to those used in Example 1. Rather, the cells can be any of the T cells described herein. In addition, the wild-type TCR can be entirely synthesized using oligonucleotide primers corresponding to the known sequence.

The modified TCR of the invention is marked by one or more enhanced biological properties when expressed in T cells. Specifically, the modified TCR, when compared to the corresponding WT TCR, (i) has an enhanced ability to recognize target cells when expressed by $CD4^+$ T cells and (ii) does not exhibit a decrease in antigen specificity when expressed by $CD8^+$ T cells. The term “target cells” as used herein refers to cells which express and present, by way of an MHC molecule, the antigen which is specifically recognized by the modified TCR. The phrase “recognize target cells” as used herein refers to the ability of the modified TCR to immunologically recognize (e.g., specifically bind to) an antigen which is expressed and presented by a target cell. The term “enhanced” as used herein means that the modified TCR of the invention consistently exhibits at least twice the ability to recognize antigen expressed and presented by target cells, as compared to its WT counterpart. Preferably, the modified TCR of the invention recognizes antigen expressed and presented by target cells at least five times better than its WT counterpart. More preferably, the modified TCRs of the invention recognize antigen at least ten times better than its WT counterpart. Most preferably, the modified TCRs of the invention recognize antigen at least 2 times better than its WT counterpart.

The enhanced properties exhibited by the modified TCR consistently exhibits the properties, e.g., ability to recognize antigen expressed and presented by target cells. By "consistently" is meant that the modified TCR of the invention exhibits the enhanced properties in at least two assays. Preferably, the TCR of the invention exhibits the enhanced properties in at least three assays (e.g., in five or more assays, or in ten or more assays).

The modified TCR of the invention exhibits an enhanced ability to recognize target cells without exhibiting a decrease in antigen specificity when expressed by $CD8^+$ T cells. In this respect, the modified TCR is said to retain the antigen specificity of the counterpart WT TCR, e.g., recognizes only the antigen(s) recognized by the WT TCR and does not recognize antigen(s) that are not recognized by the WT TCR.

Methods of testing a TCR for the ability to recognize target cells and for antigen specificity are known in the art. For instance, Clay et al., *J. Immunol.,* 163: 507-513 (1999), teaches methods of measuring the release of cytokines (e.g., interferon-γ, granulocyte/monocyte colony stimulating factor (GM-CSF), tumor necrosis factor a (TNF-α) or interleukin 2 (IL-2)). In addition, TCR function can be evaluated by measurement of cellular cytoxicity, as described in Zhao et al., *J. Immunol.,* 174: 4415-4423 (2005). Methods of testing a modified TCR for the ability to recognize target cells and for antigen specificity are described herein as Examples 2 to 4.

The modified TCR of the invention can have antigen specificity for any antigen. The phrase "have antigen specificity" as used herein means that the modified TCR can specifically bind to and immunologically recognize an antigen, such that binding of the TCR to the antigen elicits an immune response.

Preferably, the modified TCR of the invention has antigen specificity for an antigen which is characteristic of a disease. The disease can be any disease involving an antigen, as discussed herein, e.g., an infectious disease, an autoimmune disease, or a cancer. The antigen could be, for example, a viral antigen, a bacterial antigen, a cancer antigen, etc.

More preferably, the modified TCR of the invention has antigen specificity for a cancer antigen. The term "cancer antigen" as used herein refers to any molecule (e.g., protein, peptide, lipid, carbohydrate, etc.) solely or predominantly expressed or over-expressed by a tumor cell or cancer cell, such that the antigen is associated with the tumor or cancer. The cancer antigen additionally can be expressed by normal, non-tumor, or non-cancerous cells. However, in such a situation, the expression of the cancer antigen by normal, non-tumor, or non-cancerous cells is not as robust as the expression by tumor or cancer cells. In this regard, the tumor or cancer cells can over-express the antigen or express the antigen at a significantly higher level, as compared to the expression of the antigen by normal, non-tumor, or non-cancerous cells. Also, the cancer antigen additionally can be expressed by cells of a different state of development or maturation. For instance, the cancer antigen can be additionally expressed by cells of the embryonic or fetal stage, which cells are not normally found in an adult host. Alternatively, the cancer antigen additionally can be expressed by stem cells or precursor cells, which cells are not normally found in an adult host. Another group of cancer antigens are represented by the differentiation antigens that are expressed in only a limited set of tissues in the adult, such as the melanocytes differentiation antigens, whose expression is limited to normal melanocytes. Although it is not known why these molecules elicit immune responses, the limited expression pattern of these proteins may allow these molecules to be recognized by the immune system.

The cancer antigen can be an antigen expressed by any cell of any cancer or tumor, including the cancers and tumors described herein. The cancer antigen may be a cancer antigen of only one type of cancer or tumor, such that the cancer antigen is associated with or characteristic of only one type of cancer or tumor. Alternatively, the cancer antigen may be a cancer antigen (e.g., may be characteristic) of more than one type of cancer or tumor. For example, the cancer antigen may be expressed by both breast and prostate cancer cells and not expressed at all by normal, non-tumor, or non-cancer cells. In a preferred embodiment of the invention, the cancer antigen is a melanoma cancer antigen. In a more preferred embodiment, the cancer antigen is selected from the group consisting of NY-ESO-1, MART-1, gp100, p53, TRP-1, TRP-2, and tyrosinase. In a most preferred embodiment, the cancer antigen is NY-ESO-1 or MART-1.

With respect to the inventive modified TCR, the amino acid substitution(s) can be located in any part of the amino acid sequence of the TCR. Preferably, the amino acid substitutions are located within the amino acid sequence of the complementary determining region (CDR) of the TCR, which are known in the art. These regions have been defined by elucidation of X-ray crystallographic structures, as well as sequence comparisons which have revealed the presence of regions of high diversity encoded in germline sequences, in the case of CDR1 and CDF2 regions, as well as recombinational diversity, in the case of CDR3 region (Lefranc et al., *Nucl. Acids Res.,* 27, 209-212 (1999)). Preferably, the one, two, or three amino acid substitutions are located in the amino acid sequence of a CDR2 or CDR3 of the TCR (e.g., in the CDR2 region of the beta chain of the TCR). More preferably, the amino acid substitutions are located in the amino acid sequence of a CDR2, e.g., CDR2 of an a chain of a TCR or a β chain of a TCR. Most preferably, the amino acid substitutions are located in the CDR2 of a β chain of a TCR. For example, the modified TCR can comprise an amino acid sequence selected from the group consisting of SEQ ID NOs: 116 to 121 in which the amino acid substitutions are located at the Xaa's of these sequences.

The invention provides a modified TCR comprising two polypeptides (i.e., polypeptide chains), such as an α chain of a TCR, a β chain of a TCR, a γ chain of a TCR, a δ chain of a TCR, or a combination thereof. The amino acid substitutions of the inventive modified TCRs can be located in the amino acid sequence of either or both polypeptide chains which constitute the TCR. In a preferred embodiment of the invention, the amino acid substitutions are located in the amino acid sequence of the β chain of the modified TCR. In a more preferred embodiment, the amino acid substitutions are located in only the amino acid sequence of the β chain of the modified TCR.

The amino acid substitutions of the inventive modified TCR are preferably conservative amino acid substitutions. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc. Preferably, the conservative amino acid substitutions are selected from the group consisting of T→A, G→A, A→I, T→V, A→M, T→I, A→V, T→G, and T→S.

The polypeptide chains of the inventive modified TCR can comprise any amino acid sequence, provided that the modified TCR, as compared to the WT TCR, (i) has an enhanced ability to recognize antigen when expressed by $CD4^+$ T cells and (ii) does not exhibit a decrease in antigen specificity when expressed by $CD8^+$ T cells.

In a preferred embodiment of the invention, the modified TCR comprises the amino acid sequence of SEQ ID NO: 8 with no more than three amino acid substitutions. In a more preferred embodiment of the invention, the modified TCR comprises the amino acid sequence of SEQ ID NO: 1, SEQ ID NO: 2, or SEQ ID NO: 3, each of which is an amino acid sequence of a variable region of a beta chain of a modified TCR which recognizes the cancer antigen NY-ESO-1. In a most preferred embodiment of the invention, the modified TCR comprises the amino acid sequence of SEQ ID NO: 14, 15, or 16, each of which is the amino acid sequence of a full-length beta chain comprising a constant region and a variable region. The modified TCR can additionally comprise the amino acid sequence of SEQ ID NO: 7, which is the WT alpha chain of the 1G4 NY-ESO-1-specific TCR.

In another preferred embodiment, the modified TCR comprises the amino acid sequence of SEQ ID NO: 10 or SEQ ID NO: 12 with no more than three amino acid substitutions. In a more preferred embodiment, the modified TCR comprises an amino acid sequence selected from the group consisting of SEQ ID NO: 4 to 6, 13, and 95 to 103, each of which is an amino acid sequence of a variable region of a beta chain of a modified TCR which recognizes the cancer antigen MART-1. In a most preferred embodiment of the invention, the modified TCR comprises the amino acid sequence of any of SEQ ID NOs: 17 to 20, 37 to 39, and 104 to 109, each of which is the amino acid sequence of a full-length beta chain comprising a constant region and a variable region. The modified TCR can additionally comprise the amino acid sequence of SEQ ID NO: 9 or SEQ ID NO: 11.

Preferably, when the modified TCR comprises the amino acid sequence of SEQ ID NO: 10 with no more than three amino acid substitutions, the modified TCR comprises the amino acid sequence of any of SEQ ID NOs: 4, 13, and 95 to 103. More preferably, the modified TCR comprises the amino acid sequence of any of SEQ ID NOs: 17, 20, 37 to 39, and 104 to 109. Also, in these instances, it is preferred that the modified TCR additionally comprises the amino acid sequence of SEQ ID NO: 9, which is the WT alpha chain of the F5 MART-1-specific TCR.

Likewise, when the modified TCR comprises the amino acid sequence of SEQ ID NO: 12 with no more than three amino acid substitutions, the modified TCR preferably comprises SEQ ID NO: 5 or SEQ ID NO: 6. More preferably, the modified TCR comprises the amino acid sequence of SEQ ID NO: 18 or 19. Also, in these instances, it is preferred that the modified TCR additionally comprises the amino acid sequence of SEQ ID NO: 11, which is the WT alpha chain of the F4 MART-1-specific TCR.

In a preferred embodiment, the modified TCR comprises an amino acid sequence of (i) any one of SEQ ID NOs: 17, 20, 37 to 39, and 104 to 109 and SEQ ID NO: 9, (ii) SEQ ID NO: 18 or 19 and SEQ ID NO: 11, or (iii) SEQ ID NO: 14, 15, or 16 and SEQ ID NO: 7. Such modified TCRs comprise the amino acid sequences of a mutated β chain and a WT a chain of a TCR which recognizes either NY-ESO-1 or MART-1.

The modified TCRs of the invention can comprise one or more immature TCR chains comprising a leader sequence or one or more mature chains in which the leader sequence has been cleaved off. As one of ordinary skill in the art appreciates, the leader sequence of a TCR chain comprises the amino acids at the N-terminus which together serve as a signal to transport the TCR to the plasma membrane and which amino acids are cleaved off to yield the mature form of the TCR. In this regard, the modified TCRs described herein can additionally comprise a leader sequence selected from the group consisting of SEQ ID NOs: 110-115. Preferably, when the modified TCR comprises SEQ ID NO: 7, the modified TCR comprises the leader sequence of SEQ ID NO: 110; when the modified TCR comprises any of SEQ ID NOs: 1-3, 8, and 14-16, the modified TCR comprises the leader sequence of SEQ ID NO: 111; when the modified TCR comprises SEQ ID NO: 11, the modified TCR comprises the leader sequence of SEQ ID NO: 112; when the modified TCR comprises any of SEQ ID NOs: 5, 6, 12, 18, and 19, the modified TCR comprises the leader sequence of SEQ ID NO: 113; when the modified TCR comprises SEQ ID NO: 9, the modified TCR comprises the leader sequence of SEQ ID NO: 114; when the modified TCR comprises any of SEQ ID NOs: 4, 10, 13, 17, 20, 37-39, and 95-109, the modified TCR comprises the leader sequence of SEQ ID NO: 115.

Also provided by the invention is an isolated or purified polypeptide comprising a functional portion of any of the modified TCRs described herein, wherein the functional portion comprises the amino acid substitutions. The term "polypeptide" as used herein includes oligopeptides and refers to a single chain of amino acids connected by one or more peptide bonds.

With respect to the inventive polypeptides, the functional portion can be any portion comprising contiguous amino acids of the modified TCR of which it is a part, provided that the functional portion comprises the amino acid substitutions. The term "functional portion" when used in reference to a modified TCR refers to any part or fragment of the modified TCR of the invention, which part or fragment retains the biological activity of the modified TCR of which it is a part (the parent modified TCR). Functional portions encompass, for example, those parts of a modified TCR that retain the ability to recognize target cells, or detect, treat, or prevent a disease, to a similar extent, the same extent, or to a higher extent, as the parent modified TCR. In reference to the parent modified TCR, the functional portion can comprise, for instance, about 10%, 25%, 30%, 50%, 68%, 80%, 90%, 95%, or more, of the parent TCR.

The functional portion can comprise additional amino acids at the amino or carboxy terminus of the portion, or at both termini, which additional amino acids are not found in the amino acid sequence of the parent modified TCR. Desirably, the additional amino acids do not interfere with the biological function of the functional portion, e.g., recognize target cells, detect cancer, treat or prevent cancer, etc. More desirably, the additional amino acids enhance the biological activity, as compared to the biological activity of the parent modified TCR.

The polypeptide can comprise a functional portion of either or both of the α and β chains of the TCRs of the invention, such as a functional portion comprising one of more of CDR1, CDR2, and CDR3 of the variable region(s) of the α chain and/or β chain of a TCR of the invention. In this regard, the polypeptide can comprise the amino acid sequence of any of SEQ ID NOs: 1 to 6, 13, and 95 to 103. The polypeptides can additionally comprise an amino acid sequence selected from the group consisting of SEQ ID NOs: 7, 9, and 11.

Alternatively or additionally, the inventive polypeptide can comprise the entire length of an α or β chain of one of the modified TCRs described herein. In this regard, the inventive polypeptide can comprise an amino acid sequence selected from the group consisting of any of SEQ ID NOs: 14 to 20, 37 to 39, and 104 to 109. Alternatively, the polypeptide of the invention can comprise both chains of the TCRs described herein. For example, the inventive polypeptide can comprise: (i) any of SEQ ID NOs: 14 to 16 in combination with SEQ ID NO: 7; (ii) any of SEQ ID NOs: 17, 20, 37 to 39, and 104 to 109 in combination with SEQ ID NO: 9; or (iii) SEQ ID NO: 18 or 19 in combination with SEQ ID NO: 11.

The invention further provides an isolated or purified protein comprising at least one of the inventive polypeptides described herein. By "protein" is meant a molecule comprising one or more polypeptide chains.

The protein of the invention can comprise (i) a first polypeptide chain comprising the amino acid sequence of SEQ ID NO: 1, 2, or 3 and a second polypeptide chain comprising the amino acid sequence of SEQ ID NO: 7, (ii) a first polypeptide chain comprising the amino acid sequence of any of SEQ ID NOs: 4, 13, and 95 to 103 and a second polypeptide chain comprising the amino acid sequence of SEQ ID NO: 9, or (iii) a first polypeptide chain comprising the amino acid sequence of SEQ ID NO: 5 or 6 and a second polypeptide chain comprising the amino acid sequence of SEQ ID NO: 11. In this instance, the protein of the invention can be a TCR.

Alternatively, if, for example, the protein comprises a single polypeptide chain comprising SEQ ID NO: 1 and SEQ ID NO: 7, or if the first and/or second polypeptide chain(s) of the protein further comprise(s) other amino acid sequences, e.g., an amino acid sequence encoding an immunoglobulin or a portion thereof, then the inventive protein can be a fusion protein. In this regard, the invention also provides a fusion protein comprising at least one of the inventive polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide can encode any peptidic or proteinaceous molecule, or a portion thereof, including, but not limited to an immunoglobulin, CD3, CD4, CD8, an MHC molecule, etc.

The fusion protein can comprise one or more copies of the inventive polypeptide and/or one or more copies of the other polypeptide. For instance, the fusion protein can comprise 1, 2, 3, 4, 5, or more, copies of the inventive polypeptide and/or of the other polypeptide. Suitable methods of making fusion proteins are known in the art, and include, for example, recombinant methods. See, for instance, Choi et al., *Mol. Biotechnol.* 31: 193-202 (2005).

The protein of the invention can be a recombinant antibody comprising at least one of the inventive polypeptides described herein. As used herein, "recombinant antibody" refers to a recombinant (e.g., genetically engineered) protein comprising at least one of the polypeptides of the invention and a polypeptide chain of an antibody, or a portion thereof. The polypeptide of an antibody, or portion thereof, can be a heavy chain, a light chain, a variable or constant region of a heavy or light chain, a single chain variable fragment (scFv), or an Fc, Fab, or $F(ab)_2'$ fragment of an antibody, etc. The polypeptide chain of an antibody, or portion thereof, can exist as a separate polypeptide of the recombinant antibody. Alternatively, the polypeptide chain of an antibody, or portion thereof, can exist as a polypeptide, which is expressed in frame (in tandem) with the polypeptide of the invention. The polypeptide of an antibody, or portion thereof, can be a polypeptide of any antibody or any antibody fragment, including any of the antibodies and antibody fragments described herein.

Included in the scope of the invention are functional variants of the inventive modified TCRs, polypeptides, and proteins described herein. The term "functional variant" as used herein refers to a modified TCR, polypeptide, or protein having substantial or significant sequence identity or similarity to a parent modified TCR, polypeptide, or protein, which functional variant retains the biological activity of the modified TCR, polypeptide, or protein of which it is a variant. Functional variants encompass, for example, those variants of the TCR, polypeptide, or protein described herein (the parent modified TCR, polypeptide, or protein) that retain the ability to recognize target cells to a similar extent, the same extent, or to a higher extent, as the parent modified TCR, polypeptide, or protein. In reference to the parent modified TCR, polypeptide, or protein, the functional variant can, for instance, be at least about 30%, 50%, 75%, 80%, 90%, 98% or more identical in amino acid sequence to the parent modified TCR, polypeptide, or protein.

The functional variant can, for example, comprise the amino acid sequence of the parent TCR, polypeptide, or protein with at least one conservative amino acid substitution. Alternatively or additionally, the functional variants can comprise the amino acid sequence of the parent modified TCR, polypeptide, or protein with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the parent modified TCR, polypeptide, or protein.

The modified TCR, polypeptide, or protein can consist essentially of the specified amino acid sequence or sequences described herein, such that other components of the functional variant, e.g., other amino acids, do not materially change the biological activity of the functional variant. In this regard, the inventive modified TCR, polypeptide, or protein can, for example, consist essentially of an amino acid sequence selected from the group consisting of SEQ ID NOs: 1 to 6, 13, and 95 to 103. Also, for instance, the inventive modified TCRs, polypeptides, or proteins can consist essentially of an amino acid sequence selected from the group consisting of SEQ ID NOs: 14 to 20, 37 to 39, and 104 to 109.

The modified TCRs, polypeptides, and proteins of the invention (including functional portions and functional variants) can be of any length, i.e., can comprise any number of amino acids, provided that the modified TCRs, polypeptides, or proteins (or functional portions or functional variants thereof) retain their biological activity, e.g., the ability to specifically bind to antigen, detect diseased cells in a host, or treat or prevent disease in a host, etc. For example, the polypeptide can be 50 to 5000 amino acids long, such as 50, 70, 75, 100, 125, 150, 175, 200, 300, 400, 500, 600, 700, 800, 900, 1000 or more amino acids in length. In this regard, the polypeptides of the invention also include oligopeptides.

The modified TCRs, polypeptides, and proteins of the invention (including functional portions and functional variants) of the invention can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The modified TCRs, polypeptides, and proteins of the invention (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

When the modified TCRs, polypeptides, and proteins of the invention (including functional portions and functional variants) are in the form of a salt, preferably, the polypeptides are in the form of a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

The modified TCR, polypeptide, and/or protein of the invention (including functional portions and functional variants thereof) can be obtained by methods known in the art. Suitable methods of de novo synthesizing polypeptides and proteins are described in references, such as Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; *Epitope Mapping*, ed. Westwoood et al., Oxford University Press, Oxford, United Kingdom, 2000; and U.S. Pat. No. 5,449,752. Also, polypeptides and proteins can be recombinantly produced using the nucleic acids described herein using standard recombinant methods. See, for instance, Sambrook et al., *Molecular Cloning: A Laboratory Manual*, 3rd ed., Cold Spring Harbor Press, Cold Spring Harbor, N.Y. 2001; and Ausubel et al., *Current Protocols in Molecular Biology*, Greene Publishing Associates and John Wiley & Sons, NY, 1994. Further, some of the TCRs, polypeptides, and proteins of the invention (including functional portions and functional variants thereof) can be isolated and/or purified from a source, such as a plant, a bacterium, an insect, a mammal, e.g., a rat, a human, etc. Methods of isolation and purification are well-known in the art. Alternatively, the TCRs, polypeptides, and/or proteins described herein (including functional portions and functional variants thereof) can be commercially synthesized by companies, such as Synpep (Dublin, Calif.), Peptide Technologies Corp. (Gaithersburg, Md.), and Multiple Peptide Systems (San Diego, Calif.). In this respect, the inventive TCRs, polypeptides, and proteins can be synthetic, recombinant, isolated, and/or purified.

Included in the scope of the invention are conjugates, e.g., bioconjugates, comprising any of the inventive modified TCRs, polypeptides, or proteins (including any of the functional portions or variants thereof), nucleic acids, recombinant expression vectors, host cells, populations of host cells, or antibodies, or antigen binding portions thereof. Conjugates, as well as methods of synthesizing conjugates in general, are known in the art (See, for instance, Hudecz, F., *Methods Mol. Biol.* 298: 209-223 (2005) and Kirin et al., *Inorg Chem.* 44(15): 5405-5415 (2005)).

Further provided by the invention is a nucleic acid comprising a nucleotide sequence encoding any of the modified TCRs, polypeptides, or proteins described herein (including functional portions and functional variants thereof).

By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl)uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleic acid can comprise any nucleotide sequence which encodes any of the modified TCRs, polypeptides, or proteins, or functional portions or functional variants thereof. For example, the nucleic acid can comprise a nucleotide sequence comprising SEQ ID NO: 22 to 24, 28, 29, 32, or 33.

The nucleotide sequence alternatively can comprise a nucleotide sequence which is degenerate to any of these sequences or a combination of degenerate sequences. For example, the nucleotide sequence can comprise a nucleotide sequence comprising a nucleotide sequence degenerate to SEQ ID NO: 22 and a nucleotide sequence degenerate to SEQ ID NO: 23 or comprising a nucleotide sequence degenerate to SEQ ID NO: 23 and a nucleotide sequence degenerate to SEQ ID NO: 25.

The invention also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive TCRs. It is generally appreciated that conditions can be rendered more stringent by the addition of increasing amounts of formamide.

The nucleic acids of the invention can be incorporated into a recombinant expression vector. In this regard, the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages does not hinder the transcription or replication of the vector.

The recombinant expression vector of the invention can be any suitable recombinant expression vector, and can be used to transform or transfect any suitable host. Suitable vectors include those designed for propagation and expansion or for expression or both, such as plasmids and viruses. The vector can be selected from the group consisting of the pUC series (Fermentas Life Sciences), the pBluescript series (Stratagene, Jolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM and pMAMneo (Clontech). Preferably, the recombinant expression vector is a viral vector, e.g., a retroviral vector.

The recombinant expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColEl, 2μ plasmid, λ, SV40, bovine papilloma virus, and the like.

Desirably, the recombinant expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or normative promoter operably linked to the nucleotide sequence encoding the modified TCR, polypeptide, or protein (including functional portions and functional variants thereof), or to the nucleotide sequence which is complementary to or which hybridizes to the nucleotide sequence encoding the modified TCR, polypeptide, or protein. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, *Suicide Gene Therapy: Methods and Reviews*, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

The invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α *E. coli* cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH5α cell. For purposes of producing a recombinant modified TCR, polypeptide, or protein, the host cell is preferably a mammalian cell. Most preferably, the host cell is a human cell. While the host cell can be of any cell type, can originate from any type of tissue, and can be of any developmental stage, the host cell preferably is a peripheral blood lymphocyte (PBL). More preferably, the host cell is a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. Preferably, the T cell is a human T cell. More preferably, the T cell is a T cell isolated from a human. The T cell can be any type of T cell and can be of any developmental stage, including but not limited to, $CD4^+/CD8^+$ double positive T cells, $CD4^+$ helper T cells, e.g., $Th_1$ and $Th_2$ cells, $CD8^+$ T cells (e.g., cytotoxic T cells), peripheral blood mononuclear cells (PBMCs), peripheral blood leukocytes (PBLs), tumor infiltrating cells (TILs), memory T cells, naïve T cells, and the like. Preferably, the T cell is a $CD8^+$ T cell or a $CD4^+$ T cell.

Also provided by the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cells, a muscle cell, a brain cell, etc. Alternatively, the population of cells can be a substantially homogeneous population, in which the population comprises mainly of host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

The invention further provides an antibody, or antigen binding portion thereof, which specifically binds to an epitope of the modified TCR of the invention, wherein the epitope comprises the amino acid substitutions. The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. Also, the antibody can have any level of affinity or avidity for the functional portion of the inventive modified TCR. Desirably, the antibody is specific for the epitope of the inventive modified TCR comprising the amino acid substitutions, such that there is minimal cross-reaction with other peptides or proteins.

Methods of testing antibodies for the ability to bind to any functional portion of the inventive modified TCR are known in the art and include any antibody-antigen binding assay, such as, for example, radioimmunoassay (RIA), ELISA, Western blot, immunoprecipitation, and competitive inhibition assays (see, e.g., Janeway et al., infra, and U.S. Patent Application Publication No. 2002/0197266 A1).

Suitable methods of making antibodies are known in the art. For instance, standard hybridoma methods are described in, e.g., Köhler and Milstein, *Eur. J. Immunol.,* 5, 511-519 (1976), Harlow and Lane (eds.), *Antibodies: A Laboratory Manual*, CSH Press (1988), and C. A. Janeway et al. (eds.), *Immunobiology,* 5$^{th}$ Ed., Garland Publishing, New York, N.Y. (2001)). Alternatively, other methods, such as EBV-hybridoma methods (Haskard and Archer, *J. Immunol. Methods,* 74(2), 361-67 (1984), and Roder et al., *Methods Enzymol.,* 121, 140-67 (1986)), and bacteriophage vector expression systems (see, e.g., Huse et al., *Science,* 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1).

Phage display furthermore can be used to generate the antibody of the invention. In this regard, phage libraries encoding antigen-binding variable (V) domains of antibodies can be generated using standard molecular biology and recombinant DNA techniques (see, e.g., Sambrook et al. (eds.), *Molecular Cloning, A Laboratory Manual,* 3$^{rd}$ Edition, Cold Spring Harbor Laboratory Press, New York (2001)). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150).

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are well known in the art and are described in detail in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., *J. Mol. Biol.,* 235, 959-973 (1994).

The invention also provides antigen binding portions of any of the antibodies described herein. The antigen binding portion can be any portion that has at least one antigen binding site, such as Fab, $F(ab')_2$, dsFv, sFv, diabodies, and triabodies.

A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., *Protein Engineering,* 7, 697-704 (1994)). Antibody fragments of the invention, however, are not limited to these exemplary types of antibody fragments.

Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

The inventive modified TCRs, polypeptides, proteins, (including functional portions and functional variants thereof), nucleic acids, recombinant expression vectors, host cells (including populations thereof), and antibodies (including antigen binding portions thereof), can be isolated and/or purified. The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than 60%, 70% or 80%, or can be 100%.

The inventive modified TCRs, polypeptides, proteins (including functional portions and variants thereof), nucleic acids, recombinant expression vectors, host cells (including populations thereof), and antibodies (including antigen binding portions thereof), all of which are collectively referred to as "inventive TCR materials" hereinafter, can be formulated into a composition, such as a pharmaceutical composition. In this regard, the invention provides a pharmaceutical composition comprising any of the modified TCRs, polypeptides, proteins, functional portions, functional variants, nucleic acids, expression vectors, host cells (including populations thereof), and antibodies (including antigen binding portions thereof), and a pharmaceutically acceptable carrier. The inventive pharmaceutical compositions containing any of the inventive TCR materials can comprise more than one inventive TCR material, e.g., a polypeptide and a nucleic acid, or two or more different modified TCRs. Alternatively, the pharmaceutical composition can comprise an inventive TCR material in combination with another pharmaceutically active agents or drugs, such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

With respect to pharmaceutical compositions, the pharmaceutically acceptable carrier can be any of those conventionally used and is limited only by chemico-physical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular inventive TCR material, as well as by the particular method used to administer the inventive TCR material. Accordingly, there are a variety of suitable formulations of the pharmaceutical composition of the invention. The following formulations for oral, aerosol, parenteral, subcutaneous, intravenous, intramuscular, intraarterial, intrathecal, interperitoneal, rectal, and vaginal administration are exemplary and are in no way limiting. More than one route can be used to administer the inventive TCR materials, and in certain instances, a particular route can provide a more immediate and more effective response than another route.

Topical formulations are well-known to those of skill in the art. Such formulations are particularly suitable in the context of the invention for application to the skin.

Formulations suitable for oral administration can consist of (a) liquid solutions, such as an effective amount of the inventive TCR material dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the inventive TCR material in a flavor, usually sucrose and acacia or tragacanth, as well as pastilles comprising the inventive TCR material in an inert base, such as gelatin and glycerin, or sucrose and acacia, emulsions, gels, and the like containing, in addition to, such excipients as are known in the art.

The inventive TCR material, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The inventive TCR material can be administered in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1,3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the inventive TCR material in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Injectable formulations are in accordance with the invention. The requirements for effective pharmaceutical carriers for injectable compositions are well-known to those of ordinary skill in the art (see, e.g., *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Toissel, 4th ed., pages 622-630 (1986)). Preferably, when administering cells, e.g., dendritic cells, the cells are administered via injection.

Additionally, the inventive TCR materials, or compositions comprising such inventive TCR materials, can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

It will be appreciated by one of skill in the art that, in addition to the above-described pharmaceutical compositions, the inventive TCR materials of the invention can be formulated as inclusion complexes, such as cyclodextrin inclusion complexes, or liposomes.

For purposes of the invention, the amount or dose of the inventive TCR material administered should be sufficient to effect, e.g., a therapeutic or prophylactic response, in the subject or animal over a reasonable time frame. For example, the dose of the inventive TCR material should be sufficient to bind to antigen, or detect, treat or prevent disease in a period of from about 2 hours or longer, e.g., 12 to 24 or more hours, from the time of administration. In certain embodiments, the time period could be even longer. The dose will be determined by the efficacy of the particular inventive TCR material and the condition of the animal (e.g., human), as well as the body weight of the animal (e.g., human) to be treated.

Many assays for determining an administered dose are known in the art. For purposes of the invention, an assay, which comprises comparing the extent to which target cells are lysed or IFN-γ is secreted by T cells expressing the inventive modified TCR, polypeptide, or protein upon administration of a given dose of such T cells to a mammal among a set of mammals of which is each given a different dose of the T cells, could be used to determine a starting dose to be administered to a mammal. The extent to which target cells are lysed or IFN-γ is secreted upon administration of a certain dose can be assayed by methods known in the art, including, for instance, the methods described herein as Example 2.

The dose of the inventive TCR material also will be determined by the existence, nature and extent of any adverse side effects that might accompany the administration of a particular inventive TCR material. Typically, the attending physician will decide the dosage of the inventive TCR material with which to treat each individual patient, taking into consideration a variety of factors, such as age, body weight, general health, diet, sex, inventive TCR material to be administered, route of administration, and the severity of the condition being treated. By way of example and not intending to limit the invention, the dose of the inventive TCR material can be about 0.001 to about 1000 mg/kg body weight of the subject being treated/day, from about 0.01 to about 10 mg/kg body weight/day, about 0.01 mg to about 1 mg/kg body weight/day.

One of ordinary skill in the art will readily appreciate that the inventive TCR materials of the invention can be modified in any number of ways, such that the therapeutic or prophylactic efficacy of the inventive TCR materials is increased through the modification. For instance, the inventive TCR materials can be conjugated either directly or indirectly through a linker to a targeting moiety. The practice of conjugating compounds, e.g., inventive TCR materials, to targeting moieties is known in the art. See, for instance, Wadwa et al., *J. Drug Targeting* 3: 111 (1995) and U.S. Pat. No. 5,087,616. The term "targeting moiety" as used herein, refers to any molecule or agent that specifically recognizes and binds to a cell-surface receptor, such that the targeting moiety directs the delivery of the inventive TCR materials to a population of cells on which surface the receptor is expressed. Targeting moieties include, but are not limited to, antibodies, or fragments thereof, peptides, hormones, growth factors, cytokines, and any other natural or non-natural ligands, which bind to cell surface receptors (e.g., Epithelial Growth Factor Receptor (EGFR), T-cell receptor (TCR), B-cell receptor (BCR), CD28, Platelet-derived Growth Factor Receptor (PDGF), nicotinic acetylcholine receptor (nAChR), etc.). The term "linker" as used herein, refers to any agent or molecule that bridges the inventive TCR materials to the targeting moiety. One of ordinary skill in the art recognizes that sites on the inventive TCR materials, which are not necessary for the function of the inventive TCR materials, are ideal sites for attaching a linker and/or a targeting moiety, provided that the linker and/or targeting moiety, once attached to the inventive TCR materials, do(es) not interfere with the function of the inventive TCR materials, i.e., the ability to bind to antigen, or to detect, treat, or prevent disease.

Alternatively, the inventive TCR materials can be modified into a depot form, such that the manner in which the inventive TCR materials is released into the body to which it is administered is controlled with respect to time and location within the body (see, for example, U.S. Pat. No. 4,450,150). Depot forms of inventive TCR materials can be, for example, an implantable composition comprising the inventive TCR materials and a porous or non-porous material, such as a polymer, wherein the inventive TCR materials is encapsulated by or diffused throughout the material and/or degradation of the non-porous material. The depot is then implanted into the desired location within the body and the inventive TCR materials are released from the implant at a predetermined rate.

It is contemplated that the inventive pharmaceutical compositions, modified TCRs, polypeptides, proteins, nucleic acids, recombinant expression vectors, host cells, or populations of cells can be used in methods of treating or preventing a disease in a host. Without being bound to a particular theory, the inventive modified TCRs are believed to have enhanced biological activity, e.g., ability to recognize antigen, such that the modified TCR (or related inventive polypeptide or protein) when expressed by a cell is able to mediate a stronger immune response against the cell expressing the antigen for which the modified TCR is specific. In this regard, the invention provides a method of treating or preventing a disease in a host, comprising administering to the host any of the pharmaceutical compositions in an amount effective to treat or prevent the disease in the host.

The disease can be any disease involving an antigen, e.g., an infectious disease, an autoimmune disease, a cancer.

For purposes herein, "infectious disease" means a disease that can be transmitted from person to person or from organism to organism, and is caused by a microbial agent (e.g., common cold). Infectious diseases are known in the art and include, for example, hepatitis, sexually transmitted diseases (e.g., *Chlamydia*, gonorrhea), tuberculosis, HIV/AIDS, diphtheria, hepatitis B, hepatitis C, cholera, and influenza.

For purposes herein, "autoimmune disease" refers to a disease in which the body produces an immunogenic (i.e., immune system) response to some constituent of its own tissue. In other words the immune system loses its ability to recognize some tissue or system within the body as "self" and targets and attacks it as if it were foreign. Autoimmune diseases can be classified into those in which predominantly one organ is affected (e.g., hemolytic anemia and anti-immune thyroiditis), and those in which the autoimmune disease process is diffused through many tissues (e.g., systemic lupus erythematosus). For example, multiple sclerosis is thought to be caused by T cells attacking the sheaths that surround the nerve fibers of the brain and spinal cord. This results in loss of coordination, weakness, and blurred vision. Autoimmune diseases are known in the art and include, for instance, Hashimoto's thyroiditis, Grave's disease, lupus, multiple sclerosis, rheumatic arthritis, hemolytic anemia, anti-immune thyroiditis, systemic lupus erythematosus, celiac disease, Crohn's disease, colitis, diabetes, scleroderma, psoriasis, and the like.

With respect to the inventive methods, the cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor. Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer. Preferably, the cancer is melanoma.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

Also provided is a method of detecting a diseased cell in a host, wherein the diseased cell expresses an antigen characteristic of a disease. The method comprises (i) contacting a sample comprising cells of the host with any of the inventive modified TCRs, polypeptides, proteins, nucleic acids, recombinant expression vectors, host cells, and populations of host cells described herein, thereby forming a complex between the antigen which is characteristic of the disease and the inventive modified TCR, polypeptide, protein, nucleic acid, recombinant expression vector, host cell, or population of cells, and (ii) detecting the complex, wherein detection of the complex is indicative of a diseased cell in the host.

The diseased cell can be any cell of any disease, which cell expresses an antigen that is characteristic of the disease. The diseased cell can be a cancer cell or an infected cell, for example. Preferably, the diseased cell is a melanoma cell In the method of treating or preventing a disease or of detecting a diseased cell, the inventive modified TCR has antigenic specificity for an antigen that is characteristic of the disease to be treated, prevented, or detected. For instance, if the disease to be treated, prevented or detected is melanoma, the inventive modified TCR has antigenic specificity for a melanoma antigen, e.g., MART-1, NY-ESO-1, gp100, etc. If a host cell or a population comprising at least one host cell is used in the method, the host cell desirably expresses a TCR having antigenic specificity for the antigen of the disease. If an inventive nucleic acid or recombinant expression vector is used in the method, the nucleic acid or recombinant expression vector desirably encodes the modified TCR which has antigenic specificity for an antigen of the disease to be treated, prevented, or detected, such that expression of the nucleic acid or recombinant expression vector is achieved in a cell and the TCR expressed by the cell is capable of binding to the antigen of the disease.

With respect to the inventive method of detecting a diseased cell in a host, the sample comprising cells of the host can be a sample comprising whole cells, lysates thereof, or a fraction of the whole cell lysates, e.g., a nuclear or cytoplasmic fraction, a whole protein fraction, or a nucleic acid fraction. If the sample comprises whole cells, the cells can be any cells of the host, e.g., the cells of any organ or tissue, including blood cells.

For purposes of the inventive detecting method, the contacting step can take place in vitro or in vivo with respect to the host. Preferably, the contacting is an in vitro step.

Also, detection of the complex can occur through any number of ways known in the art. For instance, the inventive modified TCRs, polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

For purposes of the inventive methods, wherein host cells or populations of cells are administered to the host, the cells can be cells that are allogeneic or autologous to the host. Preferably, the cells are autologous to the host.

The host referred to herein can be any host. Preferably, the host is a mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

A method of identifying a candidate adoptive immunotherapy TCR is also provided. The method consists of (a) producing a nucleic acid encoding a modified TCR comprising a WT TCR amino acid sequence with no more than three amino acid substitutions, (b) expressing the nucleic acid in CD4+ T cells and CD8+ T cells, and (c) assaying the T cells for the ability to recognize target cells and for antigen specificity. A candidate adoptive immunotherapy TCR is identified when the modified TCR, as compared to the WT TCR, (i) has an enhanced ability to recognize target cells when expressed in CD4+ T cells and (ii) does not exhibit a decrease in antigen specificity when expressed by CD8+ T cells.

The term "candidate adoptive immunotherapy TCR" as used herein refers to a modified TCR which comprises an amino acid sequence of a WT TCR with no more than three amino acid substitutions and, as compared to the WT TCR (i) has an enhanced ability recognize target cells when expressed in CD4+ T cells and (ii) does not exhibit a decrease in antigen specificity when expressed by CD8+ T cells. Such candidate cells are predicted to work well in the context of adoptive immunotherapy, such that the TCR, when expressed in T cells of a patient, will be able to treat or prevent a disease of the patient.

Producing a nucleic acid encoding a modified TCR can be carried out by any means known in the art. For instance, Examples 2 to 4 describe methods of making such a nucleic acid in which a WT TCR sequence is used as a template for a PCR reaction which utilizes primers which encode the amino acid substitutions. The resulting PCR product, which encodes the amino acid mutations is then in vitro transcribed, thereby producing an RNA encoding the modified TCR. Alternatively, the nucleic acid can be produced by other means, e.g., site directed mutagenesis.

With respect to the method of identifying a candidate adoptive immunotherapy TCR, the amino acid substitutions preferably are conservative amino acid substitutions. More preferably, the amino acid substitutions are located within a CDR of the TCR, e.g., CDR1, CDR2, CDR3. Most preferably, the amino acid substitutions are located within the CDR2 of a β chain of the TCR. Also, with regard to this method, the modified TCR has at least twice the ability to recognize target cells as the WT TCR and exhibits this enhanced ability in at least two assays.

Methods of expressing nucleic acids in cells (including CD4+ T cells and CD8+ T cells) are known in the art, as discussed herein. Preferably, the nucleic acid is an RNA and the RNA is expressed in T cells by methods described in Example 2.

The T cells can be assayed for the ability to recognize target cells and for antigen specificity employing methods known in the art. Preferably, the T cells are assayed as described herein as Example 2.

EXAMPLES

The following examples further illustrate the invention but, of course, should not be construed as in any way limiting its scope.

The following examples describe the amino acid substitutions of the modified TCRs with respect to the immature TCR sequence (i.e., the TCR sequence with the leader sequence).

Example 1

This example demonstrates a method of making a modified TCR of the invention.

The WT 1G4 alpha and beta chains were isolated using RT-PCR. The RT reaction was carried out as described in Huang et al., *J. Immunol.,* 172: 6057-6064 (2004), and the fragments were amplified using a high fidelity DNA polymerase, Fusion (New England Biolabs) according to the manufacturer's instructions. Specifically, the WT 1G4 β chain was isolated by RT-PCR from an in vitro cultured tumor infiltrating lymphocytes (TIL) sample isolated from a melanoma patient using two primer pairs: the first pair (Primers A and B) was used to isolate the variable region sequence but also contained sequences corresponding to the appropriate J region, while the second primer pair (Primers C and D) was used to isolate the full length constant region but also encoded the J region to allow an overlap with the sequence amplified using the first primer pair. The full length construct encoding the β chain was generated by isolation of the two PCR products on an agarose gel, which products were then mixed and used to carry out a second round of amplification using Primers E and F.

The 1G4 TR α chain was constructed by RT-PCR from an in vitro cultured TIL sample of using two primer pairs: the first pair (Primers G and H) was used to isolate the 1G4 α chain variable region sequence including part of the J region, while the second pair (Primers I and J) was used to isolate the 1G4 α chain constant region but also encoded the J region. The full length construct encoding the α chain was generated by isolation of the two PCR products on an agarose gel, which were then mixed and used to carry out a second round of amplification using Primers K and L. The sequences of the primers used to obtain the WT 1G4 nucleic acid are set forth in Table 1.

TABLE 1

| Name | Primer | Sequence | SEQ ID NO |
|---|---|---|---|
| β chain 5' fragment | A | GACTAATTAACCCTCACTAAAGGGACACCATGAGCATCGGCCTCCTGTG | 40 |
| | B | CTCCCCGGTGTTCCCGACGTAACTGCTGGCACAGAAGTAC | 41 |
| β chain 3' fragment | C | CAGCAGTTACGTCGGGAACACCGGGGAGCTGTTTTTTGGAGAAG | 42 |
| | D | TTTTTTTTTTTTTTTTTTTTTTTTTTTTTTTTTTTTTTTTTTTTTTTTTTTTTTTTTTTTTTTT TCAGCCTCTGGAATCCTTTCTCTTGA | 43 |
| β chain full length Primers | E | GACTAATTAACCCTCACTAAAGGGACACCATGAGCATCGGCCTCCTGTG | 44 |
| | F | TTTTTTTTTTTTTTTTTTTTTTTTTTTTTTTTTTTTTTTTTTTTTTTTTTTTTTTTTTTTTTTT TCAGCCTCTGGAATCCTTTCTCT | 45 |
| α chain 5' fragment | G | CTGGTTCCTCTTCCAAATGTAGGTATGTAGCTTCCTCCTGATGTGGGCCTCACAGCAC AGAGGTAGG | 46 |
| | H | GACTAATTAACCCTCACTAAAGGGACACCATGGAGACCCTCTTGGGC | 47 |
| α chain 3' fragment | I | CTACATACCTACATTTGGAAGAGGAACCAGCCTTATTGTTCATCCGTATATCCAGAA CCCTGACCC | 48 |
| | J | TTTTTTTTTTTTTTTTTTTTTTTTTTTTTTTTTTTTTTTTTTTTTTTTTTTTTTTTTTTTTTTT TCAGCTGGACCACAGCCGCAGCGTC | 49 |
| α chain full length Primers | K | GACTAATTAACCCTCACTAAAGGGACACCATGGAGACCCTCTTGGGC | 50 |
| | L | TTTTTTTTTTTTTTTTTTTTTTTTTTTTTTTTTTTTTTTTTTTTTTTTTTTTTTTTTTTTTTTT TCAGCTGGACCACAGCCGCAGCG | 51 |

The nucleotide sequence of the 1G4 TCR obtained is set forth as SEQ ID NO: 25 (alpha chain) and SEQ ID NO: 21 (beta chain). For generation of each mutant 1G4 TCR, a 5' fragment and a 3' fragment, which encoded the amino acid substitution, were produced by PCR amplification of SEQ ID NO: 21. Primers M and N were used to produce the 5' fragment for each mutant. Primers O and P were used to produce the 3' fragment of 1G4 mut1, Primers Q and R were used to produce the 3' fragment of 1G4 mut2, and Primers S and T were used to produce the 3' fragment of 1G4 mut3. The 1G4 PCR products were isolated on agarose gels and the final PCR product generated by amplification of the 5' fragment with the 3' fragments using the full length primer pair (Primers U and V). The sequences of the primers used to generate the mutant beta chains of are set forth in Table 2.

The resulting PCR products were in vitro transcribed into RNA as described in Zhao et al., *Mol. Ther.* 13: 151-159 (2006).

This example demonstrates that the modified TCRs of the invention can be made.

Example 2

This example demonstrates the biological activity of the modified TCRs of the invention as compared to their wild-type counterparts.

The modified TCRs produced in Example 1 were tested for their ability recognize antigen when separately expressed in CD8$^+$ T cells and CD4$^+$ T cells. PBMC from Patient KS were transfected as described in Zhao et al. (2006), supra with (i)

TABLE 2

| Name | | Primer | Sequence | SEQ ID NO: |
|---|---|---|---|---|
| 1G4 β | 5' fragment | M | GACTAATTAACCCTCACTAAAGGGACACCATGAGCATCGGCCTCCTGTG | 52 |
| | | N | TGAGTAATGAATCAGCCTCAGC | 53 |
| 1G4 mut1 (G70A) | 3' | O | GCTGAGGCTGATTCATTACTCAGTTGCCGCTGGTATCACTGACCAAGGAGAAGTC | 54 |
| | fragment | P | TTTTTTTTTTTTTTTTTTTTTTTTTTTTTTTTTTTTTTTTTTTTTTTTTTTTT TTTTTTTTTTTTCAGCCTCTGGAATCCTTTCTCT | 55 |
| 1G4 mut2 (A71I) | 3' fragment | Q | GCTGAGGCTGATTCATTACTCAGTTGGTATCGGTATCACTGACCAAGGAGAAGTC | 56 |
| | | R | TTTTTTTTTTTTTTTTTTTTTTTTTTTTTTTTTTTTTTTTTTTTTTTTTTTTTTTTTTTTTTTT CAGCCTCTGGAATCCTTTCTCT | 57 |
| 1G4 mut3 (G70A/A71I) | 3' fragment | S | GCTGAGGCTGATTCATTACTCAGTTGCCATCGGTATCACTGACCAAGGAGAAGTC | 58 |
| | | T | TTTTTTTTTTTTTTTTTTTTTTTTTTTTTTTTTTTTTTTTTTTTTTTTTTTTTTTTTTTTTTTT CAGCCTCTGGAATCCTTTCTCT | 59 |
| Full length Primer Pair | | U | GACTAATTAACCCTCACTAAAGGGACACCATGAGCATCGGCCTCCTGTG | 60 |
| | | V | TTTTTTTTTTTTTTTTTTTTTTTTTTTTTTTTTTTTTTTTTTTTTTTTTTTTTTTTTTTTTTT CAGCCTCTGGAATCCTTTCTCT | 61 |

***mutated nucleotides noted by shading

RNA encoding the WT alpha chain of the 1G4 NY-ESO-1-specific TCR and (ii) RNA encoding the WT beta chain of the 1G4 TCR, RNA encoding one of the following mutant beta chains of 1G4: 1G4 mut1 (G70A; SEQ ID NO: 1), 1G4 mut2 (A71I, SEQ ID NO: 2), or 1G4 mut3 (G70A/A71I, SEQ ID NO: 3), or DNA encoding Green Fluorescence Protein (GFP).

Transfected cells were washed and stimulated with or without (T alone) one of the following cells: T2+ pulsed with either 1 μM NY-ESO-1 peptide SLLMWITQC (ESO; SEQ ID NO: 92) or g9-154 peptide KTWGQYWQV (g9-154; SEQ ID NO: 93) or melanoma cells: A375 (HLA-A2$^+$/NY-ESO-1$^+$), 624.38 (HLA-A2$^+$/NY-ESO-1$^+$), 1363 (HLA-A2$^+$/NY-ESO-1$^+$), 526 (HLA-A2$^+$/NY-ESO-1$^-$), and SK (HLA-A2$^+$/NY-ESO-1$^-$).

Responder cells ($1\times10^5$ electroporated PBLs) and $1\times10^5$ stimulator cells (pulsed T2 cells or melanoma cells) were incubated in a 0.2-ml culture volume in individual wells of 96-well plates. Stimulator cells and responder cells were co-cultured for 16 to 24 h. Cytokine secretion of culture supernatants diluted to the linear range of the assay was measured using commercially available ELISA kits (IFN-γ Endogen, Cambridge, Mass.).

The amount of IFN-γ (pg/ml) produced by transfected CD8$^+$ T cells are shown in Table 3, while the amount of IFN-γ (pg/ml) produced by transfected CD4$^+$ T cells are shown in Table 4.

TABLE 3

| α chain<br>β chain | WT<br>WT | WT<br>G70A | WT<br>G70A/A71I | WT<br>A71I | GFP |
|---|---|---|---|---|---|
| g9-154 | <30 | <30 | <30 | <30 | <30 |
| ESO | 11250 | 10150 | 8860 | 10080 | <30 |
| A375 | 145 | 579 | 766 | 1058 | <30 |
| 624.38 | 3030 | 6270 | 5280 | 7530 | <30 |
| 1363 | 175 | 517 | 535 | 911 | 46 |
| 526 | <30 | <30 | <30 | <30 | <30 |
| SK | <30 | <30 | 38 | <30 | <30 |
| T alone | <30 | <30 | <30 | <30 | <30 |

TABLE 4

| α chain<br>β chain | WT<br>WT | WT<br>G70A | WT<br>G70A/A71I | WT<br>A71I | GFP |
|---|---|---|---|---|---|
| g9-154 | <30 | <30 | <30 | <30 | <30 |
| ESO | 3540 | 6380 | 10690 | 8970 | <30 |
| A375 | 30 | 58 | 872 | 157 | 40 |
| 624.38 | <30 | 88 | 1374 | 418 | <30 |
| 1363 | 49 | 75 | 611 | 269 | 50 |
| 526 | <30 | <30 | <30 | <30 | <30 |
| SK | <30 | <30 | <30 | <30 | <30 |
| T alone | <30 | <30 | <30 | <30 | <30 |

This example demonstrated that the modified TCRs of the invention have enhanced antigen specificity when expressed in CD4$^+$ T cells and CD8$^+$ T cells.

Example 3

This example demonstrates a method of making modified TCRs specific for the MART-1 cancer antigen.

The DMF5 (F5) TCR which is specific for the cancer antigen MART-1 was isolated and the nucleotide sequence of the F5 TCR obtained is set forth as SEQ ID NO: 30 (alpha chain) and SEQ ID NO: 31 (beta chain).

The F5 α chain was amplified from the cloned gene product (SEQ ID NO: 30) to generate RNA using Primers W and X. The F5 beta chain was amplified from the cloned gene product (SEQ ID NO: 31) to generate RNA using Primers Y and Z.

For generation of each mutant F5 TCR, a 5' fragment and a 3' fragment, which encoded the amino acid substitution, were produced by PCR amplification of SEQ ID NO: 31. Primers AA and AB were used to produce the 5' fragment for each mutant. Primers AC and AD were used to produce the 3' fragment of F5 mut1, Primers AE and AF were used to produce the 3' fragment of F5mut2, Primers AG and AH were used to produce the 3' fragment of F5mut3, Primers AI and AJ were used to produce the 3' fragment of F5mut 4, and Primers AK and AL were used to produce the 3' fragment of F5mut5. The PCR products were isolated on agarose gels and the final PCR product generated by amplification of the 5' fragment with the 3' fragments using the full length primer pair (Primers AM and AN). The sequences of the primers used to generate the mutant beta chains of are set forth in Table 5.

TABLE 5

| | Primer | Sequence | SEQ ID NO: |
|---|---|---|---|
| α chain RNA | W | GACTAATTAACCCTCACTAAAGGGACACCATGATGAAATCCTTGAGAGTTTTACTAG | 62 |
| | X | TTTTTTTTTTTTTTTTTTTTTTTTTTTTTTTTTTTTTTTTTTTTTTTTTTTTTTTTTTTTTTTTT<br>CAGCTGGACCACAGCCGCAGCGTC | 63 |
| β chain RNA | Y | TCAGAATTAACCCTCACTAAAGGGACTAGTCCTGCAGGTTTAAACGAATTCGCCCTTCACCAT<br>GAGAATCAGGCTCCTGTGCT | 64 |
| | Z | TTTTTTTTTTTTTTTTTTTTTTTTTTTTTTTTTTTTTTTTTTTTTTTTTTTTTTTTTTTTTTTTT<br>TCAGAAATCCTTTCTCTTGACCAT | 65 |
| β chain 5' fragment | AA | TCAGAATTAACCCTCACTAAAGGGACTAGTCCTGCAGGTTTAAACGAATTCGCCCTTCACCAT<br>GAGAATCAGGCTCCTGTGCT | 66 |
| | AB | TGAATAATGGATGAGCCTTAGC | 67 |
| F5 mut 1 T73A) | AC | GCTAAGGCTCATCCATTATTCAAATACTGCAGGTGCCACTGGCAAAGGAGAAGTCC | 68 |
| | AD | TTTTTTTTTTTTTTTTTTTTTTTTTTTTTTTTTTTTTTTTTTTTTTTTTTTTTTTTTTTTTTTTT<br>TCAGAAATCCTTTCTCTTGACCAT | 69 |
| F5 mut 2 T70V/T73A) | AE | GCTAAGGCTCATCCATTATTCAAATGTGGCAGGTGCCACTGGCAAAGGAGAAGTCC | 70 |
| | AF | TTTTTTTTTTTTTTTTTTTTTTTTTTTTTTTTTTTTTTTTTTTTTTTTTTTTTTTTTTTTTTTT<br>TCAGAAATCCTTTCTCTTGACCAT | 71 |

TABLE 5-continued

| | Primer | Sequence | SEQ ID NO: |
|---|---|---|---|
| F5 mut 3 (T70V/A71M) | AG | GCTAAGGCTCATCCATTATTCAAATGTGATGGGTACCACTGGCAAAGGAGAAGTCC | 72 |
| | AH | TTTTTTTTTTTTTTTTTTTTTTTTTTTTTTTTTTTTTTTTTTTTTTTTTTTTTTTTTTTTTTTT TCAGAAATCCTTTCTCTTGACCAT | 73 |
| F5 mut 4 (A71M/T73A) | AI | GCTAAGGCTCATCCATTATTCAAATACTATGGGTGCCACTGGCAAAGGAGAAGTCC | 74 |
| | AJ | TTTTTTTTTTTTTTTTTTTTTTTTTTTTTTTTTTTTTTTTTTTTTTTTTTTTTTTTTTTTTTTT TCAGAAATCCTTTCTCTTGACCAT | 75 |
| F5 mut 5 (T70V/A71M/73A) | AK | GCTAAGGCTCATCCATTATTCAAATGTGATGGGTGCCACTGGCAAAGGAGAAGTCC | 76 |
| | AL | TTTTTTTTTTTTTTTTTTTTTTTTTTTTTTTTTTTTTTTTTTTTTTTTTTTTTTTTTTTTTTTT TCAGAAATCCTTTCTCTTGACCAT | 77 |
| Full length | AM | GACTAATTAACCCTCACTAAAGGGACACCATGGGCACAAGGTTGTTCTTC | 78 |
| Primer Pair | AN | TTTTTTTTTTTTTTTTTTTTTTTTTTTTTTTTTTTTTTTTTTTTTTTTTTTTTTTTTTTTTTTT TCAGAAATCCTTTCTCTTGACCAT | 79 |

***mutated nucleotides are shaded

PBMC from Patients RS, KS, and HS were transfected and assayed as described in Example 2, except that RNA encoding either the WT or mutant F5 beta chains along with the WT alpha chains were used in transfections. Also, T2+ cells were pulsed with either 1 μg g9-154 peptide or MART-1 peptide AAGIGILTV (MART; SEQ ID NO: 94). Also, the following melanoma cells were used: 526 ($A2^+$/MART-$1^+$), 624 ($A2^+$/MART-$1^+$), 1359 ($A2^+$/MART-$1^+$), 1363 ($A2^+$/MART-$1^-$), A375 ($A2^+$/MART-$1^-$), 888, 888A2, 397A2 ($A2^+$/MART-$1^+$), 624.38 ($A2^+$/MART-$1^+$), 1300 ($A2^+$/MART-$1^+$), 397A24 ($A2^+$/MART-$1^-$), 624.28 ($A2^+$/MART-$1^+$), 526 ($A2^+$/NY-ESO-$1^-$), SK23 ($A2^+$/MART-$1^+$), and SK ($A2^+$/NY-ESO-$1^-$).

The amounts of IFN-γ (pg/ml) produced by transfected $CD8^+$ T cells of Patient RS are shown in Table 6, while the amounts of IFN-γ (pg/ml) produced by transfected $CD4^+$ T cells of Patient RS are shown in Table 7. The amounts of IFN-γ (pg/ml) produced by transfected $CD8^+$ T cells of Patient KS are shown in Table 8, while the amounts of IFN-γ (pg/ml) produced by transfected $CD4^+$ T cells of Patient KS are shown in Table 9. The amounts of IFN-γ (pg/ml) produced by transfected $CD8^+$ T cells of Patient HS are shown in Table 10, while the amounts of IFN-γ (pg/ml) produced by transfected $CD4^+$ T cells of Patient HS are shown in Table 11. The amounts of IFN-γ (pg/ml) produced by transfected $CD8^+$ T cells of Patient KG and MB expressing the modified TCR containing the triple mutant are shown in Tables 12 and 14, while the amounts of IFN-γ (pg/ml) produced by transfected $CD4^+$ T cells of Patient KG and MB expressing the triple mutant are shown in Tables 13 and 15.

TABLE 6

| | α chain | | | | | | | | |
|---|---|---|---|---|---|---|---|---|---|
| | WT | WT | WT | WT | WT | WT | WT | WT | |
| | β chain | | | | | | | | |
| | WT | T70A | T70I | A71I | A71V | T73A | T73I | G72A | GFP |
| g9-154 | <31 | <31 | <31 | <31 | <31 | 222 | <31 | <31 | <31 |
| MART | 17920 | 12770 | 12150 | 14800 | 12880 | 16010 | 6710 | 128 | 136 |
| 526 | 2030 | 960 | 1210 | 1710 | 1050 | 1690 | 120 | 124 | 110 |
| 624 | 7130 | 5130 | 4160 | 7120 | 4580 | 7360 | 710 | 163 | 128 |
| 1359A2 | 1610 | 700 | 940 | 1200 | 680 | 1180 | 280 | 174 | 196 |
| 1363 | 1430 | 440 | 420 | 1310 | 820 | 1260 | 155 | 79 | 167 |
| A375 | 179 | 259 | 43 | 203 | 211 | 250 | 241 | 279 | 250 |
| T alone | <31 | <31 | <31 | <31 | <31 | <31 | <31 | <31 | <31 |

TABLE 7

| | α chain | | | | | | | | |
|---|---|---|---|---|---|---|---|---|---|
| | WT | WT | WT | WT | WT | WT | WT | WT | |
| | β chain | | | | | | | | |
| | WT | T70A | T70I | A71I | A71V | T73A | T73I | G72A | GFP |
| g9-154 | 119 | 114 | 114 | 79 | 44 | 39 | 36 | 42 | 41 |
| MART-1 | 129 | 8440 | 30770 | 34280 | 30770 | 38190 | 273 | 14450 | 114 |
| 526 | 82 | 148 | 1630 | 1210 | 550 | 4650 | 83 | 205 | 111 |
| 624 | 98 | 260 | 8400 | 5130 | 2500 | 24250 | 74 | 732 | 106 |
| 1359A2 | 109 | 12360 | 305 | 219 | 302 | 1800 | 87 | 131 | 109 |

TABLE 7-continued

| | α chain | | | | | | | | |
|---|---|---|---|---|---|---|---|---|---|
| | WT | WT | WT | WT | WT | WT | WT | WT | |
| | β chain | | | | | | | | |
| | WT | T70A | T70I | A71I | A71V | T73A | T73I | G72A | GFP |
| 1363 | 132 | 160 | 248 | 438 | 352 | 2320 | 151 | 145 | 188 |
| A375 | 291 | 359 | 266 | 306 | 254 | 306 | 290 | 295 | 304 |
| T alone | <31 | <31 | <31 | <31 | <31 | <31 | <31 | <31 | <31 |

TABLE 8

| | α chain | | | | | | | | |
|---|---|---|---|---|---|---|---|---|---|
| | WT | WT | WT | WT | WT | WT | WT | WT | |
| | β chain | | | | | | | | |
| | WT | T70A | T70I | A71I | A71V | T73A | T73I | G72A | GFP |
| g9-154 | <30 | <30 | <30 | <30 | 31 | <30 | <30 | <30 | <30 |
| MART-1 | 17110 | 15530 | <30 | 16450 | 15880 | 17860 | 4190 | 15060 | <30 |
| 526 | 1265 | 726 | <30 | 1016 | 1292 | 1089 | 19 | 672 | <30 |
| 624 | 6110 | 3030 | <30 | 3770 | 4770 | 4110 | 192 | 1754 | <30 |
| 1359A2 | 1531 | 92 | 1113 | 1226 | 1315 | 82 | 727 | 125 | 109 |
| 1363 | 746 | 99 | 648 | 644 | 514 | 72 | 149 | 87 | 188 |
| A375 | 50 | 37 | 64 | <30 | 46 | 48 | 31 | 48 | 50 |
| 1359 | <30 | 685 | <30 | <30 | <30 | <30 | <30 | <30 | <30 |
| T alone | <30 | <30 | <30 | <30 | <30 | <30 | <30 | <30 | <30 |

TABLE 9

| | α chain | | | | | | | | |
|---|---|---|---|---|---|---|---|---|---|
| | WT | WT | WT | WT | WT | WT | WT | WT | |
| | β chain | | | | | | | | |
| | WT | T70A | T70I | A71I | A71V | T73A | T73I | G72A | GFP |
| g9-154 | <30 | <30 | <30 | <30 | <30 | <30 | <30 | <30 | <30 |
| MART-1 | 5390 | 316 | 7190 | 524 | 7120 | 12600 | <30 | 1580 | <30 |
| 526 | 30 | <30 | 63 | <30 | 50 | 207 | <30 | <30 | <30 |
| 624 | 99 | <30 | 256 | 13 | 148 | 767 | <30 | <30 | <30 |
| 1359A2 | 94 | 981 | 94 | 91 | 85 | 240 | 51 | 59 | 29 |
| 1363 | 97 | 114 | 74 | 104 | 72 | 97 | 75 | 46 | 57 |
| A375 | 67 | 52 | 71 | 59 | 54 | 67 | 45 | 38 | 52 |
| 1359 | 80 | 3810 | 94 | 150 | 66 | 90 | 120 | 61 | 59 |
| T alone | <30 | <30 | <30 | <30 | <30 | <30 | <30 | <30 | <30 |

TABLE 10

| | α chain | | | | | | | | |
|---|---|---|---|---|---|---|---|---|---|
| | WT | WT | WT | WT | WT | WT | WT | WT | |
| | β chain | | | | | | | | |
| | WT | T70A | T70I | A71I | A71V | T73A | T73I | G72A | GFP |
| G9-154 | 50 | 64 | 61 | 54 | 67 | 38 | 36 | 23 | 24 |
| MART-1 | 20210 | 19280 | 18730 | 4630 | 20910 | 19890 | 6120 | 14970 | 24 |
| 526 | 1984 | 1114 | 1342 | 44 | 1598 | 1352 | 38 | 606 | <30 |
| 624 | 7030 | 4520 | 7040 | 210 | 6432 | 7340 | 283 | 3500 | 9 |
| 1359A2 | 2140 | 1340 | 1500 | 118 | 1940 | 2320 | 83 | 551 | 37 |
| 1363 | 791 | 292 | 237 | 78 | 565 | 761 | 53 | 214 | 46 |
| A375 | 57 | 83 | 64 | 105 | 87 | 95 | 65 | 30 | 61 |
| 1359 | 27 | 1917 | 57 | 66 | 50 | 27 | 66 | 44 | 34 |
| T alone | <30 | <30 | <30 | <30 | <30 | <30 | <30 | <30 | <30 |

TABLE 11

| | α chain | | | | | | | | |
|---|---|---|---|---|---|---|---|---|---|
| | WT | WT | WT | WT | WT | WT | WT | WT | |
| | β chain | | | | | | | | |
| | WT | T70A | T70I | A71I | A71V | T73A | T73I | G72A | GFP |
| g9-154 | <30 | <30 | <30 | <30 | <30 | <30 | 36 | <30 | <30 |
| MART-1 | 22000 | 4553 | 21700 | 7470 | 36440 | 25820 | 242 | <30 | <30 |
| 526 | 294 | <30 | 1045 | <30 | 711 | 2379 | <30 | <30 | <30 |
| 624 | 1626 | 104 | 3849 | 115 | 2908 | 9236 | <30 | <30 | <30 |
| 1359A2 | 471 | 9240 | 826 | 93 | 646 | 2192 | 57 | 65 | 56 |
| 1363 | 453 | 486 | 474 | 435 | 545 | 886 | 484 | 334 | 550 |
| A375 | 279 | 316 | 335 | 212 | 262 | 246 | 369 | 217 | 228 |
| 1359 | 179 | 2328 | 207 | 213 | 196 | 237 | 204 | 205 | 267 |
| T alone | <30 | <30 | <30 | <30 | <30 | <30 | <30 | <30 | <30 |

TABLE 12

| | α chain | | | | | | | |
|---|---|---|---|---|---|---|---|---|
| | WT | WT | WT | WT | WT | WT | WT | WT |
| | β chain | | | | | | | |
| | WT | T73A | T73G | T73S | T70V/A71M | T70V/T73A | A71M/T73A | T70V/A71M/T73A |
| MART (1 μM) | 25100 | 29280 | 21600 | 24240 | 26240 | 20900 | 26000 | 18440 |
| ESO (10 nM) | <30 | <30 | <30 | <30 | <30 | <30 | <30 | <30 |
| 888 | <30 | <30 | <30 | <30 | <30 | <30 | <30 | <30 |
| 888A2 | 7600 | 10340 | 8380 | 10080 | 7360 | 5260 | 6960 | 4860 |
| 397 A2 | 3600 | 4440 | 4200 | 4040 | 3330 | 1780 | 3460 | 2500 |
| 624.38 | 6840 | 8140 | 6800 | 7460 | 5520 | 4080 | 6940 | 5360 |
| 1300 | 6400 | 7360 | 6880 | 5940 | 5840 | 4140 | 5060 | 5880 |
| T Alone | <30 | <30 | <30 | <30 | <30 | <30 | <30 | <30 |

TABLE 13

| | α chain | | | | | | | |
|---|---|---|---|---|---|---|---|---|
| | WT | WT | WT | WT | WT | WT | WT | WT |
| | β chain | | | | | | | |
| | WT | T73A | T73G | T73S | T70V/A71M | T70V/T73A | A71M/T73A | T70V/A71M/T73A |
| MART (1 μM) | 6980 | 18060 | 7020 | 17830 | >20000 | 25180 | 40660 | >20000 |
| ESO (10 nM) | <30 | <30 | <30 | <30 | <30 | <30 | <30 | <30 |
| 888 | <30 | <30 | <30 | <30 | <30 | <30 | <30 | <30 |
| 888A2 | 2420 | 4600 | 3780 | 4200 | 5620 | 5170 | 5640 | 6540 |
| 397 A2 | 330 | 1600 | 537 | 1250 | 2240 | 2100 | 2310 | 3470 |
| 624.38 | 482 | 2410 | 1140 | 1460 | 2690 | 2300 | 3190 | 4250 |
| 1300 | 851 | 2020 | 1870 | 640 | 3200 | 2560 | 3090 | 3420 |
| T alone | <30 | <30 | <30 | <30 | <30 | <30 | <30 | <30 |

TABLE 14

| | α chain | | | | | | | | | |
|---|---|---|---|---|---|---|---|---|---|---|
| | WT | WT | WT | WT | WT | WT | WT | WT | WT | |
| | β chain | | | | | | | | | |
| | WT | T70A/A71M | T70V/A71M/T73A | A71M/T73A | T73A | T73G | T73I | T73L | T73S | GFP |
| gp100 | 260 | 250 | 494 | 144 | 139 | 125 | 36 | 40 | 157 | <30 |
| MART (1 uM) | 52900 | 41250 | 38500 | 28400 | 36250 | 30050 | 11500 | 2300 | 16350 | <30 |
| A375 | 43 | 37 | 38 | 33 | <30 | 31 | <30 | <30 | <30 | <30 |
| 397 A24 | <30 | <30 | <30 | <30 | <30 | <30 | <30 | <30 | <30 | <30 |

TABLE 14-continued

| | α chain | | | | | | | | | |
|---|---|---|---|---|---|---|---|---|---|---|
| | WT | WT | WT | WT | WT | WT | WT | WT | WT | |
| | β chain | | | | | | | | | |
| | WT | T70A/A71M | T70V/A71M/T73A | A71M/T73A | T73A | T73G | T73I | T73L | T73S | GFP |
| 624.28 | <30 | <30 | <30 | <30 | <30 | <30 | <30 | <30 | <30 | <30 |
| 397 A2 | 45000 | 31550 | 27650 | 26850 | 30750 | 30150 | 5650 | 146 | 45100 | <30 |
| 526 | 16700 | 15800 | 10750 | 12550 | 12300 | 13500 | 321 | 32 | 16200 | <30 |
| 624.38 | 48900 | 47650 | 32500 | 29850 | 28100 | 35150 | 8000 | 179 | 49100 | <30 |
| 1300 | 96600 | 43100 | 39100 | 48150 | 37250 | 49000 | 16450 | 2550 | 53050 | 32 |
| SK 23 | 22250 | 29450 | 22800 | 24850 | 18600 | 18950 | 4500 | 144 | 29800 | <30 |
| T Alone | <30 | <30 | <30 | <30 | <30 | <30 | <30 | <30 | <30 | <30 |

TABLE 15

| | α chain | | | | | | | | | |
|---|---|---|---|---|---|---|---|---|---|---|
| | WT | WT | WT | WT | WT | WT | WT | WT | WT | |
| | β chain | | | | | | | | | |
| | WT | T70A/A71M | T70V/A71M/T73A | A71M/T73A | T73A | T73G | T73I | T73L | T73S | GFP |
| gp100 | 131 | <30 | <30 | <30 | <30 | <30 | <30 | <30 | <30 | <30 |
| MART (1 uM) | 32300 | 54000 | 33800 | 34500 | 25000 | 25300 | 1300/ 2350 | >2000/ <50,000 | 12100/ 39800 | <30 |
| A375 | 40 | 69 | 37 | 50 | 59 | 60 | 128 | 54 | 37 | 36 |
| 397 A24 | <30 | <30 | <30 | <30 | <30 | <30 | <30 | <30 | <30 | <30 |
| 624.28 | <30 | <30 | <30 | <30 | <30 | <30 | <30 | <30 | <30 | <30 |
| 397 A2 | 39900 | 58800 | 145300 | 46100 | 31400 | 32800 | 190 | 51 | 33000 | <30 |
| 526 | 4100 | 24000 | 26600 | 19000 | 14700 | 16900 | <30 | <30 | 13200 | <30 |
| 624.38 | 60400 | 102200 | 93800 | 46500 | 49800 | 32600 | 198 | <30 | 44500 | <30 |
| 1300 | 53100 | 96400 | >200,000 | 73600 | 53000 | 34600 | 555 | 79 | 51000 | <30 |
| SK | 30000 | 86100 | 82000 | 43700 | 34700 | 32700 | 209 | <30 | 44800 | <30 |
| T Alone | <30 | <30 | <30 | <30 | <30 | <30 | <30 | <30 | <30 | <30 |

This example demonstrated that the modified F5 receptors F5 mut1 (T52A) and F5 mut5 (T49V/A50M/T52A) have enhanced capability to recognize target cells in $CD4^+$ T cells without having a decreased antigen specificity in $CD8^+$ T cells.

Example 4

This example demonstrates a method of making another set of modified TCRs specific for the MART-1 cancer antigen.

The DMF4 (F4) TCR which is specific for the cancer antigen MART-1 was isolated as described in Hughes et al., *Hum. Gene Ther.* 16: 457-472 (2005). The nucleotide sequence of the F4 TCR obtained is set forth as SEQ ID NO: 26 (alpha chain) and SEQ ID NO: 27 (beta chain).

The DMF4 β chain was amplified using Primers AO and AP to generate RNA. For the generation of each mutant F4 TCR, a 5' fragment and a 3' fragment, which encoded the amino acid substitution, were produce by PCR amplification of SEQ ID NO: 27. Primers AQ and AR were used to generate the 5' fragment for each mutant. Primers AS and AT were used to produce the 3' fragment of F4 mut1 and Primers AU and AV were used to produce the 3' fragment of F4 mut2. The 5' and 3' fragments were then gel purified, mixed, and amplified using the Primers AW and AX to generate the full length construct. The α chain of the F4 TCR was amplified from the cloned gene product (SEQ ID NO: 26) to generate RNA using Primers AY and AZ. The sequences of the primers used to generate mutant F4 TCRs are set forth in Table 16.

TABLE 16

| | Primer | | Sequence | SEQ ID NO: |
|---|---|---|---|---|
| β chain RNA | AO | Forward | GACTAATTAACCCTCACTAAAGGGACACCATGGGCACAAGGTTGTTCTTC | 80 |
| | AP | Reverse | TTTTTTTTTTTTTTTTTTTTTTTTTTTTTTTTTTTTTTTTTTTTTTTTTTTTTTTTTTT TTTTT TCAGAAATCCTTTCTCTTGACCAT | 81 |
| β chain 5' fragment | AQ | Forward | GACTAATTAACCCTCACTAAAGGGACACCATGGGCACAAGGTTGTTCTTC | 82 |
| | AR | Reverse | GTAATGGATCAGCCTCAGCC | 83 |
| F4 mut1 (G70A) | AS | Forward | GCTGAGGCTGATCCATTACTCATATGCCGTTAAAGATACTGACAAAGGAGAAGTC | 84 |
| | AT | Reverse | TTTTTTTTTTTTTTTTTTTTTTTTTTTTTTTTTTTTTTTTTTTTTTTTTTTTTTTTTTT TTTTT TCAGAAATCCTTTCTCTTGACCAT | 85 |

TABLE 16-continued

| | Primer | | Sequence | SEQ ID NO: |
|---|---|---|---|---|
| F4 mut 2 (G70A/V71A) | AU | Forward | GCTGAGGCTGATCCATTACTCATATGCCGCCAAAGATACTGACAAAGGAGAAGTC | 86 |
| | AV | Reverse | TTTTTTTTTTTTTTTTTTTTTTTTTTTTTTTTTTTTTTTTTTTTTTTTTTTTTTTT TTTTT TCAGAAATCCTTTCTCTTGACCAT | 87 |
| Full length Primers | AW | Forward | GACTAATTAACCCTCACTAAAGGGACACCATGGGCACAAGGTTGTTCTTC | 88 |
| | AX | Reverse | TTTTTTTTTTTTTTTTTTTTTTTTTTTTTTTTTTTTTTTTTTTTTTTTTTTTTTTT TTTTT TCAGAAATCCTTTCTCTTGACCAT | 89 |
| α chain RNA | AY | | GACTAATTAACCCTCACTAAAGGGACACCATGCTCCTTGAACATTTATTAATAATC | 90 |
| | AZ | | TTTTTTTTTTTTTTTTTTTTTTTTTTTTTTTTTTTTTTTTTTTTTTTTTTTTTTTT TTTTTCAGC GGACCACAGCCGCAGCGTC | 91 |

***Mutated nucleotides noted by shading.

PBMC from Patient HS were obtained as described in Example 1. Cells were transfected and assayed as described in Example 1, except that nucleic acids encoding the WT F4 alpha chain and the mutant MART-1 beta chains (F4 mut) were used and T2+ cells were pulsed with either 1 μM gp100 peptide KTWGQYWQV (gp100; SEQ ID NO: 93) or MART-1 peptide AAGIGILTV (MART; SEQ ID NO: 94). Also, the following melanoma cells (with phenotypes in ( )) were used: 397-A2 ($A2^+$/MART-$1^+$), 624.38 ($A2^+$/MART-$1^+$), 1300 ($A2^+$/MART-$1^+$), SK23 ($A2^+$/MART-$1^+$), 397-A24 ($A2^+$/MART-$1^-$), 624.28 ($A2^+$/MART-$1^+$), and A375 ($A2^+$/MART-$1^+$).

The amounts of IFN-γ (pg/ml) produced by transfected $CD8^+$ T cells of Patient HS are shown in Table 17, while the amounts of IFN-γ (pg/ml) produced by transfected $CD4^+$ T cells of Patient HS are shown in Table 18.

TABLE 17

| | α chain | | | | | | |
|---|---|---|---|---|---|---|---|
| | WT | WT | WT | WT | WT | WT | |
| | β chain | | | | | | |
| | WT | G70A | G70A/V71A | V71A | K72A | D73A | GFP |
| gp100 | 55 | 58 | 35 | <30 | 31 | <30 | <30 |
| MART | 8650 | 9000 | 6860 | 3910 | 5650 | 690 | 14 |
| 397-A2 | 6910 | 8710 | 1550 | 4036 | 4970 | 110 | <30 |
| 624.38 | 5020 | 4820 | 3206 | 1772 | 3260 | 184 | <30 |
| 1300 | 12850 | 10010 | 7800 | 6540 | 11300 | 1576 | <30 |
| SK23 | 12850 | 10010 | 7800 | 6540 | 1130 | 206 | <30 |
| 397-A24 | <30 | <30 | <30 | <30 | <30 | <30 | <30 |
| 624.28 | <30 | <30 | <30 | <30 | <30 | <30 | <30 |
| A375 | <30 | <30 | <30 | <30 | <30 | <30 | <30 |
| T alone | 5400 | 3930 | 4000 | 2320 | 3600 | <30 | <30 |

TABLE 18

| | α chain | | | | | | |
|---|---|---|---|---|---|---|---|
| | WT | WT | WT | WT | WT | WT | |
| | β chain | | | | | | |
| | WT | G70A | G70A/V71A | V71A | K72A | D73A | GFP |
| gp100 | <30 | <30 | <30 | <30 | <30 | <30 | <30 |
| MART | 83 | 558 | 344 | <30 | 57 | <30 | <30 |
| 397-A2 | 70 | 1618 | 1473 | <30 | <30 | <30 | <30 |
| 624.38 | 77 | 1060 | 1203 | <30 | 42 | <30 | <30 |
| 1300 | 435 | 14760 | 16220 | 82 | 369 | <30 | <30 |
| SK | 88 | 1150 | 1251 | <30 | 68 | <30 | <30 |
| 397-A24 | <30 | <30 | <30 | <30 | <30 | <30 | <30 |
| 624.28 | <30 | <30 | <30 | <30 | <30 | <30 | <30 |
| A375 | <30 | <30 | <30 | <30 | <30 | <30 | <30 |
| T alone | <30 | <30 | <30 | <30 | <30 | <30 | <30 |

This example demonstrated that the F4 mutants F4 mut 1 (G70A) and F4 mut 2 (G70A/V71A) were TCRs that have enhanced ability to recognize tumor target cells without having a decrease in antigen specificity.

Example 5

This example demonstrates a method of treating a disease in a host using the inventive TCRs.

Adoptive cell transfer is carried out as described in Morgan et al. (2006), supra. Briefly, PBLs are obtained by leukopheresis from a metastatic melanoma patient who is HLA-A*0201 positive. The PBLs are transduced with nucleic acids encoding a WT alpha chain and a modified beta chain of a TCR specific for either NY-ESO-1 or MART-1 as described in Example 1. The patient receives the transduced cells at the time of maximum lymphodepletion. One month post-adoptive cell transfer, quantitative RT-PCR assays are carried out to reveal whether the presence of the modified TCRs are expressed by cells of the patient. Tumor regression also is analyzed by the methods described in Morgan et al. (2006), supra.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated nucleic acid comprising a nucleotide sequence encoding a modified T cell receptor (TCR) comprising an amino acid sequence of a wild-type (WT) TCR with no more than three amino acid substitutions located in the complementarity determining region 2 (CDR2) of the β chain of the WT TCR, wherein the modified TCR, as compared to the WT TCR, (i) has an enhanced ability to recognize target cells when expressed by CD4+ T cells and (ii) does not exhibit a decrease in antigen specificity when expressed by CD8+ T cells, wherein the modified TCR has antigen specificity for cancer antigen MART-1, and wherein the WT TCR comprises the amino acid sequences of (a) SEQ ID NOs: 9 and 10 or (b) SEQ ID NOs: 11 and 12.

2. The isolated nucleic acid of claim 1 comprising (a) (i) a nucleotide sequence comprising SEQ ID NO: 28 or 29 and (ii) a nucleotide sequence comprising SEQ ID NO: 26; or (b) (i) a nucleotide sequence comprising SEQ ID NO: 32 or 33 and (ii) a nucleotide sequence comprising SEQ ID NO: 30.

3. A recombinant expression vector comprising the nucleic acid of claim 1.

4. A recombinant expression vector comprising the nucleic acid of claim 2.

5. An isolated host cell comprising the recombinant expression vector of claim 3.

6. An isolated host cell comprising the recombinant expression vector of claim 4.

7. The isolated host cell of claim 5, wherein the cell is a peripheral blood lymphocyte (PBL).

8. The isolated host cell of claim 6, wherein the cell is a peripheral blood lymphocyte (PBL).

9. The isolated host cell of claim 8, wherein the PBL is a CD8+ T cell or a CD4+ T cell.

10. A population of cells comprising at least one host cell of claim 5.

11. A population of cells comprising at least one host cell of claim 6.

12. A population of cells comprising at least one host cell of claim 8.

13. A population of cells comprising at least one host cell of claim 9.

14. The isolated nucleic acid of claim 1, wherein the amino acid substitutions are conservative amino acid substitutions.

15. The isolated nucleic acid of claim 14, wherein the conservative amino acid substitutions are selected from the group consisting of T→A, G→A, A→I, T→V, A→M, T→I, A→V, T→G, and T→S.

16. The isolated nucleic acid of claim 1, wherein the modified TCR comprises an amino acid sequence selected from the group consisting of SEQ ID NOs: 4 to 6, 13, and 95 to 103.

17. The isolated nucleic acid of claim 16, wherein the modified TCR comprises an amino acid sequence selected from the group consisting of SEQ ID NOs: 17 to 20, 37 to 39, and 104 to 109.

18. The isolated nucleic acid of claim 17, wherein the modified TCR comprises the amino acid sequence of:

(i) any of SEQ ID NOs: 17, 20, 37 to 39, and 104 to 109 in combination with SEQ ID NO: 9; or (ii) SEQ ID NO: 18 or 19 in combination with SEQ ID NO: 11.

* * * * *